(12) United States Patent
Buse et al.

(10) Patent No.: US 11,098,343 B2
(45) Date of Patent: Aug. 24, 2021

(54) SYSTEMS AND METHODS FOR PERFORMING ASSAYS

(71) Applicant: GEN-PROBE INCORPORATED, San Diego, CA (US)

(72) Inventors: David A. Buse, San Diego, CA (US); David Opalsky, San Diego, CA (US); Jason F. Rhubottom, Oceanside, CA (US); Norbert D. Hagen, Carlsbad, CA (US); Jennifer L. Tidd, Vista, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 200 days.

(21) Appl. No.: 16/011,229

(22) Filed: Jun. 18, 2018

(65) Prior Publication Data

US 2018/0298426 A1 Oct. 18, 2018

Related U.S. Application Data

(63) Continuation of application No. 14/212,261, filed on Mar. 14, 2014, now abandoned.
(Continued)

(51) Int. Cl.
*C12Q 1/6806* (2018.01)
*B01L 3/00* (2006.01)
(Continued)

(52) U.S. Cl.
CPC ........ *C12Q 1/6806* (2013.01); *B01L 3/50825* (2013.01); *B01L 3/565* (2013.01);
(Continued)

(58) Field of Classification Search
None
See application file for complete search history.

(56) References Cited

U.S. PATENT DOCUMENTS

2004/0134750 A1* 7/2004 Luoma, II .............. G01N 35/04
198/340
2005/0013736 A1* 1/2005 McKeever ......... G01N 35/0092
422/63
(Continued)

FOREIGN PATENT DOCUMENTS

CN 101799477 A 8/2010
CN 101802164 A 8/2010
(Continued)

OTHER PUBLICATIONS

PCT Search Report and Written Opinion, International application No. PCT/US2014/029538, dated Nov. 24, 2014.
(Continued)

*Primary Examiner* — Kathryn Wright
(74) *Attorney, Agent, or Firm* — Sterne, Kessler, Goldstein & Fox P.L.L.C.; Charles B. Cappellari

(57) ABSTRACT

A processing module is configured to extend the capabilities of an analyzer configured to process substances within each of a plurality of receptacles. The module includes a container transport configured to transport a container from a location within the processing module to a location within the analyzer that is accessible to a substance transfer device of the analyzer. A receptacle distribution system is configured to receive a receptacle from the analyzer, transfer the receptacle into the processing module, and to move the receptacle between different locations within the analyzer. A substance transfer device of the module is configured to dispense substances into or remove substances from the receptacle within the processing module. A reagent card exchanger provides an input device for inserting reagent cards into and removing reagent cards from the module, stores reagent cards within the module, and transfers reagent cards to different location within the module.

17 Claims, 35 Drawing Sheets

Related U.S. Application Data

(60) Provisional application No. 61/784,994, filed on Mar. 14, 2013.

(51) Int. Cl.
  *B01L 7/00* (2006.01)
  *C12Q 1/686* (2018.01)
  *G01N 35/04* (2006.01)

(52) U.S. Cl.
  CPC ............ *B01L 7/5255* (2013.01); *C12Q 1/686* (2013.01); *G01N 35/04* (2013.01); *B01L 3/527* (2013.01); *B01L 2200/026* (2013.01); *B01L 2200/0689* (2013.01); *B01L 2300/046* (2013.01); *G01N 2035/0418* (2013.01); *G01N 2035/0436* (2013.01)

(56) References Cited

U.S. PATENT DOCUMENTS

| | | | |
|---|---|---|---|
| 2005/0053454 A1* | 3/2005 | Wiggli | G01N 35/0099 414/752.1 |
| 2009/0130745 A1 | 5/2009 | Williams et al. | |
| 2010/0124518 A1* | 5/2010 | Koike | G01N 35/026 422/65 |

FOREIGN PATENT DOCUMENTS

| | | | |
|---|---|---|---|
| EP | 2187220 | A2 | 5/2010 |
| JP | 2016-513975 | A | 5/2016 |
| WO | 99/57561 | A2 | 11/1999 |
| WO | 00/060362 | A1 | 10/2000 |
| WO | 01/55708 | A2 | 8/2001 |
| WO | 2007/122226 | A2 | 11/2007 |
| WO | 2009/054870 | A2 | 4/2009 |
| WO | 2012/012779 | A2 | 1/2012 |
| WO | 2014/153193 | A2 | 9/2014 |

OTHER PUBLICATIONS

SIPO First Office Action, Chinese Application No. 201810247556.9, dated Dec. 23, 2020.
SIPO Search Report, Chinese Application No. 201810247556.9, dated Dec. 16, 2020.
JPO Official Action, Japanese Patent Application No. 2019-019715, dated Jan. 29, 2020.
JPO Penultimate Official Action, Japanese Patent Application No. 2019-019715, dated Dec. 24, 2020.
HEID et al., "Real Time Quantitative PCR," Genome Res.., 1996, 6(10):986-994, Cold Spring Harbor Laboratory Press, U.S.A.
Qi et al., "Implication of C-Terminal Deletion on the Structure and Stability of Bovine p-casein," Protein J., 2005, 24(7-8):431-444, Springer Science+Business Media, Inc. U.S.A.

* cited by examiner

SYSTEMS AND METHODS FOR PERFORMING ASSAYS

CROSS-REFERENCE TO RELATED APPLICATIONS

This application is a continuation of and claims priority to U.S. application Ser. No. 14/212,261, filed Mar. 14, 2014, which claims priority to U.S. Provisional Application No. 61/784,994, filed Mar. 14, 2013. The entire content of each of these applications is incorporated herein by reference thereto.

BACKGROUND

1. Field of the Invention

The present disclosure relates to diagnostic systems and methods for performing a plurality of different molecular assays on a plurality of samples and, particularly, molecular assays that comprise target nucleic acid amplification reactions.

2. Background

None of the references described or referred to herein are admitted to be prior art to the claimed invention.

Diagnostic assays are widely used in clinical diagnosis and health science research to detect or quantify the presence or amount of biological antigens, cell or genetic abnormalities, disease states, and disease-associated pathogens or genetic mutations in an organism or biological sample. Where a diagnostic assay permits quantification, practitioners may be better able to calculate the extent of infection or disease and to determine the state of a disease over time. Diagnostic assays are frequently focused on the detection of chemicals, proteins or polysaccharides antigens, nucleic acids, biopolymers, cells, or tissue of interest. A variety of assays may be employed to detect these diagnostic indicators.

Nucleic acid-based assays, in particular, generally include multiple steps leading to the detection or quantification of one or more target nucleic acid sequences in a sample. The targeted nucleic acid sequences are often specific to an identifiable group of cells, tissues, organisms, or viruses, where the group is defined by at least one shared sequence of nucleic acid that is common to members of the group and is specific to that group in the sample being assayed. A variety of nucleic acid-based detection methods are fully described by Kohne, U.S. Pat. No. 4,851,330, and Hogan, U.S. Pat. No. 5,541,308, the disclosures of each of which are hereby incorporated by reference.

A nucleic acid-based assay is performed, for example, in part by exposing a sample to a probe configured to exhibit specificity, under particular hybridization conditions, for a nucleic acid sequence belonging to the protein, cell, tissue, organism, or virus of interest. The sample is frequently treated in some manner to extract nucleic acids in a manner that they are eligible for hybridization.

Before or after exposing the target nucleic acid to a probe, the target nucleic acid can be immobilized by target-capture means, either directly or indirectly, using a "capture probe" bound to a substrate, such as a magnetic bead, or particle. Target capture probes are generally short nucleic acid sequences (i.e., oligonucleotide) capable of hybridizing with a sequence of nucleic acid that contains the target sequence. When magnetic beads comprise capture probes, magnets in close proximity to the reaction vessel are used to draw and hold the magnetic beads to the side of the vessel. Once the target nucleic acid is thus immobilized, the hybridized nucleic acid can be separated from non-hybridized nucleic acid present in the sample by, for example, aspirating fluid from the reaction vessel and optionally performing one or more wash steps.

In most instances, it is desirable to amplify the target sequence using any of several nucleic acid amplification procedures which are well known in the art. Methods of nucleic acid amplification are thoroughly described in the literature. Polymerase Chain Reaction ("PCR") amplification, for instance, is described by Mullis et al. in U.S. Pat. Nos. 4,683,195, 4,683,202 and 4,800,159, and in *Methods in Enzymology*, 155:335-350 (1987), the disclosure of each of which is hereby incorporated by reference. Examples of SDA can be found in Walker, *PCR Methods and Applications*, 3:25-30 (1993), Walker et al. in *Nucleic Acids Res.*, 20:1691-1996 (1992) and *Proc. Natl. Acad. Sci.*, 89:392-396 (1991). LCR is described in U.S. Pat. Nos. 5,427,930 and 5,686,272, the disclosure of each of which is hereby incorporated by reference. Examples of transcription-associated amplification ("TAA") formats are provided, for example, in Burg et al. in U.S. Pat. No. 5,437,990; Kacian et al. in U.S. Pat. Nos. 5,399,491 and 5,554,516; and Gingeras et al. in International Application No. PCT/US87/01966 (published as International Publication No. WO 88/01302), and International Application No. PCT/US88/02108 (published as International Publication No. WO 88/10315), the disclosure of each of which is hereby incorporated by reference.

In general, PCR is a biochemical technology to amplify a single or a few copies of a piece of a nucleic acid across several orders of magnitude, generating thousands to millions of copies of a particular nucleic acid sequence. PCR is a common and often indispensable technique used in medical and biological research labs for a variety of applications, including nucleic acid cloning for sequencing, nucleic acid-based phylogeny, or functional analysis of genes; the diagnosis of hereditary diseases; the identification of genetic fingerprints (used in forensic sciences and paternity testing), and the detection and diagnosis of infectious diseases.

The method relies on thermal cycling, consisting of cycles of repeated heating and cooling of the reaction for nucleic acid melting and enzymatic replication of the nucleic acid. Primers (short DNA fragments) containing sequences complementary to the target region along with a nucleic acid polymerization enzyme are key components to enable selective and repeated amplification. As PCR progresses, the nucleic acid generated is itself used as a template for replication, setting in motion a chain reaction in which the nucleic acid template is exponentially amplified.

Because the probe hybridizes to the targeted sequence or its amplicon in a manner permitting detection of a signal indicating the presence of the targeted nucleic acid sequence in a sample, the strength of the signal is proportional to the amount of target nucleic acid sequence or its amplicon that is present. Accordingly, by periodically measuring, during the amplification process, a signal indicative of the presence of amplicon, the growth of amplicon overtime can be detected. Based on the data collected during this "real-time" monitoring of the amplification process, the amount of the target nucleic acid that was originally in the sample can be ascertained. In one context, collecting data "real-time" means collecting data while a reaction or other process is in progress, as opposed to collecting data at the conclusion of the reaction or process. Systems and methods for real time detection and for processing real time data to ascertain nucleic acid levels are described, for example, in Lair, et al., U.S. Pat. No. 7,932,081, "Signal Measuring System for Conducting Real-Time Amplification Assays," the disclosure of which is hereby incorporated by reference.

To detect different nucleic acids of interest in a single assay, different probes configured to hybridize to different nucleic acids, each of which may provide detectibly different signals can be used. For example, different probes configured to hybridize to different targets can be formulated with fluorophores that fluoresce at a predetermined wavelength when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices constructed and arranged to periodically measure signal emissions during the amplification process, and with different signal detecting devices being configured to generate excitation signals of different wavelengths and to measure emission signals of different wavelengths.

SUMMARY OF THE DISCLOSURE

Aspects of the present disclosure are embodied in systems, apparatus, and processes that, inter alia, enhance the functionality of certain diagnostic analyzers by supporting processing capabilities that are not available in the base analyzer or existing modules within the base analyzer. In one embodiment, the systems, apparatus, and processes extend the functionality of a nucleic acid diagnostic analyzer by supporting PCR assay processing and analysis capabilities in addition to isothermal amplification processing and analysis capabilities. A processing extension module is operatively coupled to the base analyzer to extend the overall system capabilities of the analyzer-module system. Providing this extension module imparts sample-to-answer capabilities for a single automated instrument that, when incorporated, will be capable of automatically performing both thermocycling and isothermal amplification assays in endpoint and real-time formats using chemiluminescent and/or fluorescent labels.

In one exemplary embodiment, the base analyzer comprises a dual format molecular diagnostic instrument designed to run specific target-amplified assays, utilizing chemiluminescence and fluorescence detection technologies for both qualitative and real time, quantitative assays. With the addition of the processing extension module, in this embodiment additional automated assays, such as PCR assays, can be run (intermixed) with assays performed by the base analyzer and achieve similar throughput that is achieved by the base analyzer.

In one exemplary embodiment, the processing extension module comprises a thermal cycler with real time fluorescence detection capabilities, a reagent card storage bay that allows for loading and cooled storage of new reagent cards containing reagents, e.g., for PCR, additional disposable pipettor tip trays, PCR- and assay-specific reagents, and one or more a pipettor systems to perform the assay steps needed for the PCR or other reaction and/or reaction receptacle transport. The processing extension module may rely on the base analyzer for sample input, sample preparation, target capture, and other processing steps, such as the addition of elution for subsequent PCR assays, and thus the processing extension module further leverages those capabilities of the base analyzer and supports additional processing and diagnostic capabilities without requiring that the sample input and preparation functionality be built into the processing extension module.

Aspects of the disclosure are embodied in a processing module for enhancing the capabilities of an analyzer configured to process substances within each of a plurality of receptacles and including a first substance transfer device configured to dispense substances into each receptacle and a receptacle transfer apparatus configured to move the receptacles within the analyzer. The processing module is constructed and arranged to be coupled to or decoupled from the analyzer and comprises a container transport constructed and arranged to transport at least one container from a location within the processing module to a location within the analyzer that is accessible to the first substance transfer device to transfer substance from the container to a receptacle within the analyzer, a receptacle distribution system constructed and arranged to receive a receptacle from the receptacle transfer apparatus of the analyzer, transfer the receptacle into the processing module, and move the receptacle between different locations within the analyzer, and a second substance transfer device constructed and arranged to dispense substances into or remove substances from the receptacle within the processing module.

According to some aspects of the disclosure, the receptacle distribution system comprises a receptacle distribution module constructed and arranged to move a receptacle onto the receptacle distribution module at a first location on the processing module, carry the receptacle from the first location to a second location on the processing module that is different from the first location, and move the receptacle off the receptacle distribution module at the second location on the processing module. The receptacle handoff module constructed and arranged to receive a receptacle from the receptacle transfer apparatus of the analyzer and to reposition the receptacle to present the receptacle to the receptacle distribution module to be moved by the receptacle distribution module from the receptacle handoff module onto the receptacle distribution module.

According to some aspects of the disclosure, the receptacle distribution module is constructed and arranged to rotate about an axis of rotation to move a receptacle carried thereby in an arced path between locations within the processing module.

According to some aspects of the disclosure, the processing module further comprises receptacle storage stations for holding one or more receptacles transferred from the analyzer over to the processing module, wherein the receptacle storage stations are arranged in a configuration corresponding to the arced path of the receptacle distribution module.

According to some aspects of the disclosure, the receptacle distribution module is constructed and arranged to move vertically to move a receptacle carried thereby between different vertically-disposed locations within the processing module.

According to some aspects of the disclosure, the receptacle handoff module is constructed and arranged to rotate between a first position for receiving a receptacle from the receptacle transfer apparatus of the analyzer and a second position for presenting the receptacle to the receptacle distribution module.

According to some aspects of the disclosure, the processing module further comprises a container drawer, configured to hold one or more fluid containers and be moved between an opened position and a closed position and to, when moved to the closed position, place at least one fluid container into an operative position with respect to the container transport so that the container can be transported by the container transport from the container drawer into the analyzer.

According to some aspects of the disclosure, the processing module further comprises a container carriage configured to carry one or more containers and be movable with the container drawer and further configured to be engaged by the container transport when the container drawer is in the closed position such that the container transport is operable to move the container carriage and the one or more containers carried thereby from the container drawer into the analyzer.

According to some aspects of the disclosure, the processing module further comprises a carriage transport and a carriage lock. The carriage transport is moveable with the container drawer and constructed and arranged to carry the container carriage between a first position when the container drawer is in the opened position and a second position when the container drawer is in the closed position. The carriage lock is constructed and arranged to lock the container carriage to the carriage transport when the carriage transport is in the first position and to release the container from the carriage transport when the carriage transport is in the second position to permit the container carriage to be removed from the carriage transport by the container transport.

According to some aspects of the disclosure, the container transport comprises a track extending from the container drawer into the analyzer, a carriage hook configured to engage the container carriage when the container drawer is in the closed position, and a motorized carriage hook drive system constructed and arranged to effect powered translation of the carriage hook along the carriage track.

According to some aspects of the disclosure, the motorized carriage hook drive system comprises a motor and a belt driven by the motor and coupled to the carriage hook.

According to some aspects of the disclosure, the processing apparatus further comprises one or more position sensors disposed at one or more locations along the track to detect a position of the carriage on the track.

According to some aspects of the disclosure, the processing module further comprises a reagent card changer comprising a card input device and a card storage device. The card input device is constructed and arranged to enable a user to place a reagent card containing at least one reagent into the processing module or remove a reagent card from the processing module. The card storage chamber is configured to hold a plurality of reagent cards until needed for processing within the processing module. The receptacle distribution system is further constructed and arranged to move a reagent card between the card input device and the card storage chamber.

According to some aspects of the disclosure, the processing module further comprises one or more reagent card loading stations, each configured to hold a reagent card in a location and orientation that permits the second substance transfer device to transfer a substance to or from the reagent card.

According to some aspects of the disclosure, the processing module further comprises a charged field generator operatively associated with at least one of the card input device, the card storage chamber, and the reagent card loading stations and constructed and arranged to generate electrostatic forces to position and hold a reagent present in a reagent card held in the card input device or card storage chamber. In related aspects the charged field generator is situated below at least one of the card input device, the card storage chamber, and the reagent card loading stations such that electromagnetic forces are applied to, or adjacent to, the bottom of one or more wells of a reagent card, when present.

According to some aspects of the disclosure, wherein the card input device comprises a card carousel that is rotatable about an axis of rotation, wherein the card carousel includes a plurality of reagent card stations, each configured to hold a reagent card, disposed around the axis of rotation.

According to some aspects of the disclosure, the card carousel is disposed in a drawer that is movable between an open position providing access to the card carousel and a closed position closing off access to the card carousel.

According to some aspects of the disclosure, the processing module further comprises a code reader operatively disposed with respect to the card input device and constructed and arranged to read a machine readable code on each reagent card carried in the card input device.

According to some aspects of the disclosure, the processing module further comprises a card storage carousel disposed within the card storage. The card storage carousel is rotatable about an axis of rotation and includes a plurality of reagent card stations, each configured to hold a reagent card, disposed around the axis of rotation.

According to some aspects of the disclosure, the reagent card stations of the card storage carrousel are disposed on more than one level.

According to some aspects of the disclosure, the processing module further including a cooling system for maintaining the storage chamber a lower than ambient temperature.

According to some aspects of the disclosure, the second substance transfer device comprises a robotic pipettor having a pipettor probe, and the processing module further comprises one or more disposable tip drawers constructed and arranged to hold a plurality of disposable tips configured to be placed on the pipettor probe of the robotic pipettor.

According to some aspects of the disclosure, the processing module further comprises a cap/vial tray constructed and arranged to hold a plurality of processing vials and/or associated caps. Each cap is configured to be coupled to an associated vial to close the associated vial. The vials are accessible by the robotic pipettor to dispense processing material into the vials, and the associated caps are accessible by the robotic pipettor to move each cap into an associated vial to form a cap/vial assembly. The robotic pipettor is configured to move the cap/vial assembly from the cap/vial tray to another location on the processing module.

According to some aspects of the disclosure, the processing module further comprises a centrifuge, wherein the robotic pipettor is constructed and arranged to move a cap/vial assembly from the cap/vial tray to the centrifuge.

According to some aspects of the disclosure, the processing module further comprises a thermal cycler configure to hold a plurality of cap/vial assemblies and to subject the contents of the plurality of cap/vial assemblies to cyclically varying temperatures and a robotic vial transfer pipettor configured to move a cap/vial assembly from the centrifuge to the thermal cycler.

According to some aspects of the disclosure, the processing module further comprises one or more magnetic receptacle holding slots configured to hold a receptacle transferred from the analyzer to the processing module. Each magnetic receptacle holding slot comprises a magnet and is constructed and arranged to draw magnetic particles contained within the receptacle to a wall of the receptacle and out of solution within the fluid contents of the receptacle.

According to some aspects of the disclosure, the analyzer and the processing module are configured to conduct nucleic acid amplification reactions.

According to some aspects of the disclosure, the nucleic acid amplification reactions conducted in the analyzer and the processing module are different types of amplification reactions.

According to some aspects of the disclosure, the nucleic acid amplification reaction conducted in the analyzer comprises a qualitatively monitored reaction and the nucleic acid amplification reaction conducted in the processing module comprises a quantitatively monitored reaction.

According to some aspects of the disclosure, the nucleic acid amplification reaction conducted in the processing module comprises a reaction monitored in real-time.

According to some aspects of the disclosure, wherein the nucleic acid amplification reaction conducted in the analyzer is an isothermal reaction, and the nucleic acid amplification reaction conducted in the processing module comprises the use of a polymerase chain reaction.

Aspects of the disclosure are further embodied in an automated system capable of performing multiple molecular assays on a single sample. The system comprises a sample input portal constructed and arranged to accept samples contained in one or more receptacles, a sample processing module constructed and arranged to prepare a sample provided to the sample input portal for a nucleic acid amplification reaction, a first module constructed and arranged to conduct an isothermal nucleic acid amplification assay with the sample, a second module constructed and arranged to conduct a nucleic acid amplification assay involving temperature fluctuation with the sample, and a transport mechanism constructed and arranged to effect automated transport of one or more receptacles containing the sample between the sample input portal, the sample processing module, the first module, and the second module.

According to some aspects of the disclosure, the automated system further comprises a fluid transfer apparatus constructed and arranged to access the sample when present in the sample processing module, the first module, or the second module.

According to some aspects of the disclosure, the system further comprises a reagent storage compartment constructed and arranged to hold a plurality of reagent containers, wherein the reagent storage compartment is held at a temperature below ambient temperature.

According to some aspects of the disclosure, the system further comprises a reagent container transport mechanism constructed and arranged to transport one or more reagent containers between the reagent storage compartment and a separate location within the second module.

According to some aspects of the disclosure, the reagent container transport mechanism is constructed and arranged to transport the reagent containers within the second module and to transport the receptacles within the second module.

Some aspects of the disclosure are embodied in a method for improved thermocycling of low volume nucleic acid amplification reaction mixtures. The method comprises combining a fluid sample together with one or more amplification reaction reagents in a reaction receptacle using an automated pipettor, transporting the reaction receptacle to a centrifuge using the automated pipettor, centrifuging the fluid contents of the reaction receptacle, automatically removing the reaction receptacle from the centrifuge after centrifugation and placing the reaction receptacle in a thermocycler, and subjecting the fluid contents of the reaction receptacle to one or more temperature cycles within the thermocycler.

According to some aspects of the disclosure, the reaction receptacle is removed from the centrifuge and transported to the thermocycler using the automated pipettor.

According to some aspects of the disclosure, the reaction receptacle is placed in the centrifuge at a first location, and the reaction receptacle is removed from the centrifuge at a second, different location.

According to some aspects of the disclosure, the method further comprises a second automated pipettor, and the second automated pipettor automatically removes the reaction receptacle from the centrifuge after centrifugation and places the reaction receptacle in the thermocycler.

According to some aspects of the disclosure, the receptacle is sealed by a cap prior to transporting the sealed receptacle to the centrifuge.

According to some aspects of the disclosure, the automated pipettor transports the cap to the receptacle and seals the receptacle by coupling the cap to the receptacle.

Some aspects of the disclosure are embodied in an improved method of preparing multiple different nucleic acid reaction mixtures within the workflow of an automated molecular instrument. The method comprises providing two or more reaction receptacles, providing two or more unit dose reagent containers, each unit dose reagent container corresponding to a respective reaction receptacle, and each unit dose reagent container containing a nucleic acid amplification reagent that is specific for one or more target nucleic acids, providing a receptacle containing a first bulk reagent, and combining at least a portion of the sample with at least a portion of the unit dose reagent and at least a portion of the bulk reagent in each of the two or more reaction receptacles. After combination, each reaction receptacle contains a different sample, a different unit dose reagent, and the same first bulk reagent.

According to some aspects of the disclosure, the method further comprises a receptacle containing a second bulk reagent, wherein the second bulk reagent is dispensed into each of the two or more unit dose reagent containers prior to combining at least a portion of the sample with at least a portion of the unit dose reagent and at least a portion of the bulk reagent in each of the two or more reaction receptacles.

According to some aspects of the disclosure, the second bulk reagent comprises a reconstitution reagent.

According to some aspects of the disclosure, the method further comprises transporting each of the two or more reaction receptacles to a heated incubator to conduct a nucleic acid amplification assay.

Other features and characteristics of the present disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DESCRIPTION OF THE DRAWINGS

The accompanying drawings, which are incorporated herein and form part of the specification, illustrate various, non-limiting embodiments of the present disclosure. In the drawings, common reference numbers indicate identical or functionally similar elements.

DETAILED DESCRIPTION OF THE PREFERRED EMBODIMENT

Figure 1:
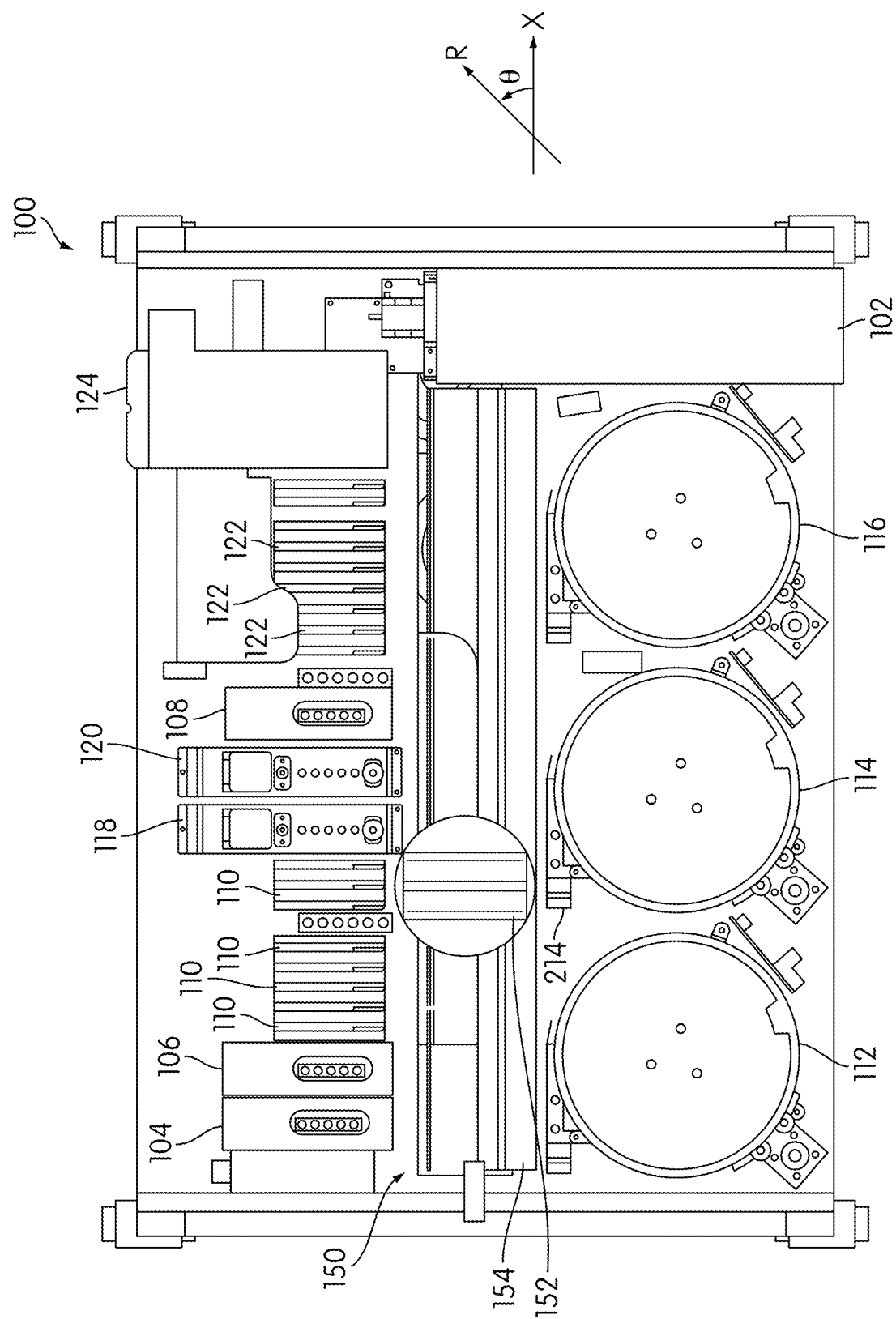
FIG. 1 is a top plan view of an exemplary diagnostic analyzer.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

This description may use relative spatial and/or orientation terms in describing the position and/or orientation of a component, apparatus, location, feature, or a portion thereof.

Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Nucleic Acid Diagnostic Assays

Aspects of the present disclosure involve apparatus and procedures that can be used in conjunction with nucleic acid diagnostic assays, including "real-time" amplification assays and "end-point" amplification assays.

Real-time amplification assays can be used to determine the presence and amount of a target nucleic acid in a sample which, by way of example, is derived from a pathogenic organism (e.g., bacterium) or virus. Thus, real time amplification assays are often referred to as quantitative assays. By determining the quantity of a target nucleic acid in a sample, a practitioner can approximate the amount or load of the organism or virus in the sample. In one application, a real-time amplification assay may be used to screen blood or blood products intended for transfusion for bloodborne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations. Exemplary systems and methods for performing real-time amplification assays are described in U.S. Pat. No. 7,897,337, entitled "Methods for Performing Multi-Formatted Assays," the disclosure of which is hereby incorporated by reference.

In addition to implementation of the disclosure in conjunction with real-time amplification assays, the disclosure may also be implemented in conjunction with end point amplification assays. In end-point amplification assays, the presence of amplification products containing the target sequence or its complement is determined at the conclusion of an amplification procedure. Thus, end-point amplification assays are often referred to as qualitative assays in that such assays do not indicate the amount of a target analyte present, but provide a qualitative indication regarding the presence or absence of the target analyte. Exemplary systems and methods for end-point detection are described in U.S. Pat. No. 6,335,166, entitled "Automated Process For Isolating and Amplifying a Target Nucleic Acid Sequence," the disclosure of which is hereby incorporated by reference. The determination may occur in a detection station that may be located externally to the incubator(s) in which the amplification reactions occur. In contrast, in "real-time" amplification assays, the amount of amplification products containing the target sequence or its complement is determined during an amplification procedure. In the real-time amplification assay, the concentration of a target nucleic acid can be determined using data acquired by making periodic measurements of signals that are functions of the amount of amplification product in the sample containing the target sequence, or its complement, and calculating the rate at which the target sequence is being amplified from the acquired data.

In an exemplary real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to a nucleic acid present in the sample, the fluorescent and quencher moieties are separated from each other and light energy emitted by the fluorescent moiety can be detected. Fluorescent moieties having different and distinguishable excitation and emission wavelengths are often combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties. In another embodiment, different fluorescent moieties having the same excitation wavelength, but different and distinguishable emission wavelengths are combined with different probes. The presence and amount of target nucleic acids associated with each probe can be determined by exposing the sample to a specific wavelength light energy and the light emission from the sample at the different wavelengths corresponding to the different fluorescent moieties is measured.

A variety of different labeled probes and probing mechanisms are known in the art, including those where the probe does not hybridize to the target sequence. See, e.g., U.S. Pat. No. 5,846,717 and PCT Publication No. 2012096523, the disclosure of which is hereby incorporated by reference. The embodiments of the present disclosure operate regardless of the particular labeling scheme utilized provided the moiety to be detected can be excited by a particular wavelength of light and emits a distinguishable emission spectra.

Where an amplification procedure is used to increase the amount of target sequence, or its complement, present in a sample before detection can occur, it is desirable to include a "control" to ensure that amplification has taken place. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus calling into question the results from that assay. Alternatively, failure to detect emission light may be due to failure or deteriorated mechanical and/or electrical performance of an instrument for detecting the emission light.

Assays performed in accordance with the description herein capture, amplify, and detect nucleic acids from target organisms in patient samples employing technologies, such as: Target Capture, Reverse Transcription and Real-Time Polymerase Chain Reaction. The combination of the processes; Reverse Transcription and PCR is abbreviated "RT-PCR." The following is a generalized assay processing description of the different technologies that may be implemented in accordance with aspects of the disclosure.

The target capture process isolates nucleic acid of the target (e.g. virus, bacteria, mammalian cells) and purifies nucleic acid for amplification. The target organism, which can be in a variety of biological matrices from urine to blood, is lysed by Target Capture Reagents ("TCR") and nucleic acid is released. Capture oligonucleotide probes hybridize to a target nucleic acid sequence. The capture sequence/target nucleic acid complexes attach to magnetic particles in the TCR thru nucleic acid hybridization. The magnetic particles are pulled to the side of a container and immobilized by a magnet and potential inhibitory substances are washed away (multiple wash cycles may be performed) to thereby provide a purified reaction mixture containing primarily only the target nucleic acid. As a result, target capture enables the enrichment of a variety of sample types and significantly reduces the inhibition rate and can increase assay sensitivity. Exemplary methods of target nucleic acid capture are provided, for example, in U.S. Pat. No. 6,534,273, entitled "Two-step hybridization and capture of a polynucleotide," the disclosure of which is hereby incorporated by reference.

After completing the target capture process, the magnetic particles on which the target is hybridized are re-suspended, for example, with 20-60 microliters of a low salt buffer or water. This will de-hybridize the target sequence from the magnetic particles and, in the presence of a strong magnet, allow 5-50 microliters of purified nucleic acid to be recovered as input into the RT-PCR process.

Reverse transcription and PCR can be optimized to run in a single receptacle using common reagents as a one-step process. This method provides a sensitive means to detect low-abundance RNAs, and, although the method is not necessarily quantitative, specific controls can be included in the experiment if quantitative results are desired. In an exemplary implementation, prior to performing the Real-Time PCR reaction, RNAs are incubated with a retroviral enzyme (reverse transcriptase) under oil at 42° C. for approximately half an hour. This process creates a single-stranded DNA copy of the RNA. If the goal is to copy all RNAs present in the source material into DNA, nonspecific amplification oligonucleotides or amplification oligonucleotide sets are used. In the case of mRNA, which has a polyadenylated (poly A) tail, an oligo dT amplification oligonucleotide can be used. Alternatively, a collection of randomized hexanucleotide primers can be used to ensure an amplification oligonucleotide will be present that is complementary to each of the messages. If only one RNA target is sought, a sequence-specific primer complementary to the 3' end of the desired amplification product is used. RNase H is used to degrade the RNA molecule contained in the hybrid RNA-DNA duplex, so that the DNA strand is available to direct second-strand synthesis. Single-stranded DNA thus generated can serve as the template for PCR using sequence-specific primers to amplify the region of interest.

The polymerase is inactive at low temperatures and must be heat activated at 95° C. for several minutes (~10) before beginning PCR. Both reactions occur inside a thermocycler (i.e., a module configured to expose the contents of the receptacle to temperatures that are cycled between two or more different temperatures), but Real-Time PCR requires accurate/rapid thermocycling between denaturation (~95° C.), annealing (~55° C.), and synthesis (~72° C.) temperatures. Fluorescence monitoring occurs at one or many color wavelengths—relating to one or many probes adapted to detect one or many target analytes—during each cycle or at another predetermined interval. PCR components include: for example, the forward and reverse amplification oligonucleotides and a fluorogenic oligonucleotide probe containing a reporter fluorescent dye on the 5' end and a quencher dye on the 3' end. During PCR, nucleic acid amplification oligonucleotides hybridize to opposite strands of the target nucleic acid and are oriented with their 3' ends facing each other so that synthesis by a nucleic acid polymerization enzyme, such as a DNA polymerase, extends across the segment of the nucleic acid between them. While the probe is intact, the proximity of the quencher dye greatly reduces the fluorescence emitted by the reporter dye. During amplification if the target nucleic acid sequence is present, the fluorogenic probe anneals downstream from one of the amplification oligonucleotide sites and is cleaved by the 5' nuclease activity of the polymerization enzyme during amplification oligonucleotide extension. The cleavage of the probe separates the reporter dye from the quencher dye, thus rendering detectable the reporter dye signal and removing the probe from the target strand, allowing amplification oligonucleotide extension to continue to the end of the template strand.

One round of PCR synthesis will result in new strands of indeterminate length which, like the parental strands, can hybridize to the amplification oligonucleotides upon denaturation and annealing. These products accumulate arithmetically with each subsequence cycle of denaturation, annealing to amplification oligonucleotides, and synthesis. The second cycle of denaturation, annealing, and synthesis produces two single-stranded products that together compose a discrete double-stranded product which is exactly the length between the amplification oligonucleotide ends. Each strand of this discrete product is complementary to one of the two amplification oligonucleotides and can therefore participate as a template in subsequent cycles. The amount of this product doubles with every subsequent cycle of synthesis, denaturation and annealing. This accumulates exponentially so that 30 cycles should result in a $2^{28}$-fold (270 million-fold) amplification of the discrete product.

Multiple Receptacle Devices

Figure 2:
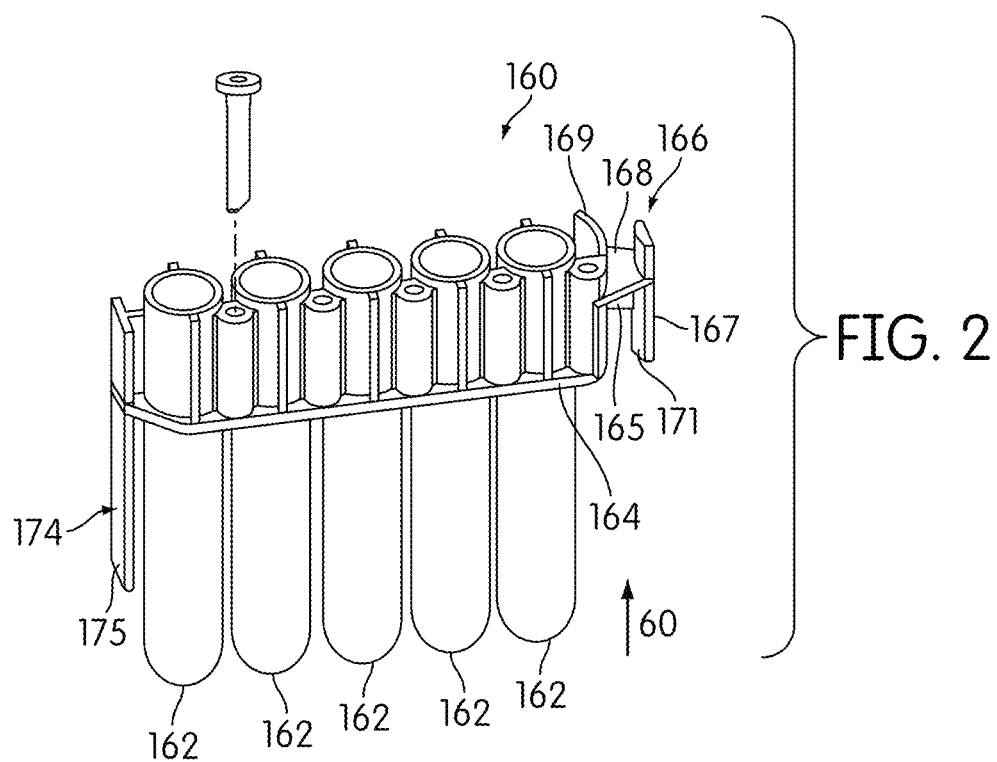
FIG. 2 is a perspective view of a multiple receptacle device ("MRD").

Referring to FIG. 2, a reaction receptacle in the form of an MRD 160 comprises a plurality of individual receptacle vessels, or reaction tubes, 162, preferably five. The receptacle vessels 162, preferably in the form of cylindrical tubes with open top ends and closed bottom ends, are connected to one another by a connecting rib structure 164 which defines a downwardly facing shoulder extending longitudinally along either side of the MRD 160.

Alternatively, the receptacle may comprise any container suitable for holding a fluid or liquid, including a cuvette, beaker, microtiter plate, or test tube. Unless explicitly stated, or the context dictates otherwise, the term "receptacle" will interchangeably refer to an entire MRD, one or more individual receptacle vessels of an MRD, a cuvette, beaker, microtiter plate, test tube, or any other suitable container. Similarly, unless explicitly stated or the context dictates otherwise, descriptions of the disclosure in the context of an MRD or receptacle vessel of an MRD are exemplary and should not be construed as limiting of the scope of the disclosure, as aspects of the disclosure are applicable to any suitable "receptacle."

The MRD 160 is preferably formed from injection molded polypropylene, such as those sold by Montell Polyolefins, of Wilmington, Del., product number PD701NW or Huntsman, product number P5M6K-048. In an alternative embodiment, the receptacle vessels 162 of the MRD are releasably fixed with respect to each other by means such as, for example, a sample tube rack.

An arcuate shield structure 169 is provided at one end of the MRD 160. An MRD manipulating structure 166 extends from the shield structure 169. The manipulating structure 166 is adapted to be engaged by an extendible and retractable hook of a receptacle distributor or a transport mechanism for moving the MRD 160 between different components of a diagnostic analyzer. An exemplary transport mechanism that is compatible with the MRD 160 is described in U.S. Pat. No. 6,335,166, entitled, "Automated Process for Isolating and Amplifying a Target Nucleic Acid Sequence," the disclosure of which is hereby incorporated by reference. The MRD manipulating structure 166 comprises a laterally extending plate 168 extending from shield structure 169 with a vertically extending piece 167 on the opposite end of the plate 168. A gusset wall 165 extends downwardly from lateral plate 168 between shield structure 169 and vertical piece 167.

Figure 3:
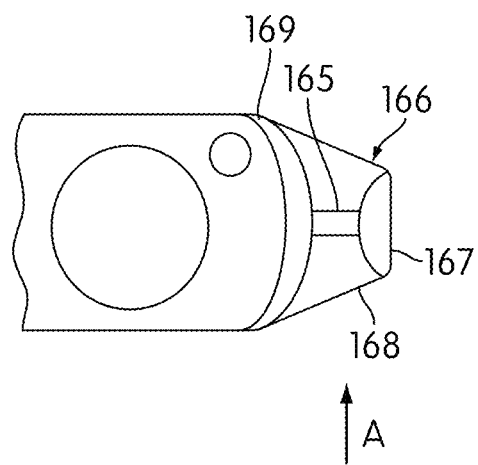
FIG. 3 is a partial bottom view of the MRD.

As shown in FIG. 3, the shield structure 169 and vertical piece 167 have mutually facing convex surfaces. The MRD 160 may be engaged by a receptacle distributor, a transport mechanism, and other components, by moving an engaging member, such as an extendible and retractable hook, laterally (in the direction "A") into the space between the shield structure 169 and the vertical piece 167. The convex surfaces of the shield structure 169 and vertical piece 167 provide for wider points of entry for an engaging member undergoing a lateral relative motion into the space.

A label-receiving structure 174 having a flat label-receiving surface 175 is provided on an end of the MRD 160 opposite the shield structure 169 and MRD manipulating structure 166. Human and/or machine-readable labels, such as scanable bar codes, can be placed on the surface 175 to provide identifying and instructional information on the MRD 160.

Further details regarding the MRD 160 may be found in U.S. Pat. No. 6,086,827, entitled "Reaction Receptacle Apparatus," the disclosure of which is hereby Incorporated by reference.

Analyzer Overview

An analyzer in which the method and apparatus of the present disclosure may be implemented is shown schematically in plan view and designated by reference number 100 in FIG. 1. The analyzer 100 includes various modules configured to receive one or more reaction receptacles (described in more detail below) within each of which is performed one or more steps of a multi-step analytical process, such as a nucleic acid test (NAT) designed to detect a virus or a bacterium, or other chemical, biochemical or biological process. The modules of the analyzer 100 constitute receptacle-receiving structures configured to receive and hold one or more reaction receptacles and, in some instances, to perform processes on the contents of the receptacles. Exemplary processes include, but are not limited to, adding substances, e.g., fluids, such as sample, reagent, buffer, oil, label, probe, or other reaction fluids, to and/or removing substances from the reaction receptacle, agitating the receptacle to mix the contents thereof, maintaining and/or altering the temperature of the contents of the reaction receptacle, heating or chilling the contents of the reaction receptacle, altering the concentration of one or more components of the contents of the reaction receptacle, separating or isolating constituent components of the contents of the receptacle, detecting an electromagnetic signal emission (e.g., light) from the contents of the reaction receptacle, deactivating or halting an on-going reaction, or any combination of two or more of such processes.

In one embodiment, an exemplary analyzer in which the present disclosure may be implemented may include a receptacle input module 102 including structure for receiving and holding one or more empty reaction receptacles prior to the receptacles being used for performing a chemical, biological, or other multi-step process. The receptacle input module 102 may comprise a drawer or cabinet that may be opened and loaded with a plurality of receptacles and may include a receptacle feeding apparatus for moving receptacles, e.g., one or more at a time, into a receptacle pick-up position. In certain preferred embodiments, the receptacle pick-up position comprises a registered or known position of the receptacle to facilitate removal of the receptacle by a receptacle distributor.

Analyzer 100 may further include various containers for holding bulk fluids, such as water, buffer solution, and waste materials. Other modules may be provided for holding containers of reaction fluids, such as reagents, and such modules may be constructed and arranged to maintain the contents of such containers at prescribed storage temperatures and/or to agitate such containers to maintain the contents of the containers in solution or suspension. Analyzer 100 may further include a sample loading module constructed and arranged to receive and hold containers, such as test tubes, containing sample specimens. Fluid transfer apparatuses may be provided for transferring fluids, e.g., sample fluids, reagents, bulk fluids, waste fluids, etc., to and from reaction receptacles and/or other containers. Such fluid transfer apparatuses may comprises one or more robotic pipettor apparatuses configured for controlled, automated movement and access to the reaction receptacles and containers holding reaction fluids and/or bulk fluids and containers holding sample specimens. Fluid transfer apparatuses may also include fluid dispensers, e.g., nozzles, disposed within other modules and connected by suitable fluid conduits to containers, e.g., bulk fluid containers, and to pumps or other apparatus for causing fluid movement from the containers to the dispensers.

Analyzer 100 may further include load stations 104, 106, 108 configured to receive a reaction receptacle and within which one or more materials may be added to the receptacle, including sample material and various reaction reagents, by a fluid transfer apparatus. In an implementation where the analyzer 100 comprises a platform for performing a NAT, reaction reagents may comprise target capture reagents, lysis reagents, nucleic acid amplification reagents, and/or nucleic acid detection reagents, such as probes or labels.

Analyzer 100 may further comprise temperature ramping stations 110 configured to hold one or more reaction receptacles in an environment that is maintained at higher than ambient temperatures so as to raise the temperature of the contents of the receptacles. Exemplary temperature ramping stations are described in U.S. Pat. No. 8,192,992, entitled "System and Method for Incubating the Contents of a Reaction Receptacle," the disclosure of which is hereby incorporated by reference.

Analyzer 100 may further include one or more incubators. The illustrated analyzer 100 includes three incubators 112, 114, 116, each of which is configured to receive a plurality of reaction receptacles and maintain the receptacles in an elevated temperature environment. Exemplary incubators are described in U.S. Pat. No. 7,964,413, entitled "Method for Continuous Mode Processing of the Contents of Multiple Reaction Receptacles in a Real-Time Amplification Assay" and U.S. Patent Application Publication No. 2012/0221252, entitled "Systems and Methods for Distinguishing Optical Signals of Different Modulation Frequencies in an Optical Signal Detector," the respective disclosures of which are hereby incorporated by reference.

Also, in an implementation in which the analyzer 100 comprises a platform for performing a NAT, the analyzer may include sample-processing modules, such as magnetic separation wash stations 118, 120, adapted to separate or isolate an analyte of interest (e.g., a target nucleic acid) bound to a magnetically-responsive target capture material from the remaining contents of the receptacle. Exemplary magnetic separation wash stations are described in U.S. Patent Application Publication No. 2010/0288395, entitled "Method and Apparatus for Effecting Automated Movement of a Magnet in an Instrument for Performing a Magnetic Separation Procedure" and U.S. Pat. No. 6,605,213, entitled "Method and Apparatus for Performing a Magnetic Separation Purification Procedure on a Sample Solution," the respective disclosures of which are hereby incorporated by reference.

Analyzer 100 may further include chilling modules 122 adapted to receive one or more reaction receptacles and hold the receptacles in a lower than ambient temperature environment so as to reduce the temperature of the contents of the receptacles.

Finally, analyzer 100 may include a detector module 124 adapted to receive a reaction receptacle and detect a signal (e.g., an optical signal) emitted by the contents of the reaction receptacle. In one implementation, detector module 124 may comprise a luminometer for detecting luminescent signals emitted by the contents of a receptacle and/or a fluorometer for detecting fluorescent emissions. Analyzer 100 may also include one or more signal detecting apparatuses, such as fluorometers, coupled to one or more of the incubators 112, 114, 116 and configured and controlled to detect, preferably at specified, periodic intervals, signals emitted by the contents of the receptacles contained in the incubator while a process, such as nucleic acid amplification, is occurring within the reaction receptacles. An exemplary luminometer and an exemplary fluorometer are described in previously-incorporated U.S. Pat. No. 7,964,413 and another exemplary fluorometer is described in previously-incorporated U.S. Patent Application Publication No. 2012/0221252.

The analyzer 100 further includes a receptacle transfer apparatus, which, in the illustrated embodiment, comprises a receptacle distributor 150. The modules of the analyzer 100 may include a receptacle transfer portal through which receptacles can be inserted into or removed from the respective modules. Each module may or may not include an openable door covering its receptacle portal. The receptacle distributor 150 is configured to move receptacles between the various modules and retrieve receptacles from the modules and deposit receptacles into the modules. In one exemplary embodiment, the receptacle distributor 150 includes a receptacle distribution head 152 configured to move in an X direction along a transport track assembly 154, rotate in a theta (θ) direction, and move receptacles in an R direction into and out of the receptacle distribution head 152 and one of the modules of analyzer 100. An exemplary receptacle distributor is described in U.S. Patent Application Publication No. 2012/128451, entitled "Method and Apparatus for Effecting Transfer of Reaction Receptacles in an Instrument for Multi-Step Analytical Procedure," the disclosure of which is hereby incorporated by reference.

Processing Extension Module

Aspects of the disclosure are embodied in a processing extension module 400 that may be operatively coupled to a diagnostic instrument, such as analyzer 100 described above. Specific examples of suitable diagnostic instruments to which the processing extension module 400 may be coupled include molecular diagnostic instruments, such as the "PANTHER" system available from Hologic, Inc. In one exemplary embodiment, the processing extension module is configured to perform PCR amplification assays and measure real time fluorescence during the amplification process. A controller directs the component modules of the analyzer 100 and the processing extension module 400 to perform the assay steps. In one exemplary embodiment, the analyzer 100 houses all the computer, fluids, reagents, consumables, and mechanical modules to perform the specified assays, such as TMA assays. As explained above, the controller may comprise a computer and preferably can accommodate LIS ("laboratory information system") connectivity and as well as remote user access. The processing extension module 400 houses component modules that enable PCR assays, melting analyses, and optionally additional functionalities. Other components may include a printer and an optional uninterruptible power supply.

Figure 4:
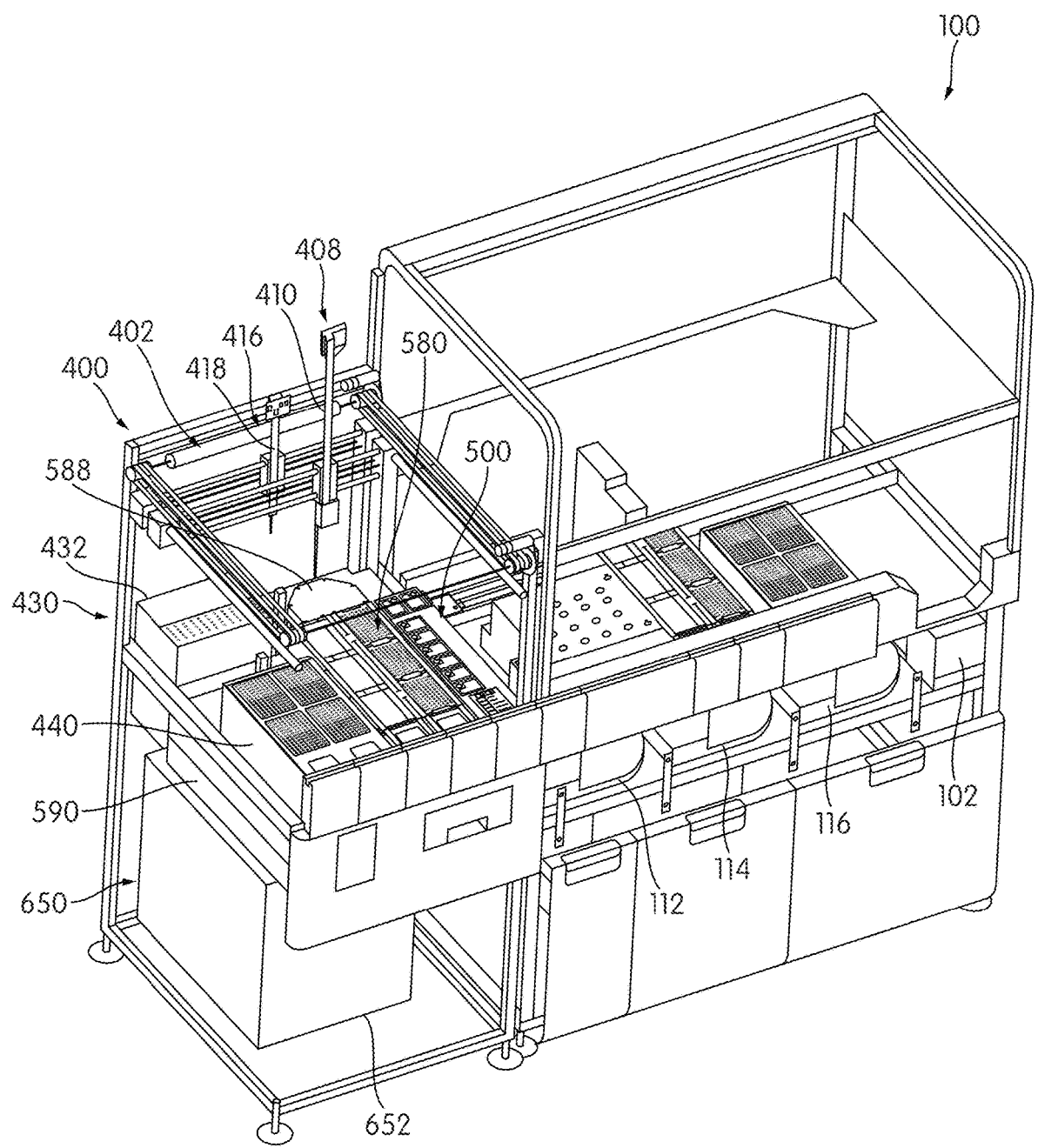
FIG. 4 is a perspective view of a diagnostic analyzer with a Processing extension module embodying aspects of the present disclosure coupled thereto.
Figure 5:
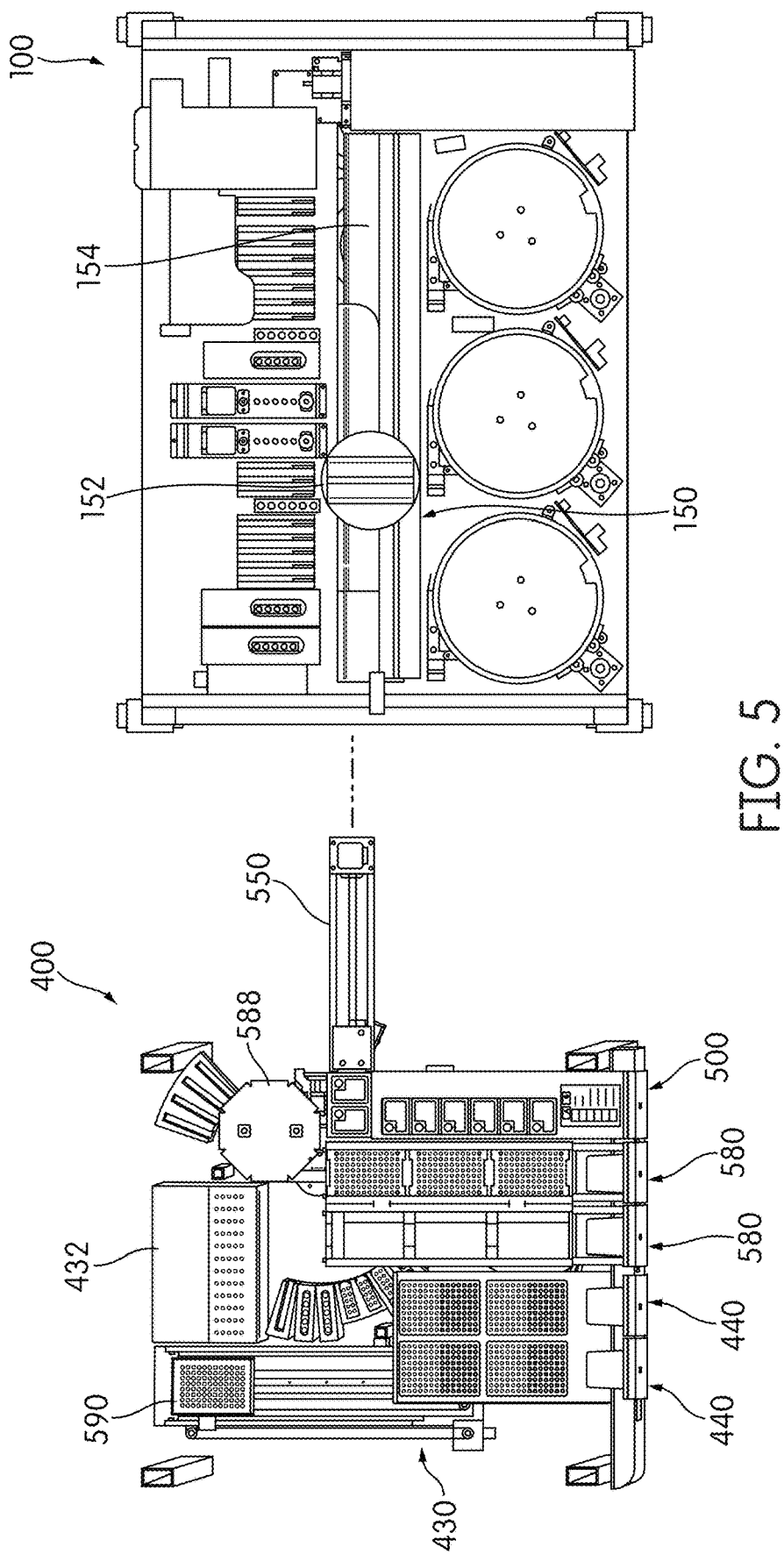
FIG. 5 is an exploded, top plan view of the diagnostic analyzer and the Processing extension module.
Figure 6:
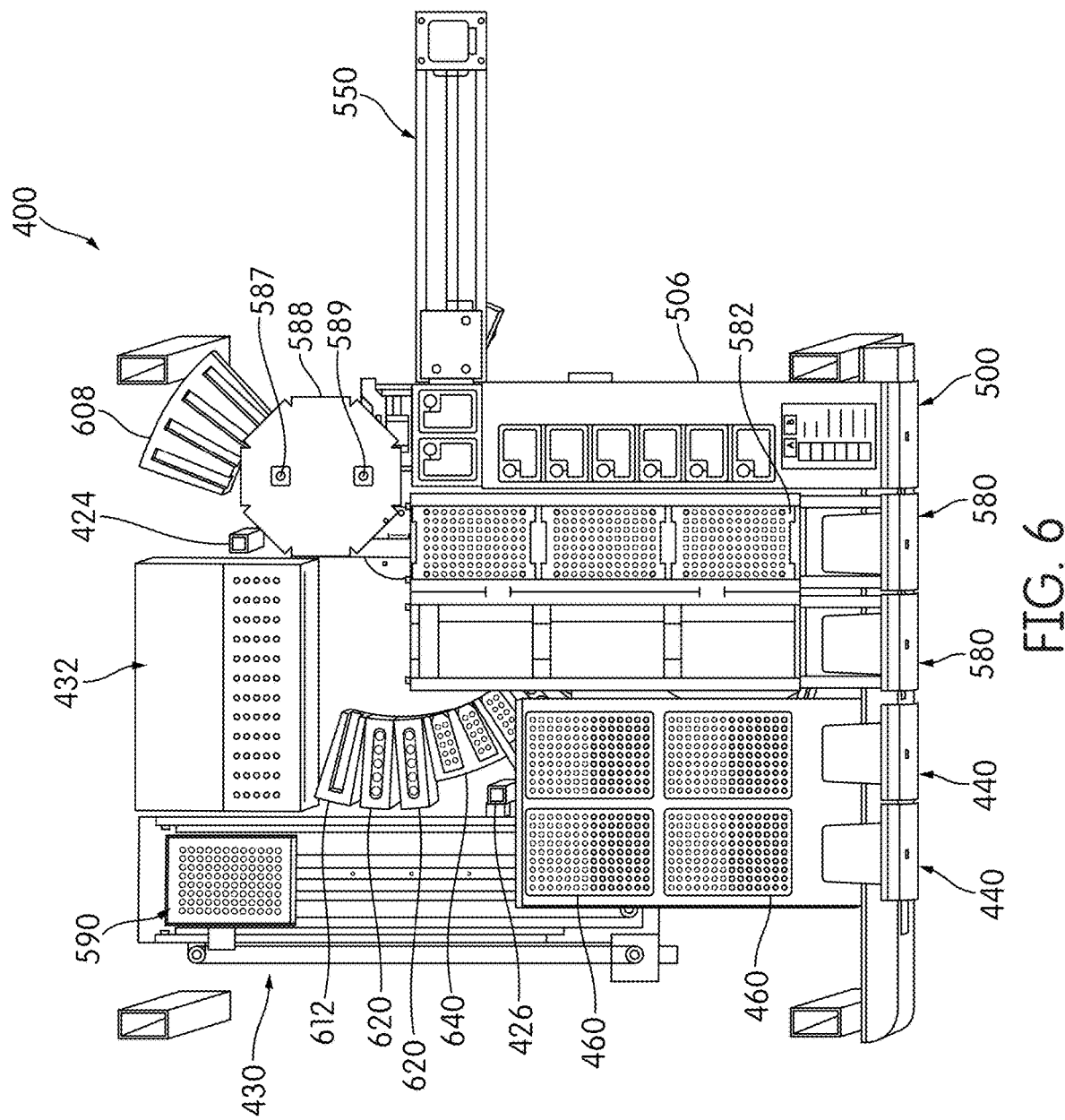
FIG. 6 is a top plan view of a PCR deck of the processing extension module.
Figure 14:
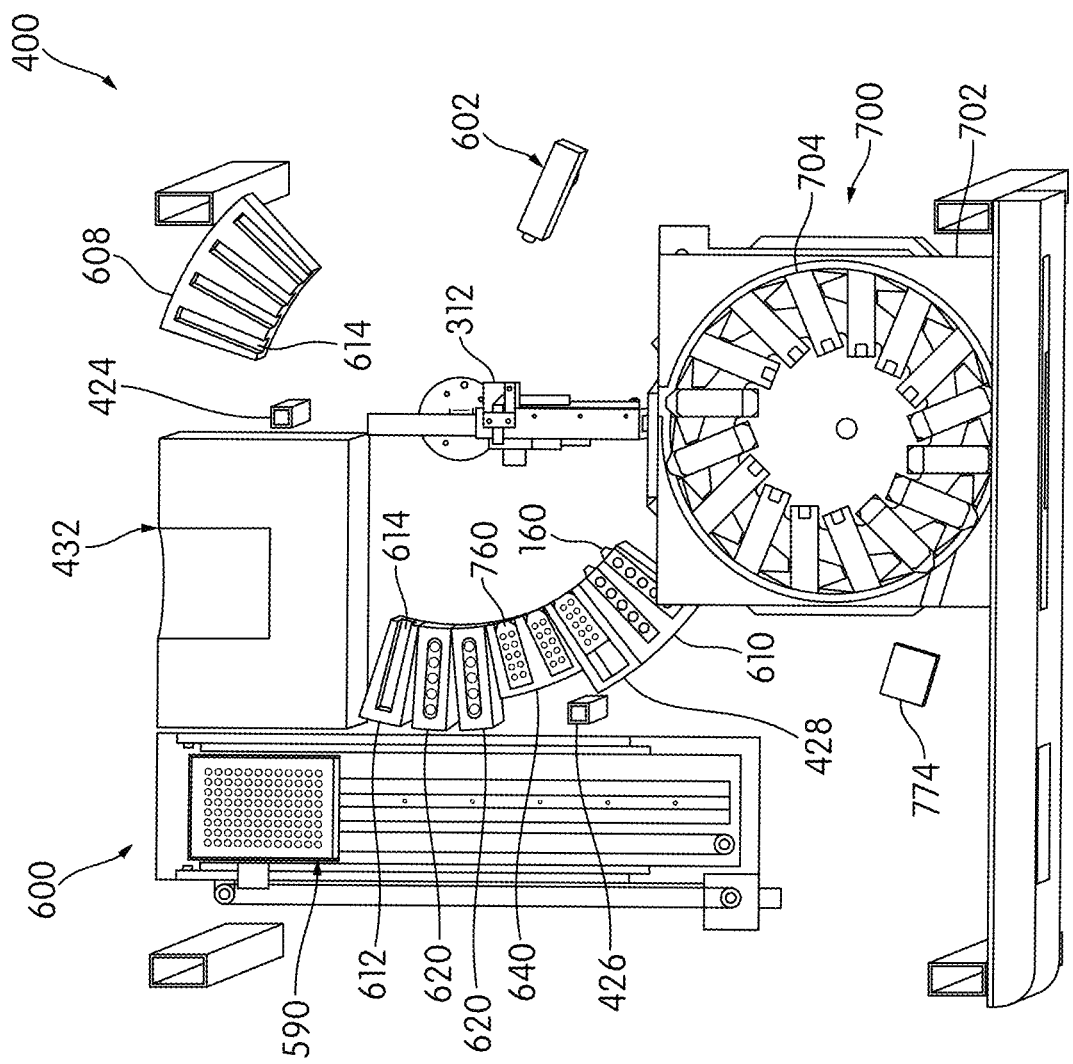
FIG. 14 is a top perspective view of a receptacle processing deck of the processing extension module.

Aspects of the general configuration of the processing extension module 400 are shown in FIGS. 4, 5, 6, and 14. FIG. 4 is a perspective view of a processing extension module 400 embodying aspects of the present disclosure coupled to an analyzer 100. FIG. 5 is a top plan view of the processing extension module 400 separated from the analyzer 100. FIG. 6 is a top plan view of a PCR deck 430 of the processing extension module 400. FIG. 14 is a top plan view of a receptacle processing deck 600 of the processing extension module 400. Referring to FIGS. 4-6 and 14, the component modules of the processing extension module 400 include: a robotic pipettor 402, a thermocycler/signal detector 432, tip drawers 580 (e.g., two or more) configured to contain trays of disposable tips for the pipettor(s), processing vial/cap drawers 440 (e.g., two or more) configured to contain trays of disposable processing vials and associated caps, a reagent bottle drawer 500 and reagent bottle transport 550, a receptacle distribution system comprising a receptacle handoff module 602 and a receptacle distribution module, which, in the exemplary embodiment shown, comprises a rotary distributor 312, MRD storage 608, 610, 612 for MRDs 160, magnetic elution slots 620 (e.g., two or more), a waste bin 652, a centrifuge 588, a reagent card changer 700, reagent card loading stations (e.g., two or more) 640, and a compartment 590 to store accessories, including, for example, consumables, output cards, and/or post-processing vial/cap assemblies.

As shown in FIG. 4, the components may be positioned on different levels, or decks, arranged vertically through the module 400. The robotic pipettor 402 is disposed near the top of the processing extension module 400, above all other components. Below the pipettor robot 402, the PCR deck 430 includes the reagent bottle drawer 500 and reagent bottle transport 520, the centrifuge 588, the top of the thermocycler/signal detector 432, the tip drawers 580, and the processing vial/cap drawers 440. Below the PCR deck 430, the receptacle processing deck 600 includes the receptacle handoff module 602, the rotary distributor 312, the MRD storage 608, 610, 612, the magnetic elution slots 620, the reagent card changer 700, and the reagent card loading stations 640. As can be seen in FIG. 6, the magnetic elution slots 620 and the reagent card loading stations 640 on the receptacle processing deck 600 are accessible by the robotic pipettor 402 through a gap between modules of the PCR deck 430.

The receptacle distribution system, comprising the receptacle handoff module 602 and the rotary distributor 312, is configured to receive a receptacle (e.g., an MRD) from the receptacle transfer apparatus (e.g., the receptacle distributor 150) of the analyzer 100 and transfer the receptacle into the processing extension module 400 and move the receptacle into different positions within the processing extension module 400. The rotary distributor 312 and the receptacle handoff module 602 are shown schematically in FIG. 14. Further details regarding these components are described below.

The processing extension module 400 is operatively positioned adjacent to the analyzer 100, with the reagent bottle transport 550 extending into the analyzer 100 so that elution bottles 502, 504 can be transported by the reagent bottle transport 550 from the elution bottle drawer 500 to a position within the analyzer 100 at which a fluid dispense mechanism, e.g., a pipettor, within the analyzer 100 can access the bottles 502, 504. The processing extension module 400 may be attached to the analyzer 100 by any suitable means including mechanical fasteners (e.g., bolts and/or screws), clamps, or any combination of suitable means. Suitable means for connection of power and/or data lines are provided between the processing module 400 and the analyzer 100.

The processing extension module 400 can be supported with respect to the analyzer 100 such that the processing module-analyzer assembly is not over-constrained. Thus, in some embodiments, it is preferable that the processing extension module 400 does not include any legs or feet that contact the ground beneath the processing module and support some or all of the weight of the module. In certain embodiments, if the processing extension module 400 included its own rigid feet (e.g., two, three, or four feet), then the four feet of the analyzer 100 and the feet of the processing extension module 400 would create an over-constrained geometry. In this case, it would be necessary to carefully level all feet of the processing extension module 400 and the analyzer 100 relative to each other to ensure that the assembly is level and that excessive stresses are not applied to attachment points between the processing extension module 400 and the analyzer 100. To avoid such a potentially over-constrained geometry, the processing extension module 400, in some embodiments, is cantilevered off the analyzer 100 if the analyzer feet can support the additional weight of the processing extension module. In some embodiments, some of the weight of the processing extension module 400 may be supported by a single foot on a far edge of the processing extension module 400 away from the analyzer 100.

The interface between the processing extension module 400 and the analyzer 100 should be blocked and sealed where possible to prevent airflow between the two instruments. Existing air inlets on the side of the analyzer 100 facing the processing extension module 400 may be ducted through the processing extension module 400 to a fresh air source. The side wall of the processing extension module 400 facing the analyzer 100 may be covered by panels to block airflow into the analyzer 100. Such panels will include openings where necessary for receptacle or container transfer between the processing extension module 400 and analyzer 100, cable routing, etc.

Component modules of an exemplary embodiment of the processing extension module 400 are described below.

Reagent Cards

Amplification and other reagents may be provided in the processing extension module 400 in lyophilized form in a reagent card comprising a cartridge that includes wells within which the lyophilized reagent may be reconstituted. The reagent card is further configured to be stored within the processing extension module 400 and to be moved within the processing extension module 400 by the rotary distributor 312, and inserted and removed from the reagent card changer 700.

Figure 19:
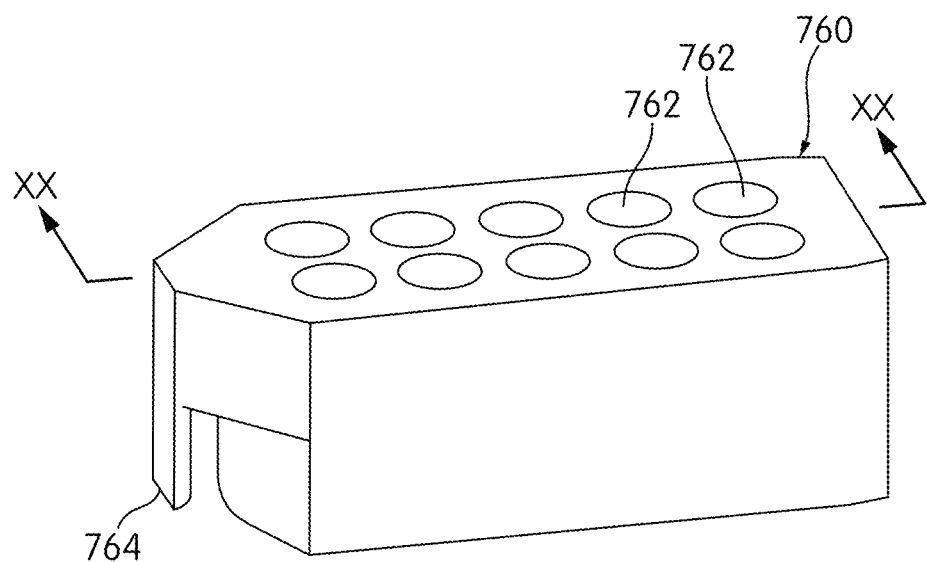
FIG. 19 is a top perspective view of a reagent card embodying aspects of the present disclosure.
Figure 20:
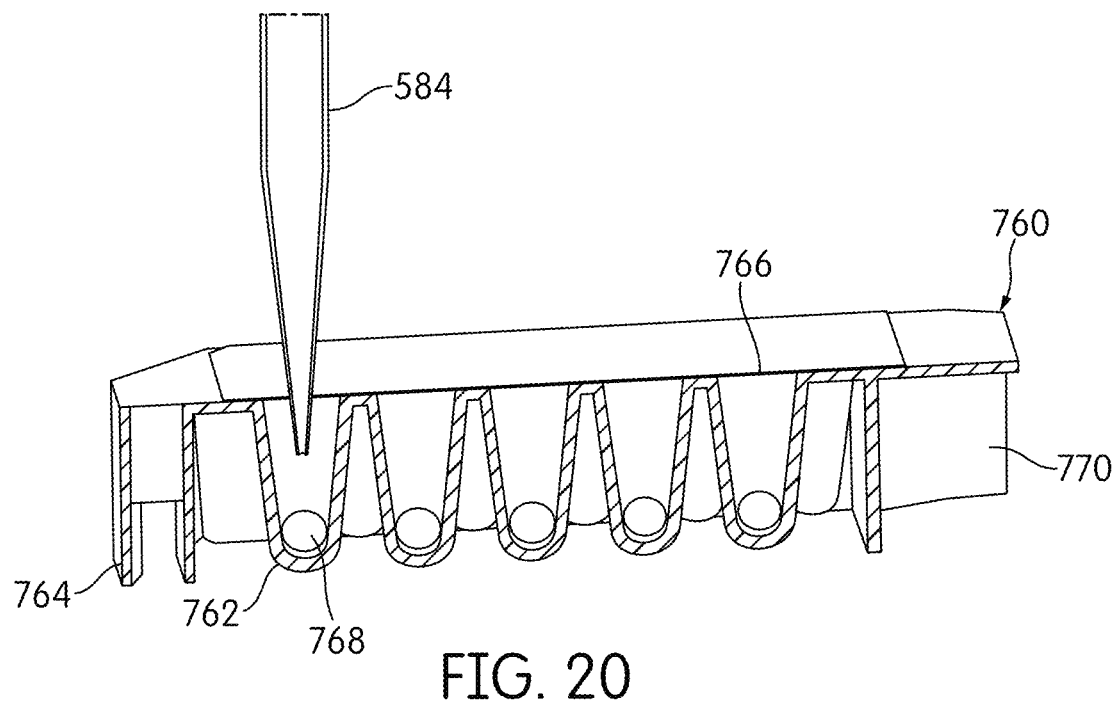
FIG. 20 is a top perspective, cross-sectional view of a reagent card along the line XX-XX in FIG. 19.

Details of a reagent card 760 are shown in FIGS. 19 and 20. The reagent card 760 may include a plurality of mixing wells 762, each of which contains a lyophilized assay-specific reagent 768, which may be in pellet form. In the illustrated embodiment, the reagent card 760 includes ten mixing wells 762, but reagent card 760 may include more or fewer than ten mixing wells. Each mixing well 762 of a single reagent card 760 may hold the same reagent, or the wells 762 may hold different reagents, or some wells 762 may hold the same reagent and some may hold different reagents. Exemplary assay specific reagents 768 held in the reagent card 760 include reagents for performing a single PCR reaction utilizing a sample. Such reagents may be specific for one target nucleic acid or a panel of different target nucleic acids, for example, one or more targets comprising a respiratory panel, including reagents necessary to conduct a PCR assay targeting Flu A, Flu B, RSV, parainfluenza 1, 2, and 3, Human Metapneumovirus, Adenoviris, H1, H3, 2009 H1N1, and/or Tamiflu resistance. In an embodiment, the each reagent pellet 768 is held at the bottom of the associated mixing well 762 with electrostatic force imparted to the pellet 768 and/or the mixing well 762. In other embodiments, the each reagent pellet 768 is held at the bottom of the associated mixing well 762 with one or more physical feature present in the mixing well 762, for example, those described in U.S. Provisional Patent Application 61/782,320, entitled "SYSTEMS, METHODS, AND APPARATUSES FOR PERFORMING AUTOMATED REAGENT-BASED ASSAYS filed Mar. 14, 2013, the disclosure of which is hereby incorporated by reference.

The mixing wells 762 are covered by a pierceable foil 766 adhered to the top of the reagent card 760. Foil 766 can be pierced by a pipette tip 554 to enable reconstitution agents or other substances to be dispensed into the mixing well 762 and to enable reconstituted reagent to be aspirated from the mixing well 762.

Reagent card 760 further includes a manipulating hook 764 that is similar to the manipulating hook 166 of the MRD 160 and is configured to be engageable by a manipulating hook of the rotary distributor 312. The reagent card 760 may include a rear recess 770 that is configured to align the reagent card within a reagent card carrier, as will be described below.

Tip Drawers

As shown in FIGS. 4-6, tip drawers 580 are configured to hold trays 582 of disposable pipettor tips in a manner that enables the tips held in the drawers 580 to be accessed by the robotic pipettor 402. In the illustrated embodiment, the processing extension module 400 includes two tip drawers 580, each constructed and arranged to hold up to three trays 582 of disposable pipettor tips. The drawers 580 may be configured to accept commercially-available trays of disposable pipettor tips. Exemplary, commercially-available pipettor tips and trays are available from TECAN (TECAN U.S. Inc., Research Triangle Park, North Carolina). Such tips are available in a variety of volumetric capacities, and each tip may be conductive to facilitate capacitive liquid level sensing and tip-present detection, as is well known in the art. Exemplary trays hold ninety-six pipettor tips.

The drawers 580 are configured to be pulled out of the processing extension module 400 to enable an operator to place trays 582 of tips into the drawers 580 and to remove empty trays from the drawers 580. A door or cover panel that is either part of each drawer 580 or can be opened to access drawer(s) 580 behind it is preferably provided to present an esthetically pleasing appearance to the front of the processing extension module 400. Manual or automated locks, controlled by the system controller, may be provided to prevent the drawers 580 from being pulled open when the processing extension module 400 is operating and/or visible and/or audible warning signals may be provided to indicate that a drawer 580 is not closed properly.

Robotic Pipettor

Figure 21:
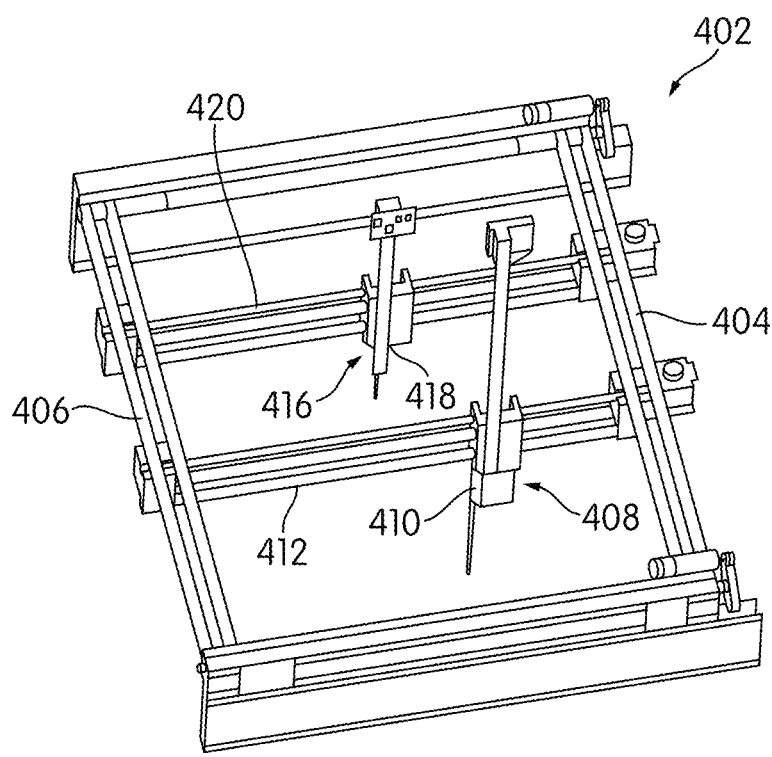
FIG. 21 is a perspective view of a pipettor robot of the processing extension module.
Figure 22:
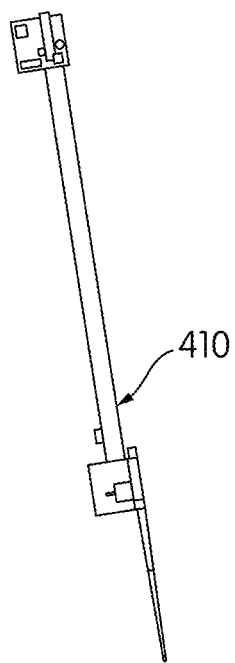
FIG. 22 is a perspective view of a fluid transfer pipettor of the pipettor robot.

The robotic pipettor 402 shown in FIGS. 4, 21, and 22 is a dual arm system comprising a front arm 408 and a back arm 416. Robotic pipettor 402 comprises a substance transfer device of the processing extension module 400 for dispensing and/or aspirating substances into and/or from a container, receptacle, well, etc. In an exemplary embodiment, the front arm 408 includes a fluid transfer pipettor 410 configured to aspirate fluid and dispense fluid and includes an integrated syringe pump, and the back arm 416 includes a vial transfer pipettor 418 and does not perform fluid transfer. The robotic pipettor 402 comprises a Cartesian gantry assembly with two transverse tracks 404, 406, a back arm longitudinal track 420, and a front arm longitudinal track 412. The designations "longitudinal" and "transverse" are merely for distinguishing the two sets of tracks, which may be orthogonal to one another, but otherwise the designations are arbitrary.

The fluid transfer pipettor 410 may be driven back and forth along the front arm longitudinal track 412 by a belt, drive screw, or other motion transmission apparatus coupled to a motor, and the vial transfer pipettor 418 may be driven back and forth along the back arm longitudinal track 420 by a belt, drive screw, or other motion transmission apparatus coupled to a motor. The front arm longitudinal track 412 may be driven back and forth along the transverse tracks 404, 406 by a belt, drive screw, or other motion transmission apparatus coupled to a motor, and the back arm longitudinal track 420 may be driven back and forth along the transverse tracks 404, 406 by a belt, drive screw, or other motion transmission apparatus coupled to a motor. The fluid transfer pipettor 410 and the vial transfer pipettor 418 include probes that are driven along the Z, or vertical, axis, for example, by a motor coupled to the probes, e.g., by a gear, a rack and pinion, a lead screw, or other suitable apparatus. The motors may be under the control of a system controller. The motors may be stepper motors and may include rotary encoders for controlling and monitoring the position of the track or pipettor to which it is coupled. Each of the tracks have home sensors (or limit switches) for indicating when the pipettor 410 or the pipettor 418 is in one or more designated positions, such as a designated "home" position. Similarly, each pipettor may have a vertical home sensor for indicating when the probe is in one or more designated vertical positions, such as a designated vertical "home" position. Such sensors for indicating a home position may include optical sensors (e.g., slotted optical sensors), proximity sensors, magnetic sensors, capacitive sensors, etc.

In one exemplary embodiment, the fluid transfer pipettor 410 is configured to accept TECAN 1 ml disposable pipettor tips by inserting the probe thereof into a disposable pipettor tip, and an interference fit between the probe and the pipettor tip frictionally secures the pipettor tip to the end of the probe. The front arm 408 and the fluid transfer pipettor 410 are configured to access at least parts of both the PCR deck 430 and the receptacle processing deck 600 on the processing extension module 400. The fluid transfer pipettor 410 may include integrated tip sensing for confirming the presence or absence of a disposable pipette tip, capacitive level sensing for detecting contact by the pipette tip with the surface of the fluid contents of a reaction receptacle or other container and determining the level of the fluid contents based on the detected vertical position of the pipettor, and pressure sensing for sensing pressure fluctuations within the fluid transfer system during fluid dispensing or aspiration. The fluid transfer pipettor 410 is capable of transferring fluids, caps, or cap/processing vial assemblies such as those described below.

The vial transfer pipettor 418 is a "pick and place" device configured pick up a vial/cap assembly by inserting the probe thereof into a cap that is coupled to a vial, as will be described below.

Pipettor Pump

In an exemplary embodiment, the pump for the fluid transfer pipettor comprises a ceramic piston driven by a servomotor and a leadscrew. The servomotor is controlled by the system controller, and the apparatus preferably includes rotary encoder feedback to the system controller and home sensors for monitoring the position of the piston. The syringe may have a volume of between 0.5 and 3 ml (preferably 1.05 ml) and is preferably made from ceramic. The pump can preferably dispense very small volumes (5 µl) of fluid with +/−5% CV measured across 30 discrete dispenses. To achieve this performance, the pump includes a solenoid valve to release pressure at the end of the stroke to ensure consistent fluid shear.

Processing Vial/Cap Assembly

In general, the processing vial provides a receptacle for containing reaction fluids for performing PCR, or other process. The cap is configured to be placed into or onto the vial in an automated manner so as to close off the vial. The cap is configured to receive the end of a pipettor probe with a friction fit, so that the pipettor can thereafter pick up the cap and place it into or onto the vial. The cap and vial are configured to lock together so that, once the cap is placed into or onto the vial, the cap and the vial are interlocked so that the pipettor, with its probe inserted into the cap, can then pick up both the cap and the vial that is locked to the cap. The pipettor can then transfer the vial and cap from one location within the processing extension module 400 to another location. Exemplary caps and processing vials are provided, for example, in U.S. Provisional Patent Application 61/782,320, entitled "SYSTEMS, METHODS, AND APPARATUSES FOR PERFORMING AUTOMATED REAGENT-BASED ASSAYS filed Mar. 14, 2013, the disclosure of which was incorporated above.

Details of an exemplary embodiment of the processing vial 464, the processing vial cap 476, and the pipettor probe 422 are shown in FIGS. 23-26.

Figure 23:
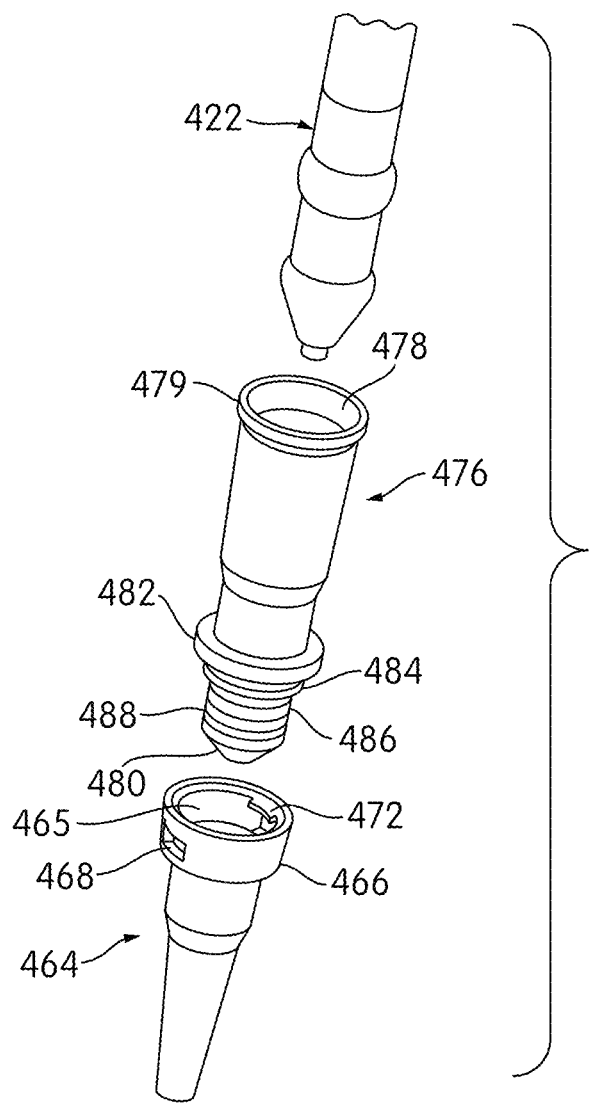
FIG. 23 is an exploded, perspective view of a Processing vial, a processing vial cap, and a pipettor probe.
Figure 24:
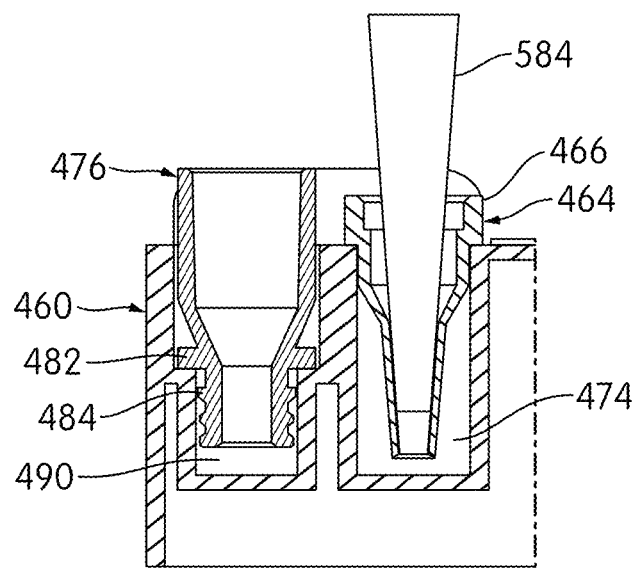
FIG. 24 is a transverse cross section of the processing vial and the processing vial cap disposed within a processing vial well and a cap well, respectively, of a processing vial/cap drawer tray.
Figure 25:
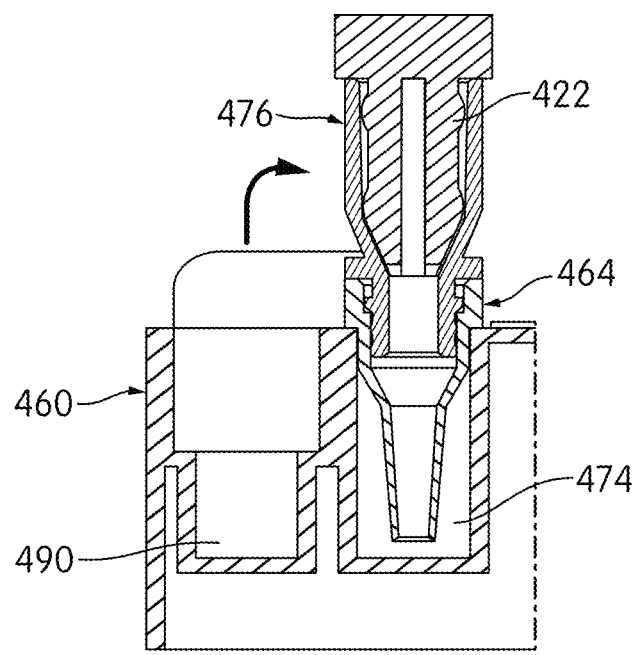
FIG. 25 is a transverse cross section of the processing vial cap removed from the cap well and inserted into the processing vial with the processing vial disposed within the processing vial well.

In the embodiment shown in FIGS. 23-25, the processing vial 464 may have a conical shape and an open top end 465 surrounded by a locking collar 466. Lateral through holes 468 are formed through the locking collar 466 at diametrically opposed locations. A latch hook 472 is located above each through hole 468.

The processing vial cap 476 has an open top end 478 and a closed lower end 480. An annular collar 482 extends about the cap 476 at a position between the top end 478 and lower end 480. Collar 482 the vial 476 sits atop the thermocycler when the vial 476 is placed therein, ensuring a close fit of the vial within the wells of the thermocycler. A lower portion of the cap 476 beneath the collar 482 defines a plug that fits into the open top end 465 of the processing vial 464. This plug is sized so as to fit into the processing vial 464 with an interference, friction fit. A latch collar 484 extends about the cap 476 at a position below the collar 482. Seal rings 486, 488 extend about the cap 476 at positions below the latch collar 484.

FIGS. 24 and 25 show in cross section, a processing vial cap 464, initially held in a cap well 490 of a vial/cap tray 460, and a processing vial 464 held in a vial well 474 of the vial/cap tray 460. After fluids are dispensed into the processing vial 464 with the disposable pipette tip 584 (connected to a pipettor), the processing vial 464 is capped by a processing vial cap 476 by inserting the closed lower end 480 of the cap 476 into the open top end 465 of the vial 464, until a bottom surface of the collar 482 of the cap 476 abuts a top surface of the locking collar 466 of the vial 464. The latch collar 484 of the cap 476 snaps in beneath the latch hooks 472 of the vial 464 to secure the cap 476 to the vial 464. The cap 476 and the vial 464 are thereafter locked together and the cap/vial assembly may be picked up and moved by the pipettor. The cap/vial assembly can be removed from the pipettor probe 422 by an eject apparatus engaging a rim 479 surrounding open end 478 to pull the cap/vial assembly off the pipettor probe 422. The seal rings 486, 488 of the cap 476 preferably have outer diameters that are slightly larger than the inner diameter of the upper portion of the vial 464, thereby forming a tight seal between the cap 476 and the vial 464 as the cap and vial are made of materials, such as suitable plastics, that are at least partially resilient.

Figure 26:
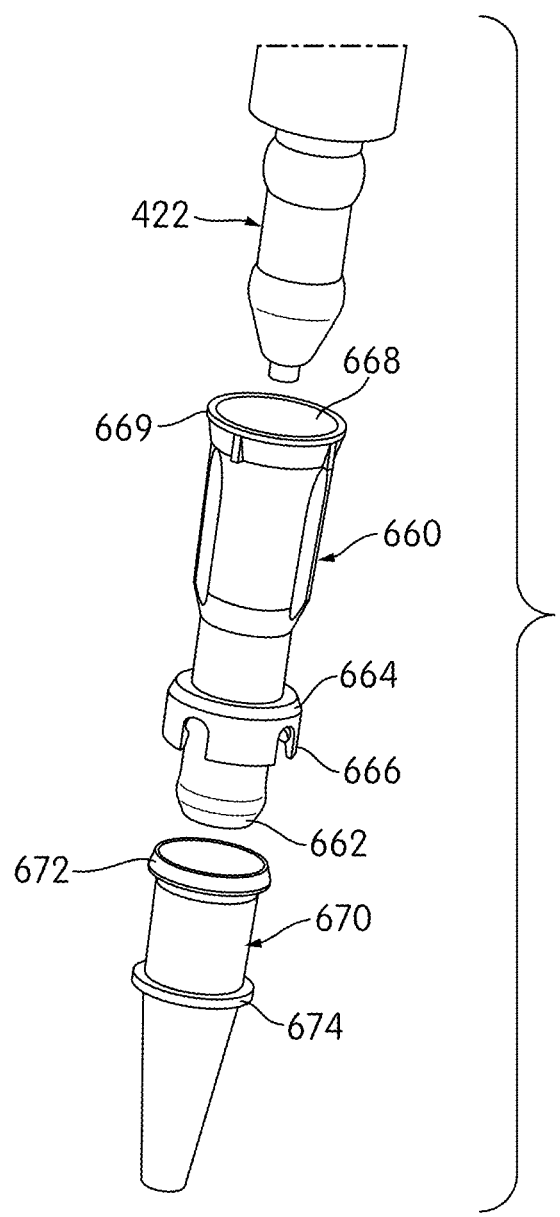
FIG. 26 is an exploded, perspective view of an alternative embodiment of a processing vial, a processing vial cap, and a pipettor probe.

An alternative processing vial/cap assembly is shown in FIG. 26, which is an exploded perspective view of a processing vial 670 and a processing vial cap 660. Processing vial cap 660 includes closed lower end 662, a tapered opening 668, and a latch collar 664 having latch fingers 666. The vial 670 includes a lock collar 672 surrounding the open top end of the cap 670 and a collar 674. Collar 674 the vial 670 sits atop the thermocycler when the vial 670 is placed therein, ensuring a close fit of the vial within the wells of the thermocycler. After fluid is dispensed into the vial 670, the vial is capped by first inserting the pipettor probe 422 into the tapered opening 668 of the processing vial cap 660 to frictionally secure the cap 660 to the pipettor probe 422 and then picking up the cap 660 with the pipettor and inserting the closed lower end 662 of the cap 660 into the open top end of the vial 670 until the latch fingers 666 lockingly snap onto the lock collar 672 of the vial 670. The cap 660 and the vial 670 are thereafter locked together and the cap/vial assembly may be picked up and moved by the pipettor. The cap/vial assembly can be removed from the pipettor probe 422 by an eject apparatus engaging a rim 669 surrounding opening 668 to pull the cap/vial assembly off the pipettor probe 422.

The processing extension module 400 may include "vial present" sensors. The vial present senor is used as a process control measure to verify that a vial is attached to the cap. The fluid transfer pipettor 410 (front arm 408) and the vial transfer pipettor 418 (back arm 416) will detect when a cap is attached to the arm. One means by which fluid transfer pipettor 410 or the vial transfer pipettor 418 will detect when a cap is present is by means of strip sleeve on the pipettor probe 422. When the cap is picked by the pipettor probe, the upper rim of the cap pushes on and raises the sleeve (e.g. a few millimeters), and this movement may be detected by a sensor. However, pipettors often cannot detect if a vial is attached to the cap. In one exemplary embodiment, the vial present sensor is an optical sensor (or multiple sensors) that either arm 408, 416 can move past/through as it transports a capped vial into or out of the centrifuge 588. The vial present sensor will trigger on the vial (if present) as the arm moves past the sensor.

Reagent Bottle Drawer and Reagent Bottle Transport

In one exemplary embodiment, the reagent bottle drawer 500 holds two elution buffer bottles, two oil bottles, and four reconstitution fluid bottles. The reagent bottle drawer 500 may be opened by an operator to load bottles. Once closed, the reagent bottle transport 550 moves the elution buffer bottles into the analyzer 100 to a location in which a fluid transfer mechanism, such as a pipettor, can access the bottles. The oil bottles and the reconstitution fluid bottles remain in the reagent bottle drawer 500, where they are accessed by the fluid transfer pipettor 410.

Bottles carried on the reagent bottle drawer 500 may be identified by machine-readable code, such as RFID. An indicator panel 507 having visible (e.g., red and green LEDs) and/or audible indicators provides feedback to the operator regarding bottle status.

The reagent bottle drawer 500 and reagent bottle transport 550 are shown in FIGS. 5-10. The reagent bottle drawer 500 is located in the PCR deck 430 adjacent the tip drawers 580 and may be accessed from the front of the processing extension module 400. The reagent bottle drawer 500 may be pulled out to enable an operator to place two bottles 502, 504 containing an elution buffer as well as a number of bottles, or other types of fluid container, containing other reagents, such as, for example, oil or reconstitution buffer, into the drawer 500. The number of bottles accommodated by the drawer 500 is dictated by considerations of intended throughput and desired time period between required re-stocking of supplies A door or cover panel, which is either part of the reagent bottle drawer 500 or can be opened to access the reagent bottle drawer 500 behind it, may be provided to present an esthetically pleasing appearance to the front of the processing extension module 400. Automated locks, controlled by the system controller, may be provided to prevent the reagent bottle drawer 500 from being pulled open when the processing extension module 400 is operating, and/or visible and/or audible warning signals may be provided to indicate that the reagent bottle drawer 500 is not closed properly.

When the reagent bottle drawer 500 is closed, the bottles 502, 504 are moved to the far end of the drawer 500, where they are positioned in operative engagement with the reagent bottle transport 550 extending laterally from an end of the drawer 500 into the analyzer 100. Upon closing the reagent bottle drawer 500, the reagent bottle transport 550 is activated to move the bottles 502, 504 into the analyzer 100 to a position at which a pipettor can access the bottles 502, 504. The reagent bottle transport 550 may be activated manually by a user (e.g., pressing a button or switch) or automatically by the system controller upon receipt of an input signal indicating that the reagent bottle drawer 500 has been fully closed, thereby placing the bottles 502, 504 into operative position with respect to the reagent bottle transport 550.

Figure 9:
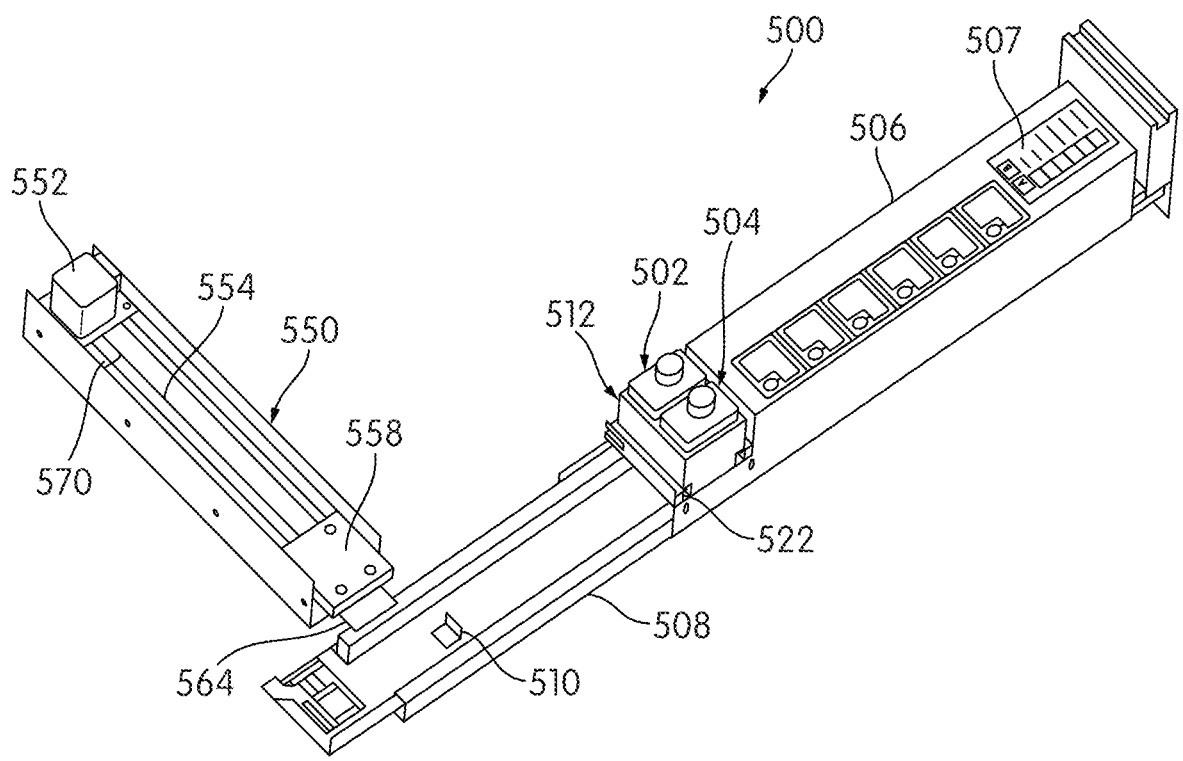
FIG. 9 is a top perspective view of the reagent bottle drawer and reagent bottle transport of the processing extension module, with the reagent bottle drawer in an open position.
Figure 10:
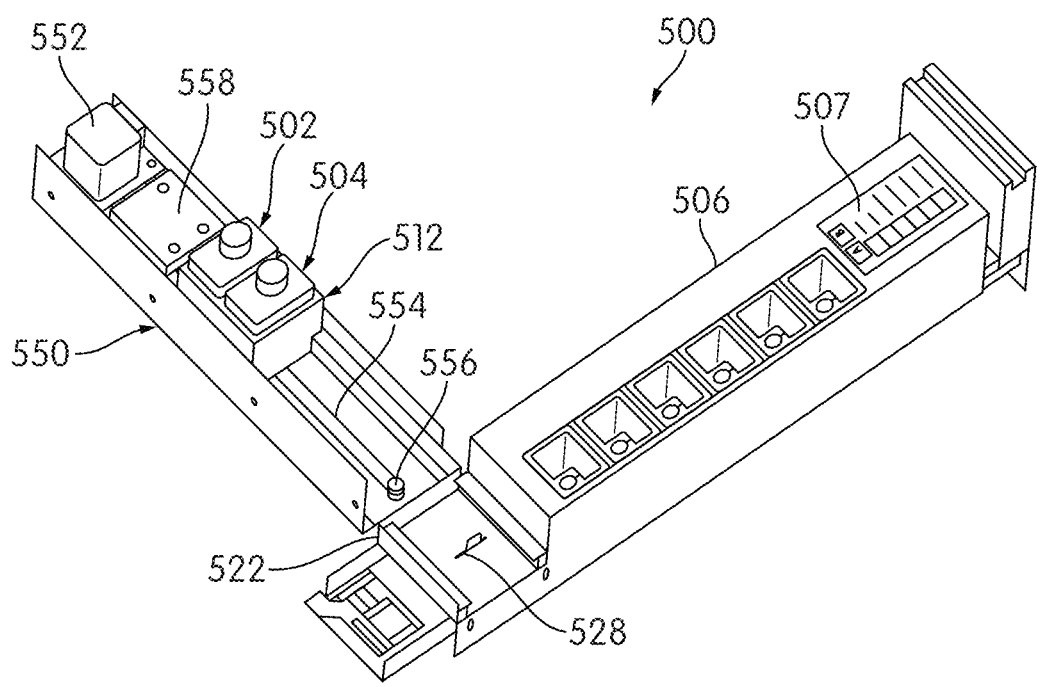
FIG. 10 is a top perspective view of the reagent bottle drawer and reagent bottle transport of the processing extension module, with the reagent bottle drawer in a closed position and elution bottles transported to an end of the of the reagent bottle transport.

Details of the reagent bottle drawer 500 are shown in FIGS. 9-13. The reagent bottle drawer 500 includes a bottle tray 506, configured to hold the plurality of reagent bottles, and a container carriage 512 disposed at the end of the bottle tray 506 and configured to carry elution reagent bottles 502, 504. The bottle tray 506 and the container carriage 512 are moveable along a track 508 between a withdrawn position as shown in FIG. 9 (see also FIG. 7) and a closed position as shown in FIG. 10 (see also FIG. 8).

Figure 11:
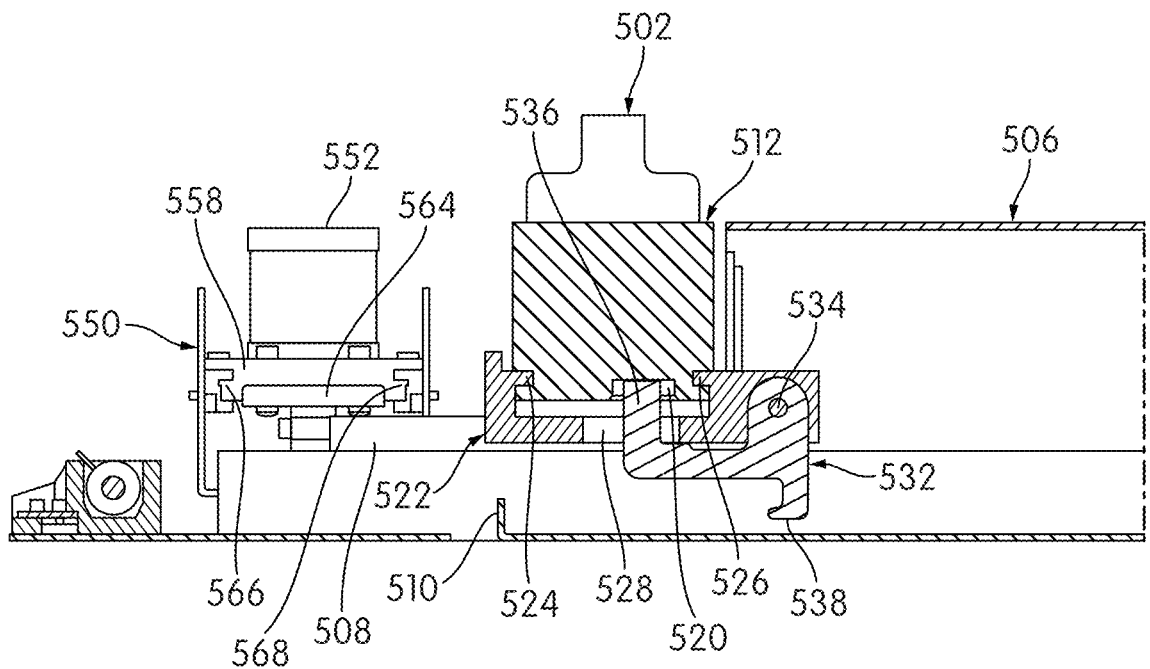
FIG. 11 is a partial cross-sectional view of reagent bottle drawer, with the reagent bottle drawer in an open position.
Figure 12:
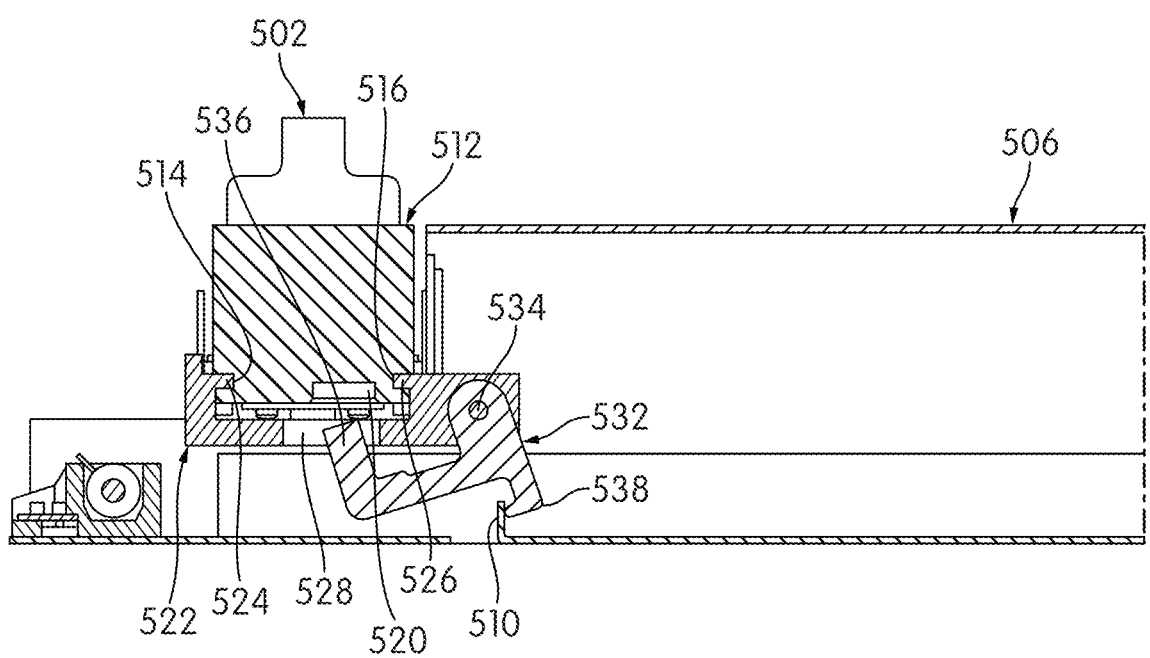
FIG. 12 is a partial cross-sectional view of reagent bottle drawer and the reagent bottle transport, with the reagent bottle drawer in a closed position.

The container carriage 512 is carried on a carriage transport 522 configured to be movable with the bottle tray 506 along the track 508. As shown in FIGS. 11 and 12, the carriage transport 522 includes horizontal carriage rails 524 and 526 that engage rail slots 514, 516, respectively, formed in the container carriage 512 to retain the container carriage 512 within the carriage transport 522.

Figure 7:
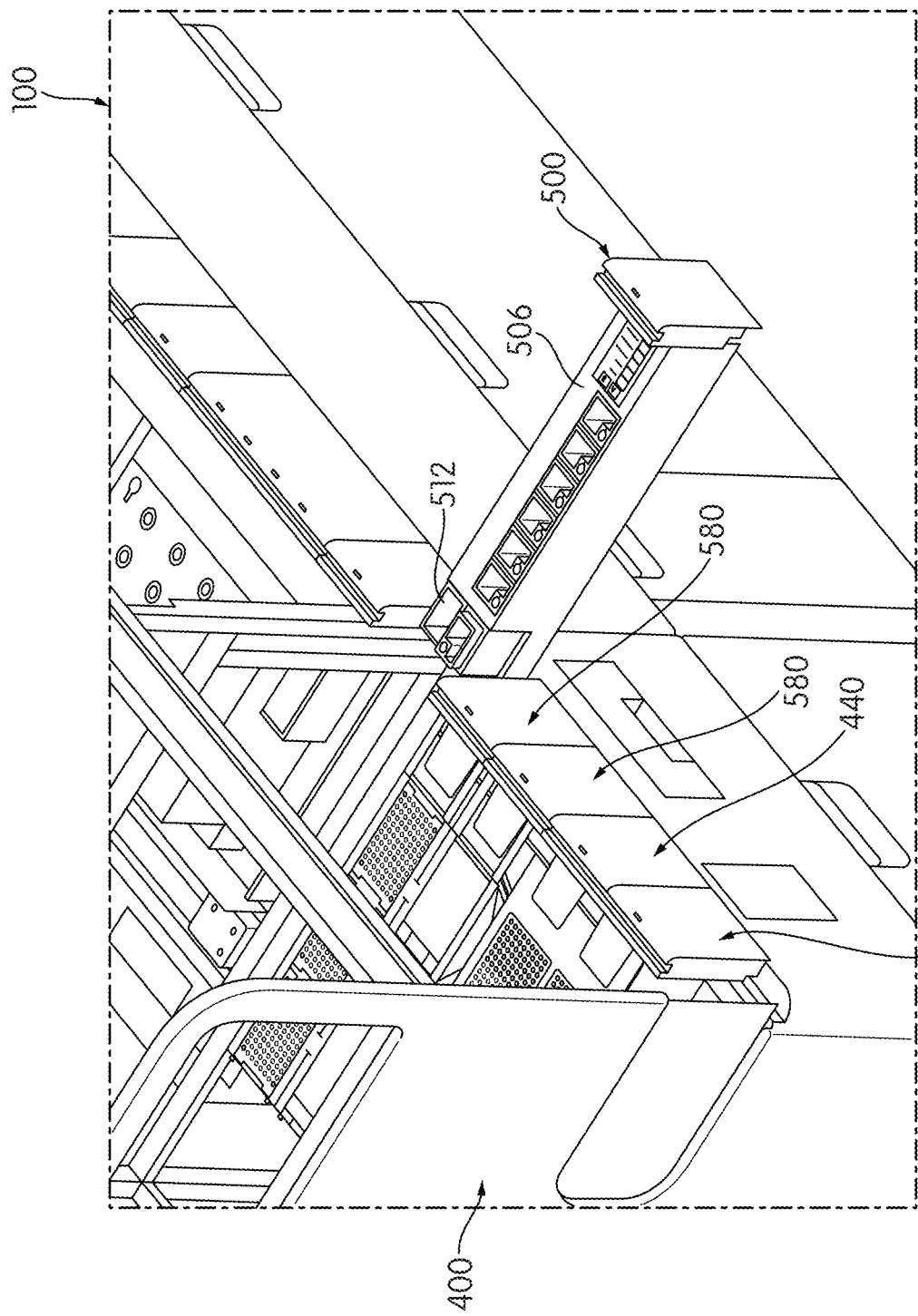
FIG. 7 is a partial, front perspective view of the processing extension module with a reagent bottle drawer in an open position.
Figure 8:
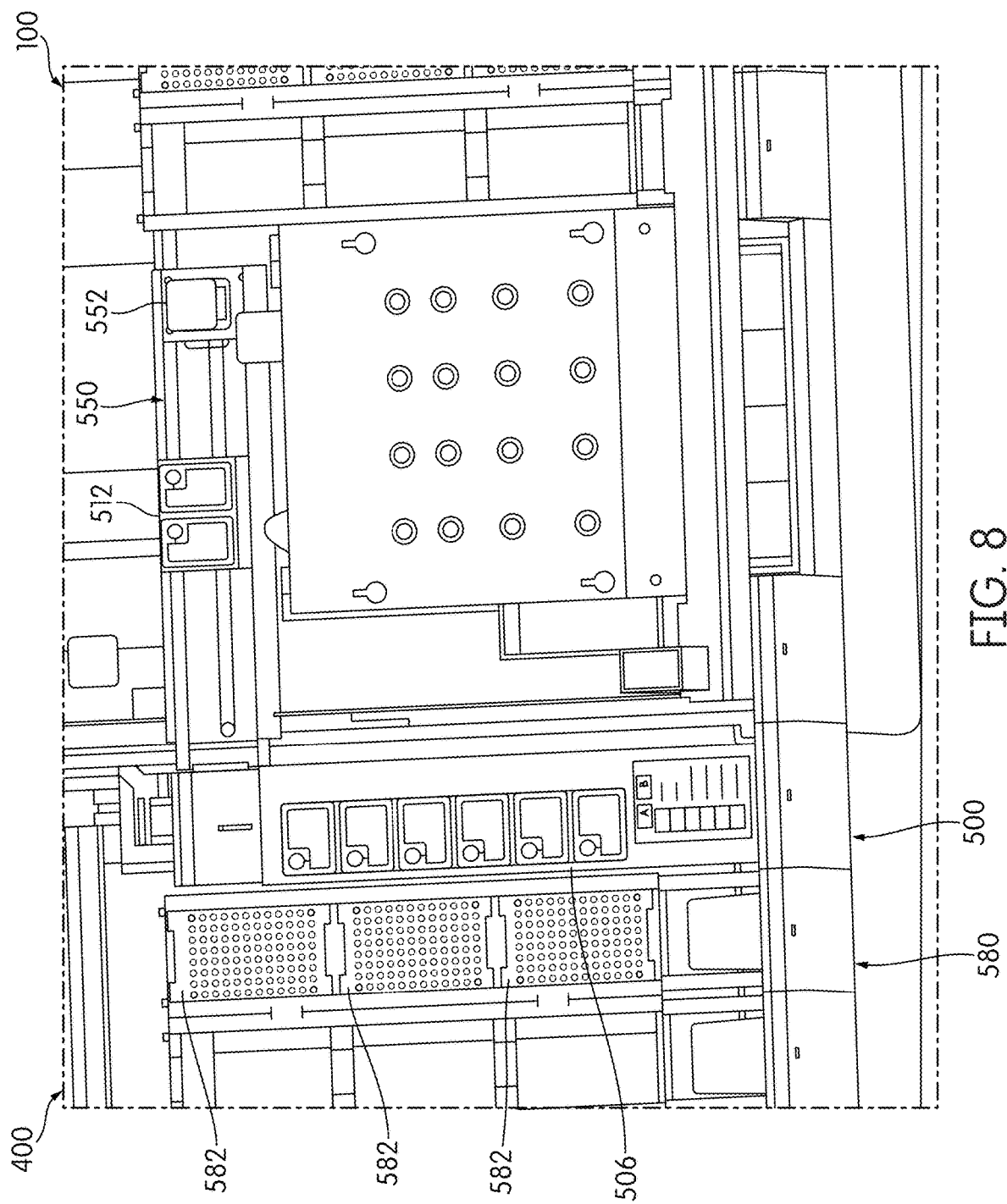
FIG. 8 is a partial, top plan view of the processing extension module and analyzer showing the reagent bottle drawer in a closed position.

The reagent bottle drawer 500 is constructed and arranged to permit operator to place reagent bottles 502, 504 within the container carriage 512 when the drawer is in the open position, as shown in FIGS. 7 and 9. Upon closing the drawer, to the position shown in FIGS. 8 and 10, the reagent container carriage 512 is released from the carriage transport 522 and engaged by the reagent bottle transport 550 to pull the carriage 512 to a lateral position with respect to the track 508 of the bottle tray 506, as shown in 10.

More particularly, the carriage transport 522 moves along the track 508 as the bottle tray 506 is moved into the open or closed positions. As shown in FIG. 11, the carriage transport 522 includes a pivoting carriage lock 532 configured to pivot about pivot pin 534 and including a locking leg 536 that extends upwardly through an opening 528 formed in the bottom of the carriage transport 522 and into a lock recess 520 formed in the bottom of the container carriage 512. A trigger leg 538 extends below the carriage transport 522. As the bottle tray 506 is moved into the closed position (to the left in FIG. 11) the trigger leg 538 of the pivoting carriage lock 532 engages a lock trigger 510 projecting upwardly from the track 508, thereby causing the carriage lock 532 to pivot counterclockwise, as shown in FIG. 12, to withdraw the end of the locking leg 536 from the lock recess 520 of the container carriage 512. With the trigger leg 538 withdrawn from the lock recess 520, the container carriage 512 and the bottles 502, 504 carried therein, are able to slide laterally out of the carriage transport 522 and onto the reagent bottle transport 550.

Figure 13:
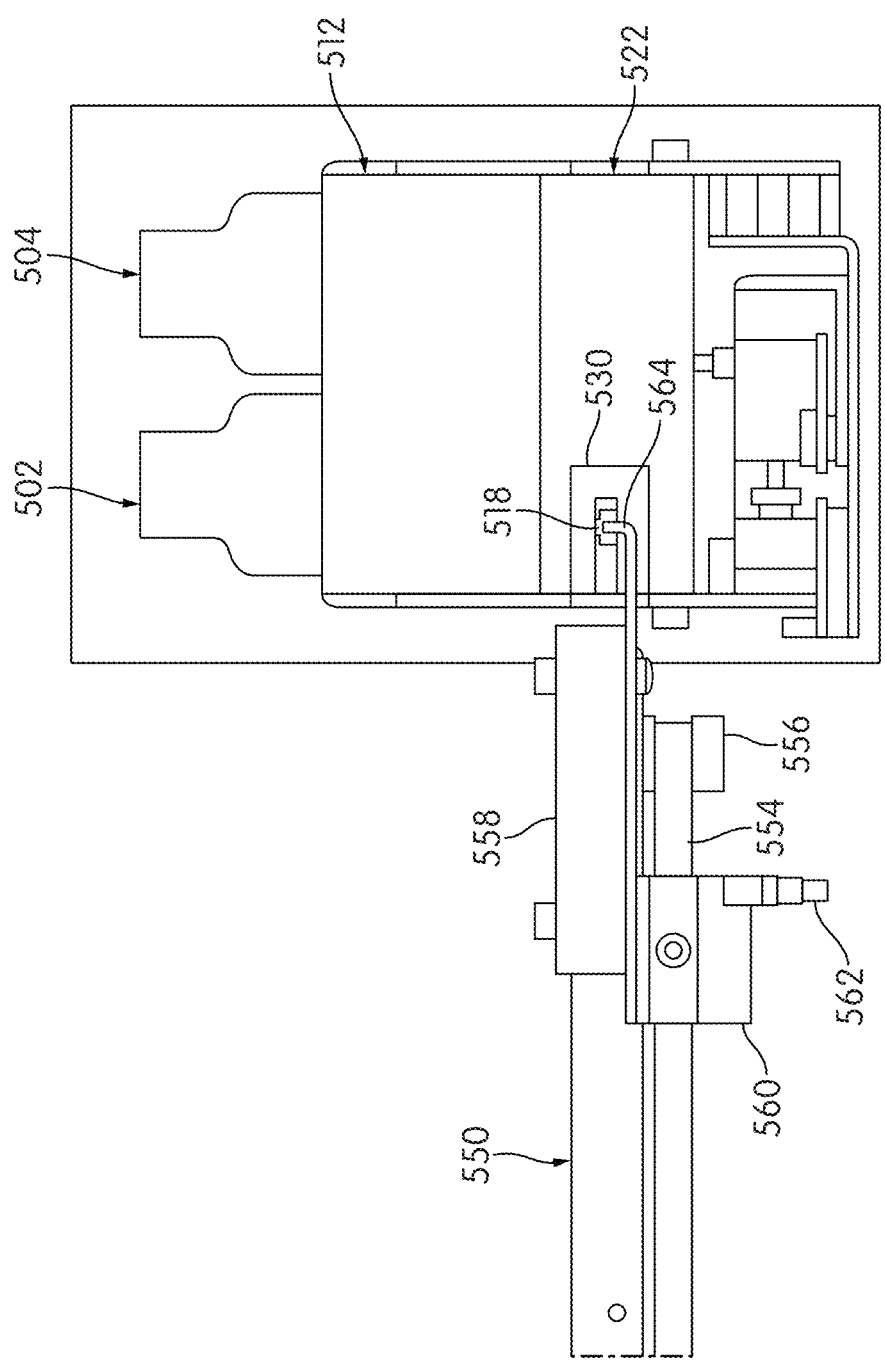
FIG. 13 is a partial end view of reagent bottle drawer, with the reagent bottle drawer in a closed position.

The reagent bottle transport 550 includes a powered carriage transport mechanism for moving the carriage 512 and bottles 502, 504. In one exemplary embodiment, as shown in FIGS. 9, 10, and 13, the carriage transport comprises motor 552 and a continuous belt 554 disposed over the output shaft of the motor and an idler wheel 556 located on an opposite end of the bottle transport 550 from the motor 552. Motor 552 may comprise a stepper motor and may include a rotary encoder for monitoring and controlling, via control signals and feedback data, the position of the motor.

The carriage transport mechanism further includes a sled 558 with a carriage hook 564 extending therefrom. The belt 554 is attached to a portion of the sled 558 so that movement of the belt by the motor 552 causes a corresponding translation of the sled 558 in one direction or the other along the transport 550.

As shown in FIGS. 12 and 13, as the bottle tray 506 is moved to a closed position in which the trigger leg 538 of the pivoting carriage lock 532 engages the lock trigger 510 to withdraw the locking leg 536 from the lock recess 520, the carriage hook 564 passes into a carriage hook slot 530 formed in the carriage transport 522 and engages a hook catch 518 formed in the container carriage 512. The sled 558 and carriage hook 564 may then be translated laterally along the bottle transport 550 by the belt 554 to pull the carriage 512 off of the carriage transport 522 and onto the reagent bottle transport 550. As shown in FIG. 11, the reagent bottle transport includes carriage rails 566, 568 that will engage the rail slots 514, 516, respectively, of the container carriage 512 as the container carriage 512 is pulled onto the reagent bottle transport 550.

As shown in FIG. 13, a home flag 560 projects from the sled 558 and engages a slotted optical sensor 562 to indicate that the sled 558 and the carriage hook 564 are in the fully-extended position shown in FIG. 13. A second slotted optical sensor 570 is provided closer to the motor 552 (see FIG. 9). The second optical sensor 570 is engaged by the home flag 560 when the sled 558 and hook 564 are in the fully retracted position, as shown in FIG. 9. Signals from the sensors 562, 570 are communicated to a system controller to monitor the position of the sled 558. Alternatively, the reagent bottle transport 550 may include limit switches (e.g., contact switches) to stop operation movement of the sled 558 at the fully extended and/or fully retracted positions, for example, by generating stop signals communicated to a controller which then sends stop commands or terminates power to the motor 552. Still other types of sensors may be used for indicating extended and retracted stop positions, including proximity sensors, magnetic sensors, capacitive sensors, etc.

Thermocycler/Signal Detector

An exemplary embodiment of a thermocycler 432 is described in U.S. Provisional Patent Application 61/677,976 Jul. 31, 2012, and U.S. Provisional Patent Application 61/783,952, filed Mar. 14, 2013, entitled "SYSTEM, METHOD, AND APPARATUS FOR AUTOMATED INCUBATION", the contents of each of which are hereby incorporated by reference. An exemplary embodiment of a signal detector 432 is described in U.S. Provisional Patent Application 61/782,340 filed Mar. 14, 2013, the contents of which are hereby incorporated by reference.

Centrifuge

As shown in FIGS. 4, 5, 6, the centrifuge 588 is located on the PCR deck 430 of the processing extension module 400. In one exemplary embodiment, the centrifuge 588 will centrifuge one or more (up to five in one embodiment) capped processing vials 464, 670 at a time. In an exemplary embodiment, each vial is centrifuged prior to PCR to ensure that sample material is located primarily in the bottom of the processing vial 464, 670 and to remove any air bubbles from the contents of the vial 464, 670, which can affect heat transfer and optical transmission quality. The fluid transfer pipettor 410 of the front arm 408 places the capped vial 464, 670 into the centrifuge 588 at an access port indicated at reference number 589. After centrifuging is complete, the vial transfer pipettor 418 of the back arm 416 removes the vial 464, 670 from the centrifuge 588 from an access port indicated at reference number 587 and places it in the thermocycler 432. In an embodiment, the centrifuge configuration (e.g., by providing separate ports 587, 589) allows the fluid transfer pipettor 410 (front arm 408) and the vial transfer pipettor 418 (back arm 416) to load/unload vials simultaneously without colliding with each other. As such, in one embodiment, the centrifuge not only performs its function of providing centrifugation of loaded vials, but also provides a vial transport mechanism by transporting vials from a position 589 accessible to the fluid transfer pipettor 410 to a position 587 where the vials are accessible to the vial transfer pipettor 418. In certain embodiments the fluid transfer pipettor 410 is unable to access position 587 and the vial transfer pipettor 418 is unable to access position 589.

In addition, the centrifuge 588 may incorporate means for tracking the position(s) of the loaded vial(s) within the centrifuge and determine when a vial is positioned at either access port 587, 589. For example, a turntable or other rotating structure on which the loaded vial(s) is(are) centrifuged may be driven by a stepper motor that may include a rotary encoder for precise movement of the turntable and tracking motor counts and/or the turntable or rotating structure may include a rotational position indicator, such as a home flag sensor, constructed and arranged to indicate one or more rotational positions or reference points.

In one exemplary embodiment, the maximum revolution speed of the centrifuge is 3000 revolutions per minute, but other revolution speeds are contemplated based on, inter alia, the composition of the solution being centrifuged and the time period required to provide adequate centrifugation.

Receptacle Distribution Module/Rotary Distributor

In one embodiment, the receptacle distribution module, which is constructed and arranged to move a receptacle onto the receptacle distribution module at a first location on the processing module, carry the receptacle from the first location to a second location on the processing module that is different from the first location, and move the receptacle off the receptacle distribution module at the second location on the processing module, comprises a rotary distributor. In an exemplary embodiment, the rotary distributor of the receptacle distribution system does not constitute a robotic pipettor, such as robotic pipettor 402 described above, or other substance transfer device comprising a pipettor that is supported on a structure for automatically moving the pipettor in different Cartesian directions, such a x-y-z, but is a 3-axis robot designed to transport MRDs 160 and PCR reagent cards 760 between different processing modules of the processing extension module 400. In one exemplary embodiment, rotary distributor 312 works by a hook & rail system in which an extendible and retractable hook pulls or pushes MRDs 160 or reagent cards 760 into or from a distributor head of the rotary distributor 312. Within the distributor head, the MRD 160 or reagent card 760 is supported and guided by rail and wall features within the head. The rotary position of the distributor head is controlled and monitored by a rotary encoder on the motor for position feedback and has a home sensor. The distributor hook may be belt driven with home and end of travel sensors (e.g., slotted optical sensors, limit switches, etc.) The rotary distributor 312 is also constructed and arranged for powered, vertical (or Z-axis) motion of the distributor head for vertical translation of an MRD 160 or reagent card 760. In one exemplary embodiment, the rotary distributor 312 is configured to allow for at least 100 mm of Z-axis travel. The distributor head may include an MRD/reagent card presence sensor in the head. In one exemplary embodiment, the rotary distributor is configured to transfer an MRD 160 between any two modules of the processing extension module 400 within 4 seconds. In certain embodiments, each axis can make a full travel move in approximately 1 second.

Figure 27:
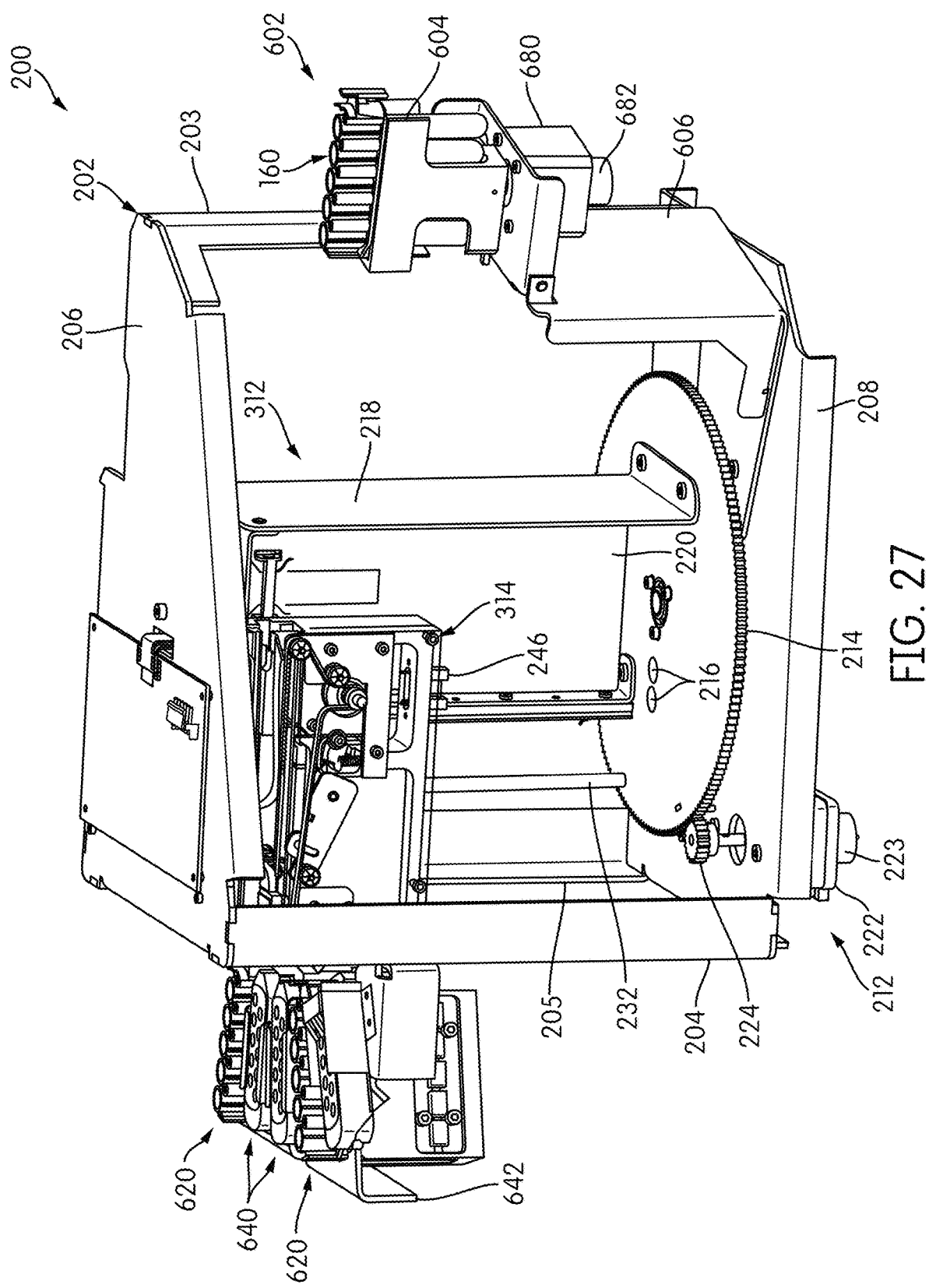
FIG. 27 is a top perspective view of an embodiment of a receptacle distribution system of the processing extension module.
Figure 28:
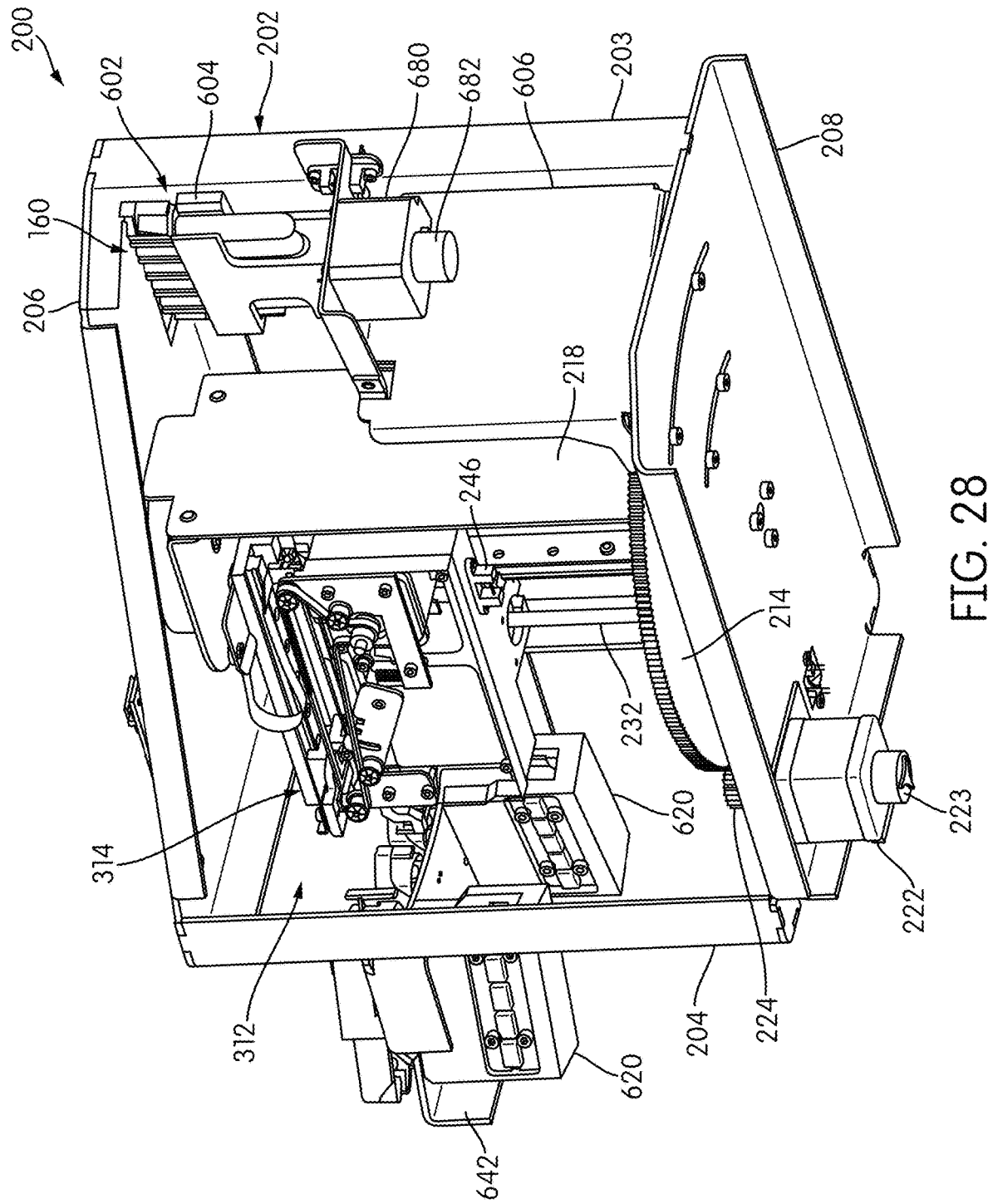
FIG. 28 is a bottom perspective view of the receptacle distribution system.

Details of a receptacle distribution system are shown in FIGS. 27 and 28. In the illustrated embodiment, a receptacle distribution system 200 includes a frame 202 comprising legs 203, 204 and 205 extending between a bottom panel 208 and a top panel 206. The receptacle handoff station 602 is mounted on a handoff station bracket 606 attached to the bottom panel 208 of frame 202 and will be discussed further below. Magnetic elution slots 620 and reagent card loading stations 640 are supported on a bracket 642 attached to legs 204, and 205 of frame 202 and will be discussed further below. A rotary distributor 312 is supported on a first upright wall 218 and a second upright wall 220 within the frame 202.

Figure 29:
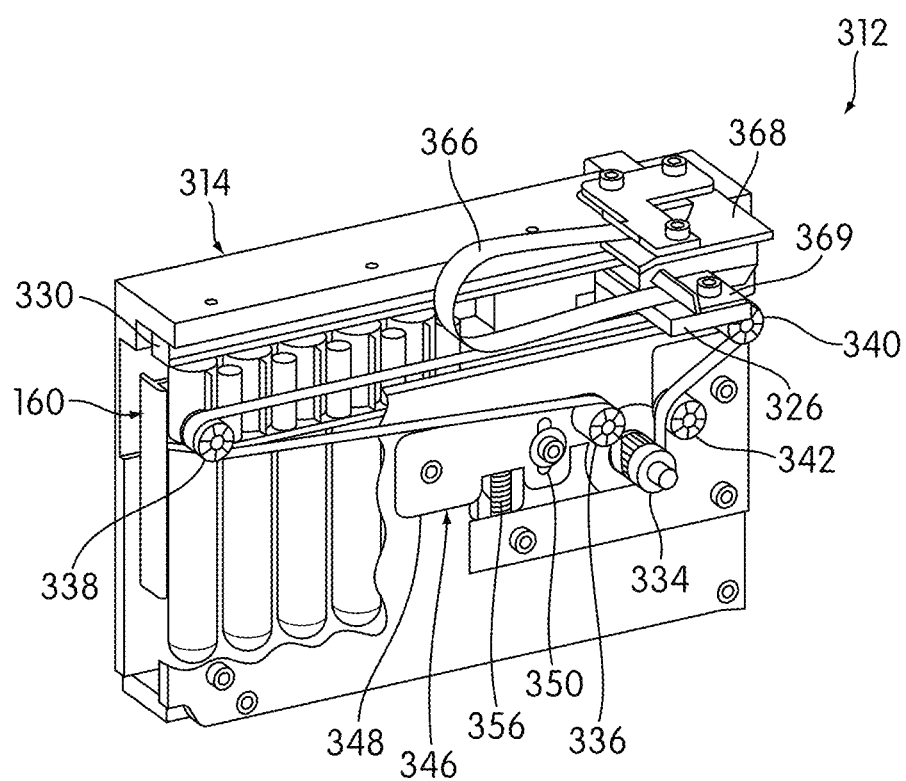
FIG. 29 is a perspective view of an embodiment of a distributor head of a rotary distributor of the receptacle distribution system with a receptacle hook in a retracted position.
Figure 30:
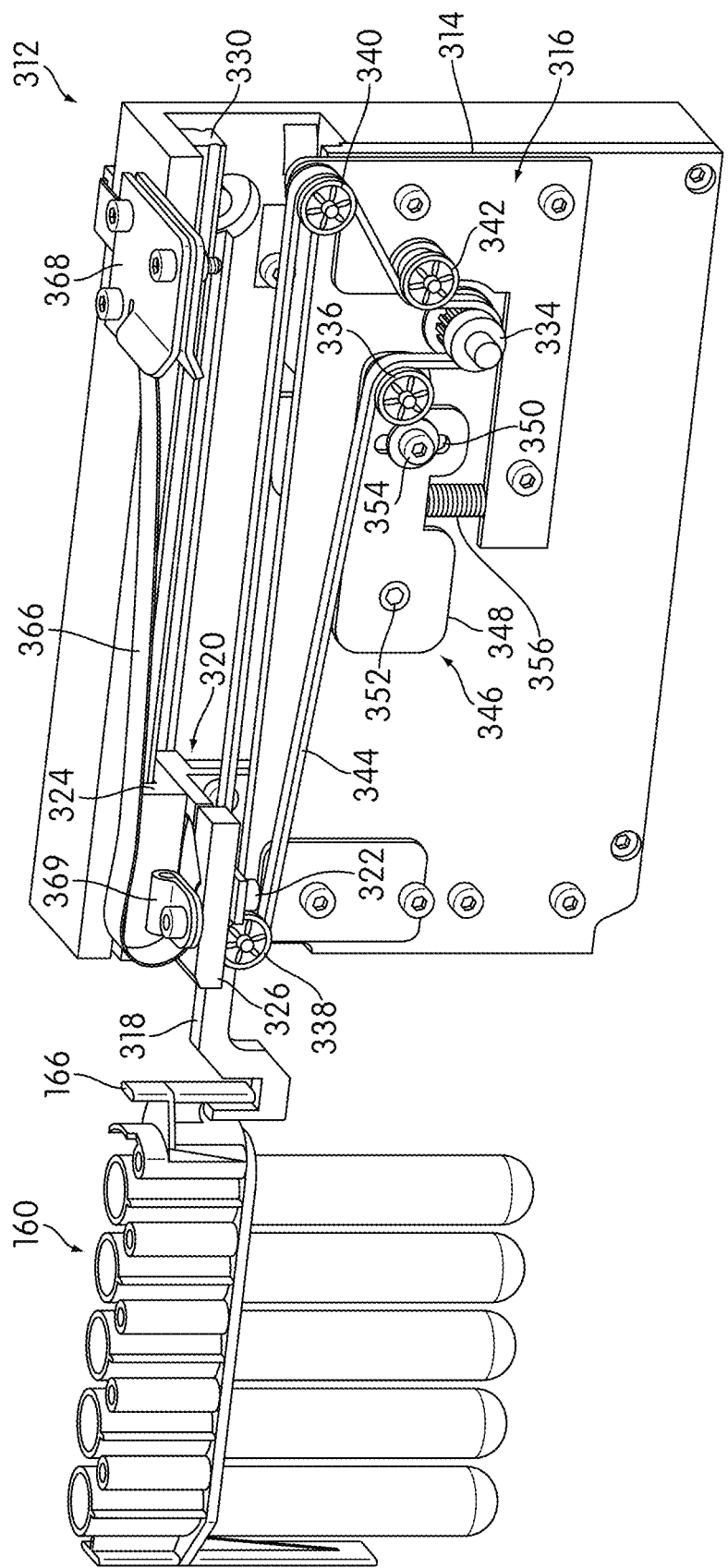
FIG. 30 is a perspective view of the distributor head with the receptacle hook in an extended position.
Figure 31:
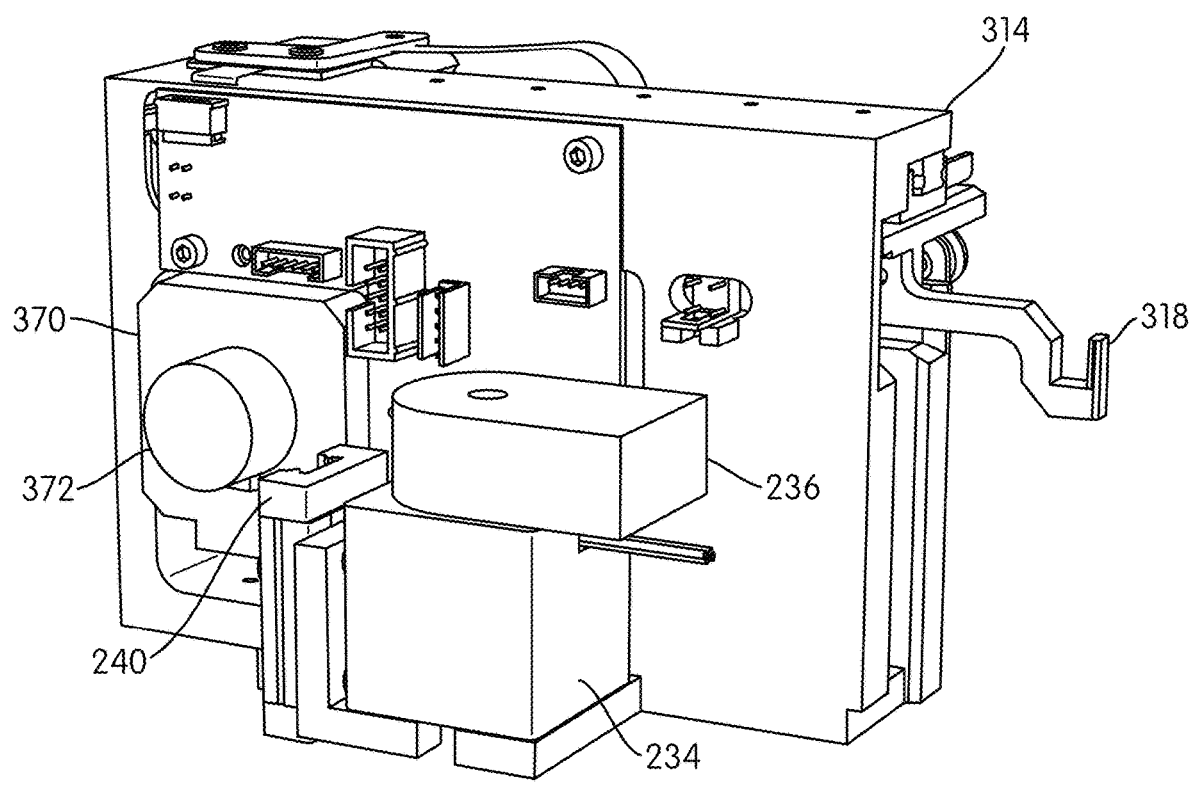
FIG. 31 is an opposite side perspective view of the distributor head.

Details of the rotary distributor 312 are shown in FIGS. 29-31. Rotary distributor 312 includes a distributor head 314 defining a partial enclosure for holding an MRD 160 or reagent card 760 and a receptacle hook 318 configured to engage the manipulating structure 166 of an MRD 160 or the manipulating hook 764 of the reagent card 760.

A hook actuator system 316 effects linear translation of the receptacle hook 318 with respect to the distributor head 314 between an extended position, as shown in FIG. 30, and a retracted position, as shown in FIG. 29. The hook actuator system 316 includes a hook carriage 320 to which the receptacle hook 318 is attached. A drive belt 344 is attached to the hook carriage 320 by a screw and bracket indicated at 322. Drive belt 344 is carried on a drive wheel 334 and idler wheels 336, 338, 340, 342.

Referring to FIG. 31, which is a prospective of an opposite side of the distributor head 314, a drive belt motor 370 having a rotary encoder 372 is attached to the distributor head 314. Drive belt motor 370 is coupled to the drive wheel 334 that drives the drive belt 344 of the hook actuator system 316.

The hook actuator system 316 preferably includes a belt tensioner 346 for maintaining proper tension in the belt 344. Belt tensioner 346 includes a pivoting idler wheel bracket 348 to which idler wheel 336 is attached and which is pivotally attached to the distributor head 314 by a pivot screw 352. A slot 350 is formed in an end of the pivoting idler wheel bracket 348, and a position lock screw 354 extends through the slot 350 into the distributor head 314. A spring 356 bears against a portion of the pivoting idler wheel bracket 348. Tension in the belt 344 can be adjusted by loosening the position lock screw 354, thereby allowing the spring 356 to pivot the pivoting idler wheel bracket 348 and thus urge the idler wheel 336 upwardly to create the proper tension in the drive belt 344. When proper tension is achieved in the drive belt 344, the position lock screw 354 can thereafter be retightened.

The hook carriage 320 includes a rail channel 324 that translates along a hook carriage guide rail 330 attached to an upper, internal portion of the distributor head 314. The receptacle hook 318 is attached to a mount 326 disposed between the rail channel 324 and the hook 318.

A hook home sensor, e.g., a slotted optical sensor or limit switch, may be provided to indicate when the hook 318 is in the retracted, or "home," position when a sensor flag extending from the mount 326 extends into the slotted optical sensor. Other types of sensors may be used for indicating a home position, such as proximity sensors, magnetic sensors, capacitive sensors, etc. The receptacle hook 318 and hook carriage 320 are operatively coupled for electronic communication with the remainder of the rotary distributor 312 by means of a flexible cable 366 attached at one end to the hook carriage 320 and at a printed circuit board or other connector located on the distributor head 314. Strain reliefs 368 and 369 may be provided for securing the flexible cable 366 to the distributor head 314 and the hook carriage 320, respectively.

Figure 32:
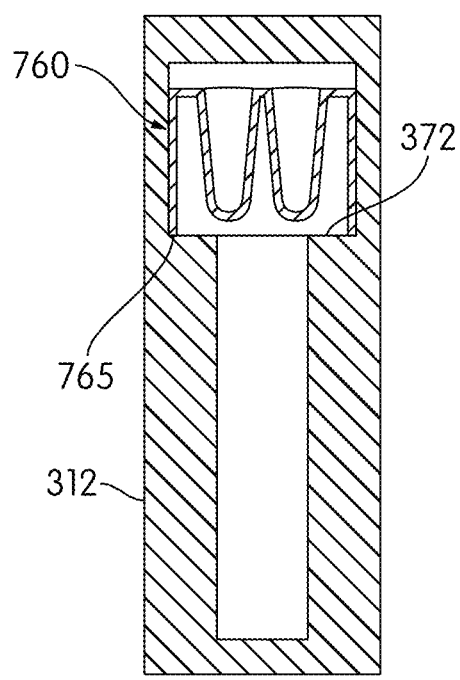
FIG. 32 is a transverse cross-section of the rotary distributor with a reagent card disposed therein.

FIG. 32 illustrates a manner in which a reagent card 760 may be transported within the module 400 by means of the rotary distributor 312. As shown in FIG. 32, the rotary distributor 312 may be configured to receive and hold a reagent card 760 that is pulled into the distributor 312 by the manipulating hook of the rotary distributor 312 with the bottom edge 765 of the card 760 supported on a rail 372 formed on the inner walls of the distributor 312

Figure 33:
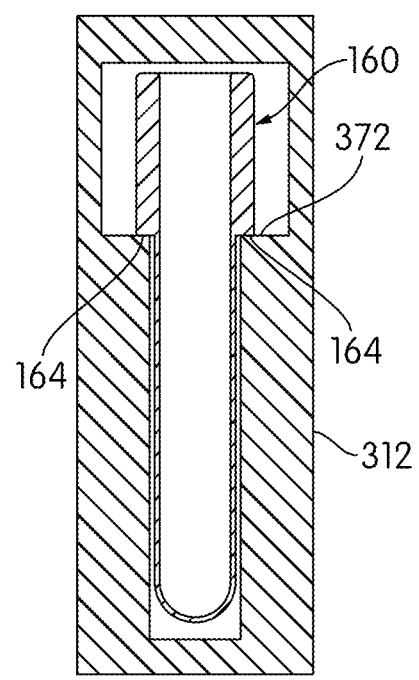
FIG. 33 is a transverse cross-section of the rotary distributor with an MRD disposed therein.

Similarly, FIG. 33 illustrates a manner in which an MRD 160 may be transported within the module 400 by means of the rotary distributor 312. As shown in FIG. 33, the rotary distributor 312 may be configured to receive and hold an MRD 160 that is pulled into the distributor 312 by the manipulating hook of the rotary distributor 312 with the connecting rib structure 164 of the MRD 160 supported on a rail 372 formed on the inner walls of the distributor 312.

The receptacle distribution system 200 includes a distributor moving apparatus constructed and arranged to move the distributor head 314 in a circular path or in a vertical, linear path. More specifically, in one exemplary embodiment, the distributor moving apparatus includes a rotary dive system 212 constructed and arranged to move the distributor head 314 in a circular path and an elevation system 230 constructed and arranged to move the distributor head 314 in a vertical direction.

Details of the rotary drive system 212 are shown in FIGS. 27, 28, 34, and 35.

The first upright wall 218 and the second upright wall 220, on which the distributor head 314 is supported, are mounted onto a turntable 214 that is mounted for rotation about its central axis on the bottom panel 208 of the frame 202. A motor 222, attached to the bottom panel 208 and having a rotary drive gear 204 extending above the bottom panel 208, engages peripheral teeth of the turntable 214 so that powered rotation of the motor 222 effects rotation of the turntable 214, as well as the first and second upright walls 218, 220 and the distributor head 314 supported thereon. Rotary motor 222 is preferably a stepper motor for providing precise control of the rotation of the turntable 214 and preferably includes a rotary encoder 223 for providing rotational position feedback to a control system controlling the rotary motor 222. Other means for rotationally coupling the distributor head 314 to the motor 222 are encompassed within this disclosure and include, for example, belt(s) and pulley(s), gear trains comprising one or more gears, drive shafts and worm gears, etc.

Figure 35:
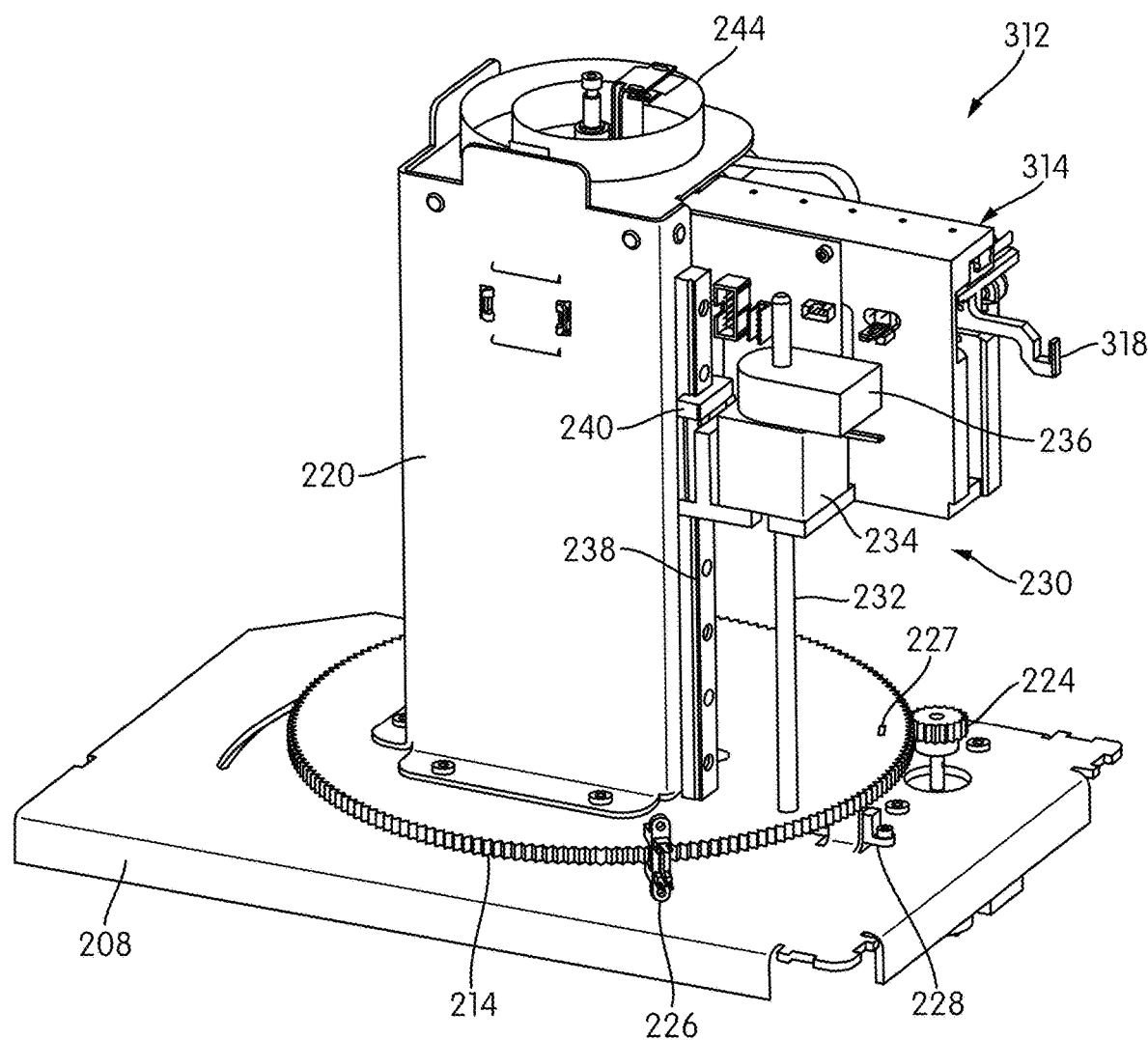
FIG. 35 is a top rear perspective view of the distributor moving system.

As shown in FIG. 35, a positional sensor 226, which may comprise a slotted optical sensor including an optical transmitter-receiver pair, provides a rotational position feedback signal of the turntable 214. Optical sensor 226 may be configured to detect a passing of one or more positional flags on the turntable 214 for indicating one or more specific rotational positions. Sensor 226 includes prongs, or portions, located above and below the turntable 214 and thus the positional flag(s) may comprise one or more openings (e.g., 227) formed through the turntable. Passage of an opening between the portions of sensor 226 located above and below the turntable 214 complete the optical signal transmission between the transmitter and receiver portions of the sensor 226 and thus generate a signal corresponding to the passage of the opening. Other types of sensors may be used for indicating particular rotational positions, including proximity sensors, magnetic sensors, capacitive sensors, etc.

A second optical sensor 228 may be provided below the turntable 214. Sensor 228 may comprise a slotted optical sensor including an optical transmitter-receiver pair for detecting the passage of one or more sensor flags (not shown) extending beneath the turntable 214 for indicating a rotational position. Other types of sensors may be used for indicating a home position, including proximity sensors, magnetic sensors, capacitive sensors, etc.

Details of a distributor elevation system 230 are shown primarily in FIG. 35. The elevation system 230 includes a threaded rod 232 extending upwardly from the turntable 214 through a motor 234 and internal thread drive 236 mounted to the distributor head 314 (see also FIG. 31). Rotation of the internal thread drive 236 by the motor 234 causes the motor and the distributor head 314 to which it is attached to translate up or down the threaded rod 232. A guide rail 238 extends vertically up one edge of the second upright wall 220, and the motor 234 is coupled to the guide rail 238 by a rail coupling 240. Alternatives to the threaded rod and the internal thread drive for moving the distributor head 314 vertically are encompassed in this disclosure and include, for example, a rack and pinion or a belt drive system.

Figure 34:
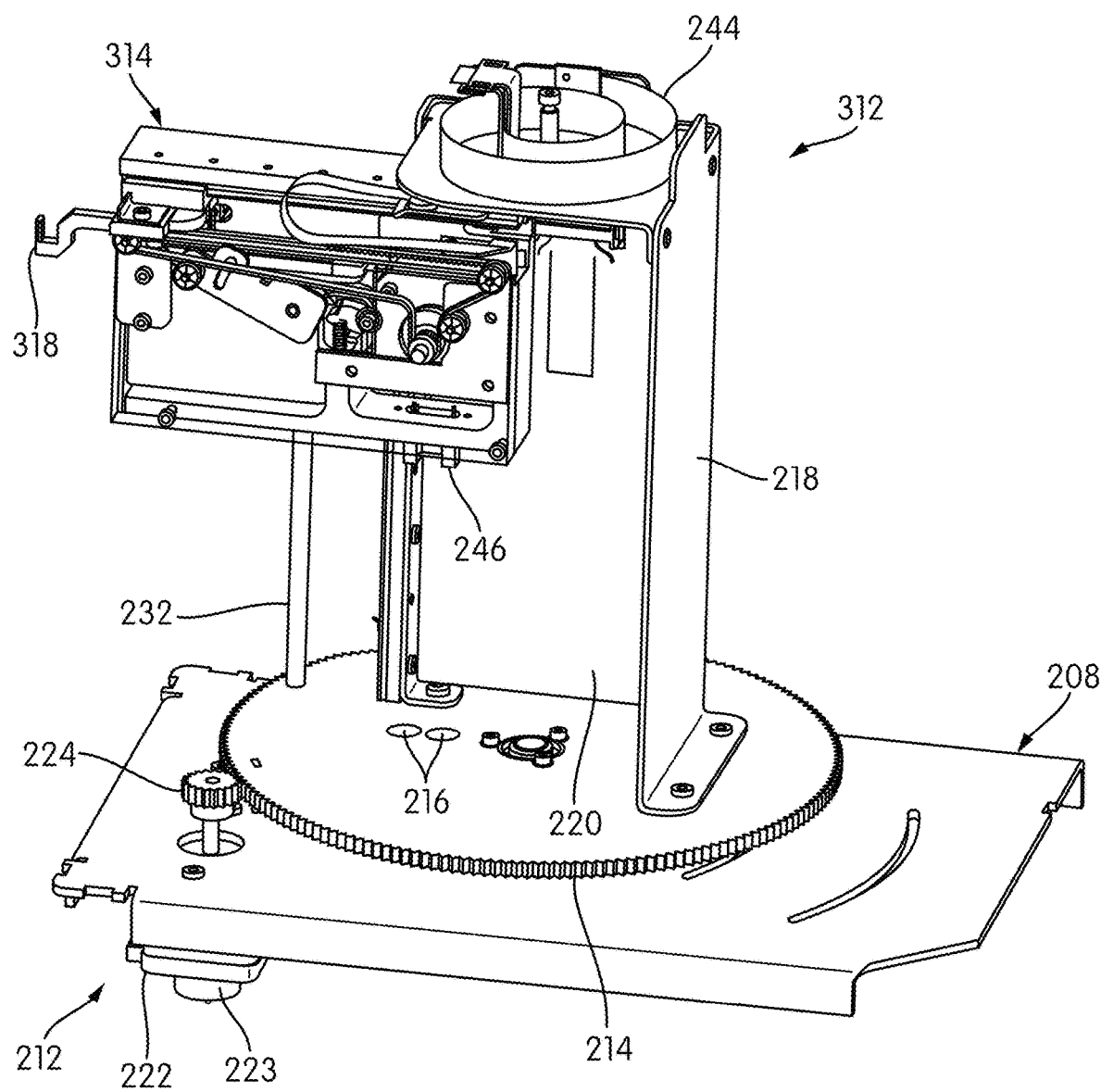
FIG. 34 is a top front perspective view of an embodiment of a distributor moving system of the receptacle distribution system.

Referring to FIGS. 27, 28, and 34, a sensor 246 extends below the distributor head 314. As the distributor head 314 is lowered by the elevation system 230, separate prongs of the sensor 246 extend into openings 216 formed in the turntable 214. Sensor 246 may be a slotted optical sensor with the prongs thereof forming a transmitted-receiver pair. An optical signal between the spaced prongs is broken when the prongs enter the openings 216, thereby sending a signal to a control system that the distributor head 314 is at its lowermost position. Other types of sensors may be used for indicating a down position for the distributor head 314, including, for example, proximity sensors, magnetic sensors, capacitive sensors, etc.

Data and power are communicated between the rotary distributor 312 and the module 400 by means of a coiled cable 244 that can accommodate rotation of the rotary distributor 312 with respect to the frame 202 by, for example, 180° in either direction.

To transfer an MRD 160, the distributor head 314 is rotated a few degrees by the rotary drive system 212 of the rotary distributor 312, the hook 318 is extended by the hook actuator system 316, and the head 314 is rotated in an opposite direction to engage the manipulating structure 166 of the MRD 160. The distributor hook 318 is then retracted, and the MRD 160 is pulled into the distributor head 314. Similarly, to transfer a reagent card 760, the distributor head 314 is rotated a few degrees by the rotary drive system 212, the hook is extended by the hook actuator system 316, and the head 314 is then rotated in the opposite direction to engage the manipulating hook 764 of the reagent card 760. The distributor hook 318 is then retracted, and the reagent card 760 is pulled into the distributor head 314.

Receptacle Handoff Module

The receptacle handoff module 602 is configured to transfer a receptacle, such as the MRD 160, between the receptacle distributor 150 of the analyzer 100 and the rotary distributor 312 of the processing extension module 400. Both the receptacle distributor 150 of the analyzer 100 and the rotary distributor 312 of the processing extension module 400 manipulate the MRD 160 using a hook or other similar device to engage the manipulating structure 166 of the MRD 160. Therefore, after the MRD 160 is disengaged by the receptacle distributor 150 of the analyzer 100, the MRD 160 can be positioned and oriented in such a manner as to present the manipulating structure 166 to the rotary distributor 312 of the processing extension module 400. The handoff module 602 performs this function.

Details of the handoff module 602 are shown in FIGS. 27, 28, 39, 40. The receptacle handoff module 602 comprises a receptacle yoke 604 configured to receive and hold an MRD 160 placed into the yoke 604 by the receptacle distributor 150 of the analyzer 100. The yoke 604 is mounted on a handoff module bracket 606, attached to and extending from the bottom panel 208 of the frame 202, so as to be rotatable about a vertical axis of rotation. In one exemplary embodiment, the yoke 604 is coupled to a handoff module motor 680 attached to the bracket 606. Motor 680 may be a stepper motor for precise motion control and may include a rotary encoder 682 for providing rotational position feedback of the receptacle yoke 604 to a controller. A sensor 684, which may be a slotted optical sensor comprising an optical transmitter-receiver pair, is mounted to the bracket 606 and detects a home flag 686 extending from the yoke 604 for providing rotational position feedback. Other types of sensors may be used for providing position or orientation feedback, including proximity sensors, magnetic sensors, capacitive sensors, etc. After the MRD 160 is placed in the yoke 604 by the receptacle distributor 150 of the analyzer 100 and the receptacle distributor 150 disengages the MRD 160, the housing 604 is rotated to present the manipulating structure 166 of the MRD 160 to the rotary distributor 312 of the processing extension module 400.

Alternatively, the handoff module 602 may be passively actuated by the rotary distributor 312. For example, the handoff module rotation may be tied to the rotation of the rotary distributor 312 (e.g., via a cable, belt, gear, or other means) such that when the rotary distributor 312 rotates to the handoff position, the handoff module 602 would spin around to face the rotary distributor 312. When the rotary distributor 312 rotates away from the handoff module 602, the handoff module 602 would rotate back toward the receptacle distributor 150 of the analyzer 100.

MRD Storage Station

As shown in FIG. 14, the MRD storage stations 608, 610, 612 are located on the receptacle processing deck 600 of the processing extension module 400 and serve as temporary locations for MRDs in the processing extension module 400. Storage stations 608, 610, 612 include a number of slots 614, each configured to receive an MRD 160. The storage stations 608, 610, 612 are arranged in an arc, thereby accommodating the rotational path of motion of the rotary distributor 312. Providing additional storage for MRDs within processing extension module 400 provides the advantage of enhancing workflow by permitting flexibility in the timing that any particular MRD, or contents thereof, is/are utilized within processing extension module 400. This permits MRDs that may arrive in processing extension module 400 later to be processed out of order, for example, to address urgent needs in a laboratory.

Magnetic Elution Slots/Reagent Card Loading Stations

The magnetic elution slots 620 (two in the illustrated embodiment) and the reagent card loading stations 640 are supported on a bracket 642 attached to frame 202. The purpose of each magnetic elution slot 620 is to hold an MRD 160 and apply magnetic force to the contents of the MRD to pull the magnetic beads to the side walls of each receptacle vessel 162 while the fluid transfer pipettor 410 aspirates the eluate fluid from the receptacle vessels 162.

Figure 36:
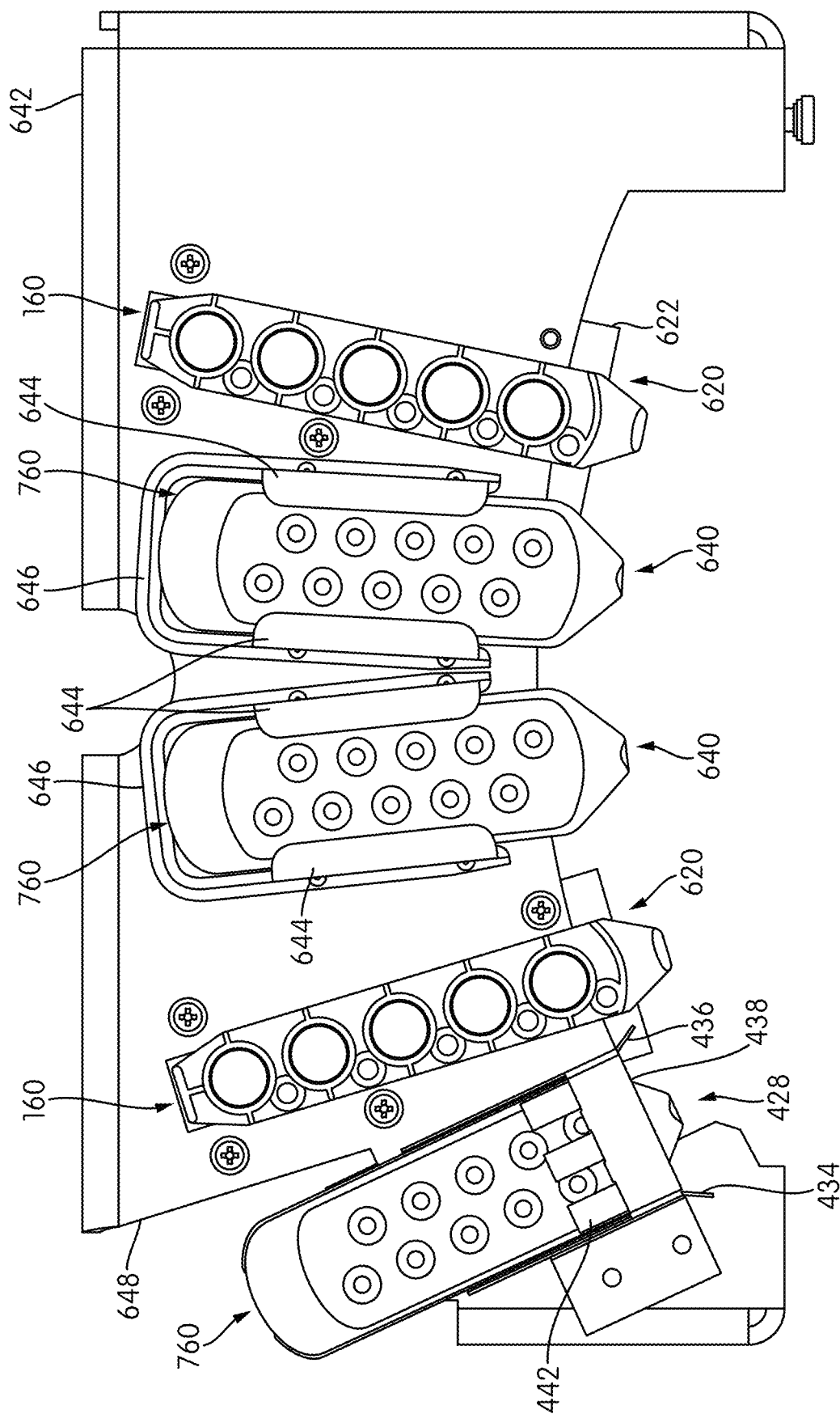
FIG. 36 is a top plan view of an embodiment of magnetic elution slots and reagent card loading stations of the processing extension module.
Figure 37:
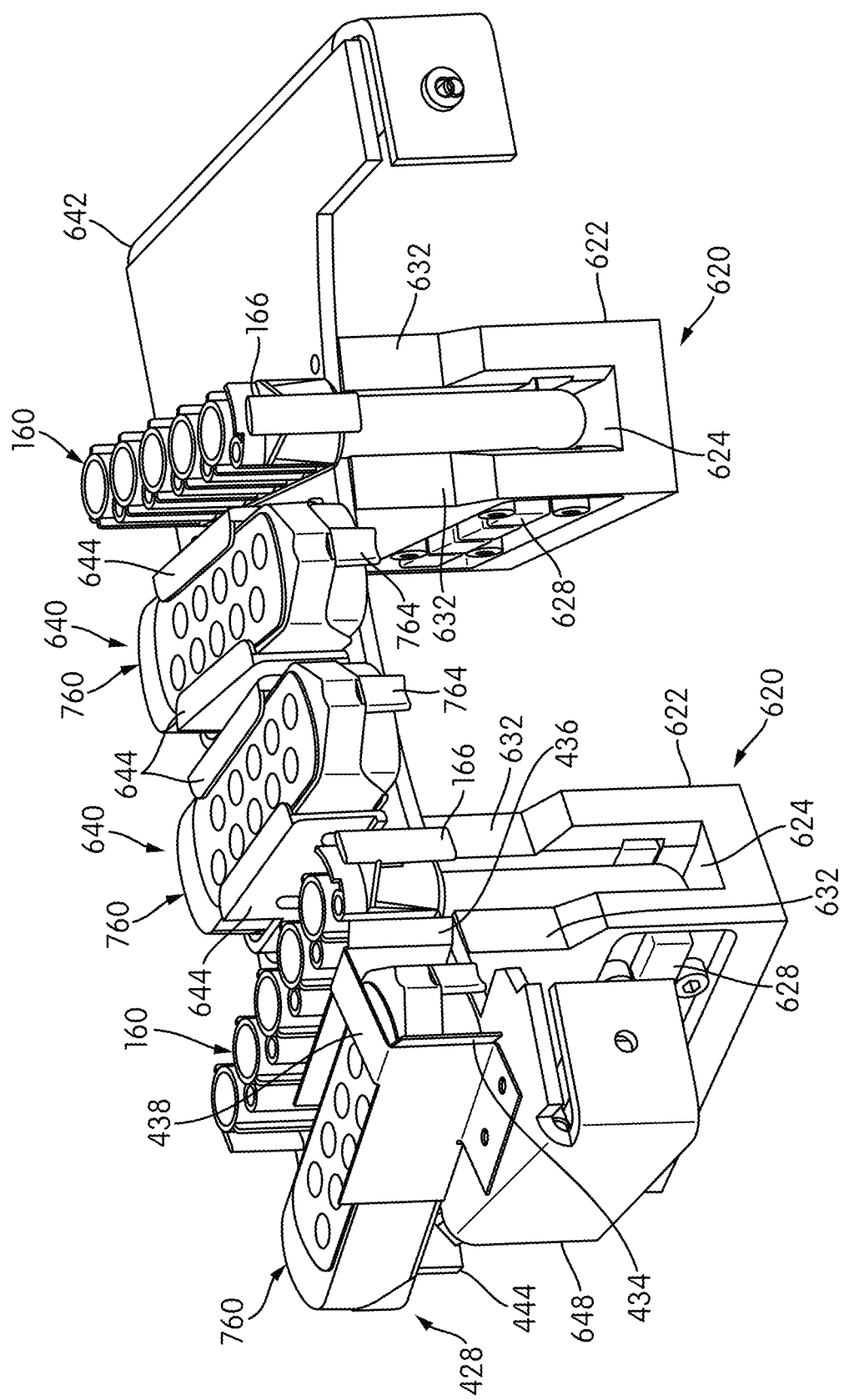
FIG. 37 is a front end perspective view of the magnetic elution slots and reagent card loading stations.
Figure 38:
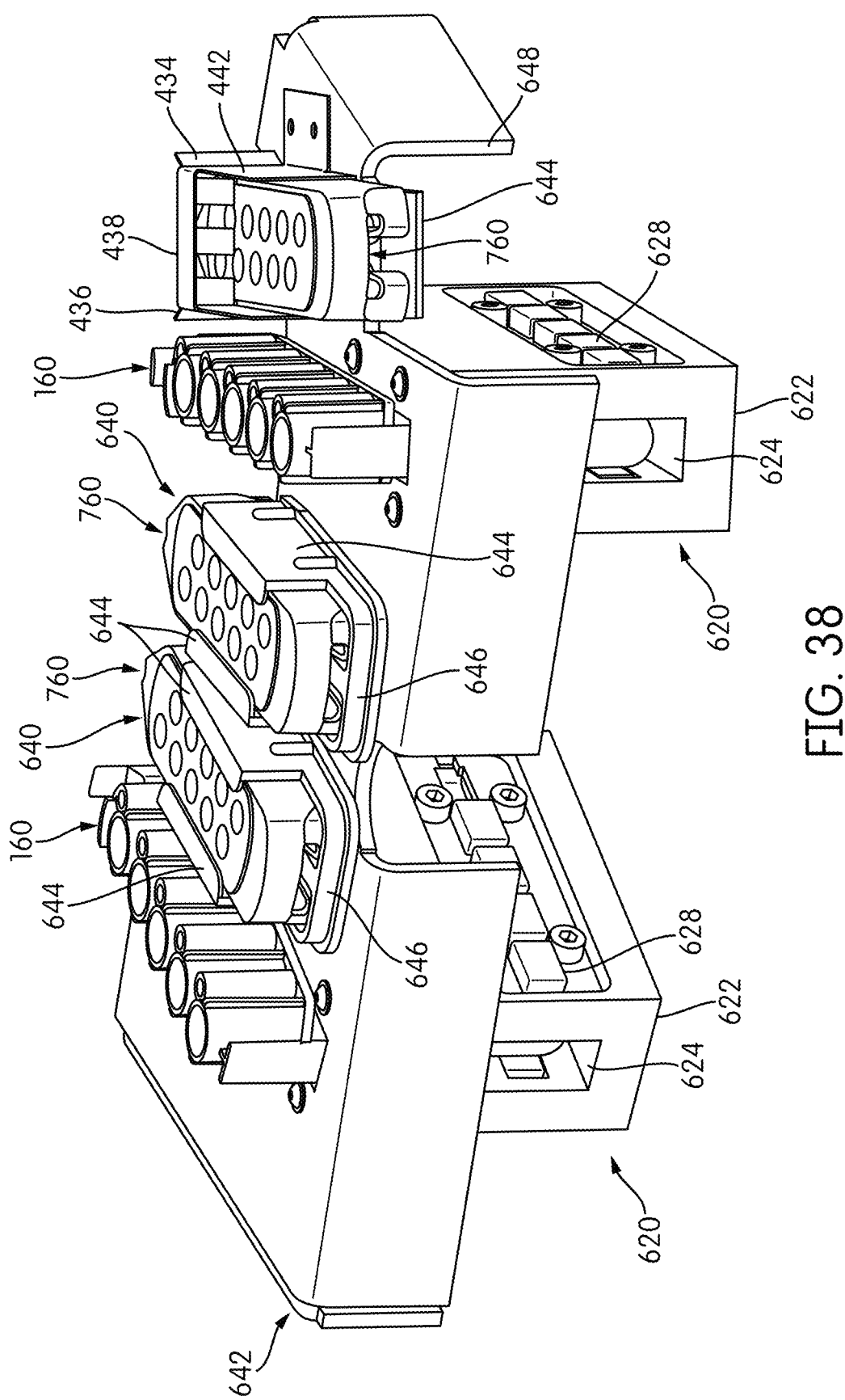
FIG. 38 is a back end perspective view of the magnetic elution slots and reagent card loading stations.
Figure 39:
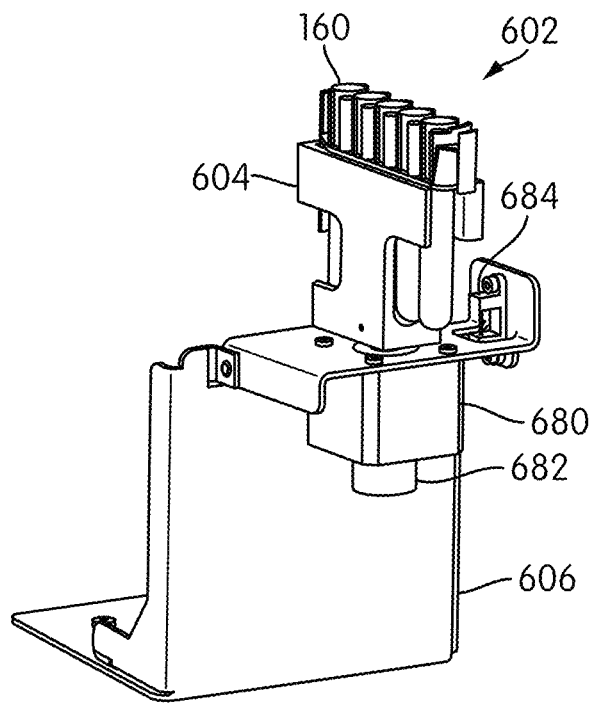
FIGS. 39 and 40 are perspective views of an embodiment of an MRD handoff module of the processing extension module.
Figure 40:
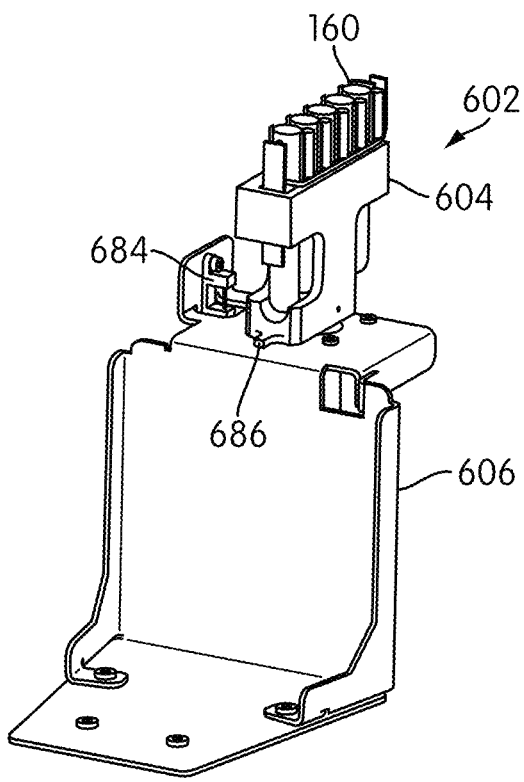

Details of the magnetic elution slots 620 and the reagent card loading stations 640 are shown in FIGS. 36-38. Each magnetic elution slot 620 comprises a block 622 within which is formed a slotted opening 624. An MRD 160 placed within the slotted opening 624 is supported within the opening 624 by the connecting rib structure 164 of the MRD 160 resting on the top of bracket 642. The manipulating structure 166 extends out of the opening 624, and a cutout 632 in each side wall of the block 622 enables the hook 318 of the rotary distributor 312 to move laterally into or laterally out of the MRD manipulating structure 166 of an MRD 160 located within the slotted opening 624. The top of the MRD is uncovered, thus enabling pipettor access to the receptacle vessels 162 of the MRD 160 held within the elution slot 620. Magnets 628 are attached to or embedded within one or both walls defining the slotted opening 624. Individual magnets 628 may be provided for each receptacle vessel 162 of the MRD 160, as shown in FIGS. 37 and 38, or a single magnet may be provided for a receptacle that comprises one or more individual receptacle vessels.

The reagent card loading stations 640 are defined by spaced-apart hold-down features 644 extending above the bracket 642 and a backstop 646 defining a back end of each reagent card loading station 640. A reagent card 760 is inserted between the hold-down features 644, under a lateral flange, and are pushed into the loading station 640 until the back end of the reagent card 760 contacts the backstop 646.

Reagent Card Trash Chute

A reagent card trash chute 428 is supported on the bracket 642. In an exemplary embodiment, reagent card trash chute 428 includes an entrance structure, defined by side walls 434, 436 and a top panel 438, through which a reagent card 760 is inserted into the trash chute 428. Sidewalls 434, 436 are attached to the top of the bracket 642 and are bent or flared outwardly at their forward edges to provide a funneling entrance to the trash chute 428. Resilient tabs 442 extend down from the top panel 438.

To discard a reagent card 760, the rotary distributor 312 inserts the card 760 into the trash chute 428 between the side walls 434, 436. When the reagent card 760 is inserted into the trash chute 428, there is a clearance between the top panel 438 and the top of the reagent card 760. The resilient tabs 442 bear against the top of the reagent card 760 and hold the card 760 down within the trash chute 428. The angle the resilient tabs 442 permits the card 760 to be pushed into the of the trash chute 428, but resists movement of the card 760 out of the trash chute.

When a subsequent reagent card 760 is inserted into the reagent card trash chute, it is pushed against the card 760 previously inserted into the trash chute 428, thereby pushing the previously-inserted card further into the trash chute 428. A cut-out 648 is formed in the bracket 642, so the previously-inserted card 760 eventually falls from the trash chute 428 and, guided by a guide ramp 444 extending down from the bracket 642, into a trash bin located below the trash chute 428.

Reagent Card Changer

Figure 15:
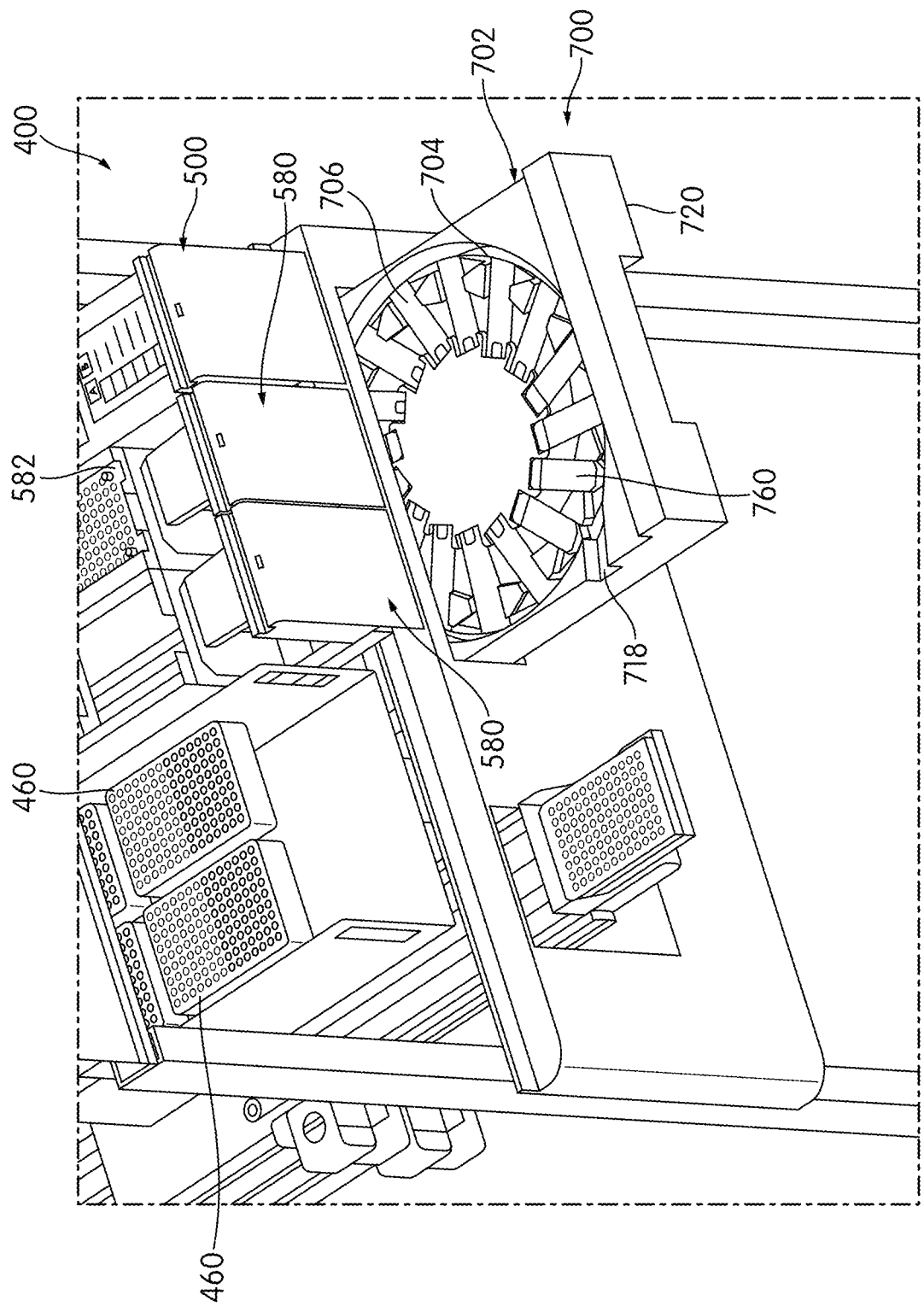
FIG. 15 is a partial, front perspective view of the processing extension module with a card carousel drawer of a reagent card changer in an open position.
Figure 16:
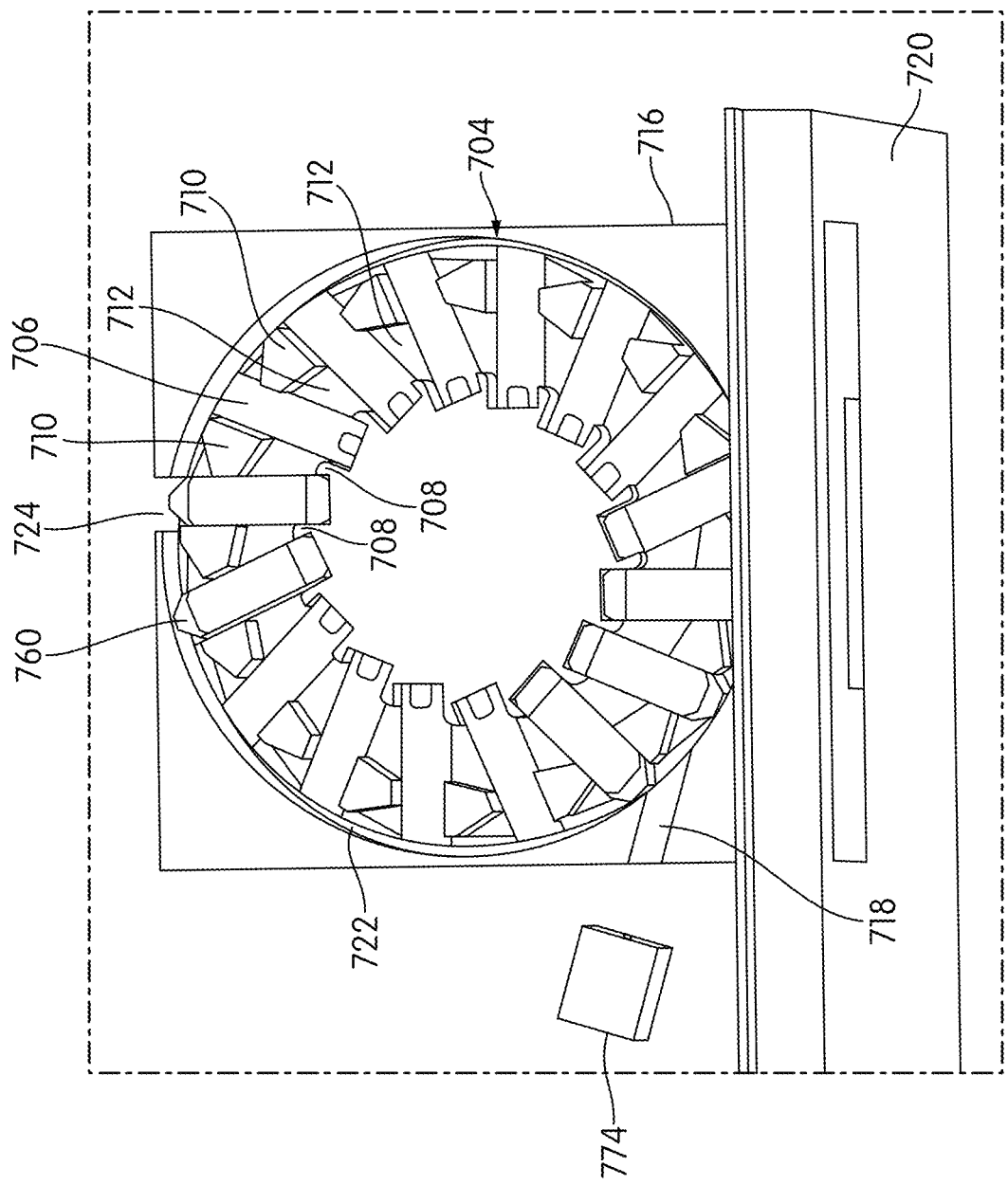
FIG. 16 is a partial, top perspective view of the card carousel drawer.
Figure 17:
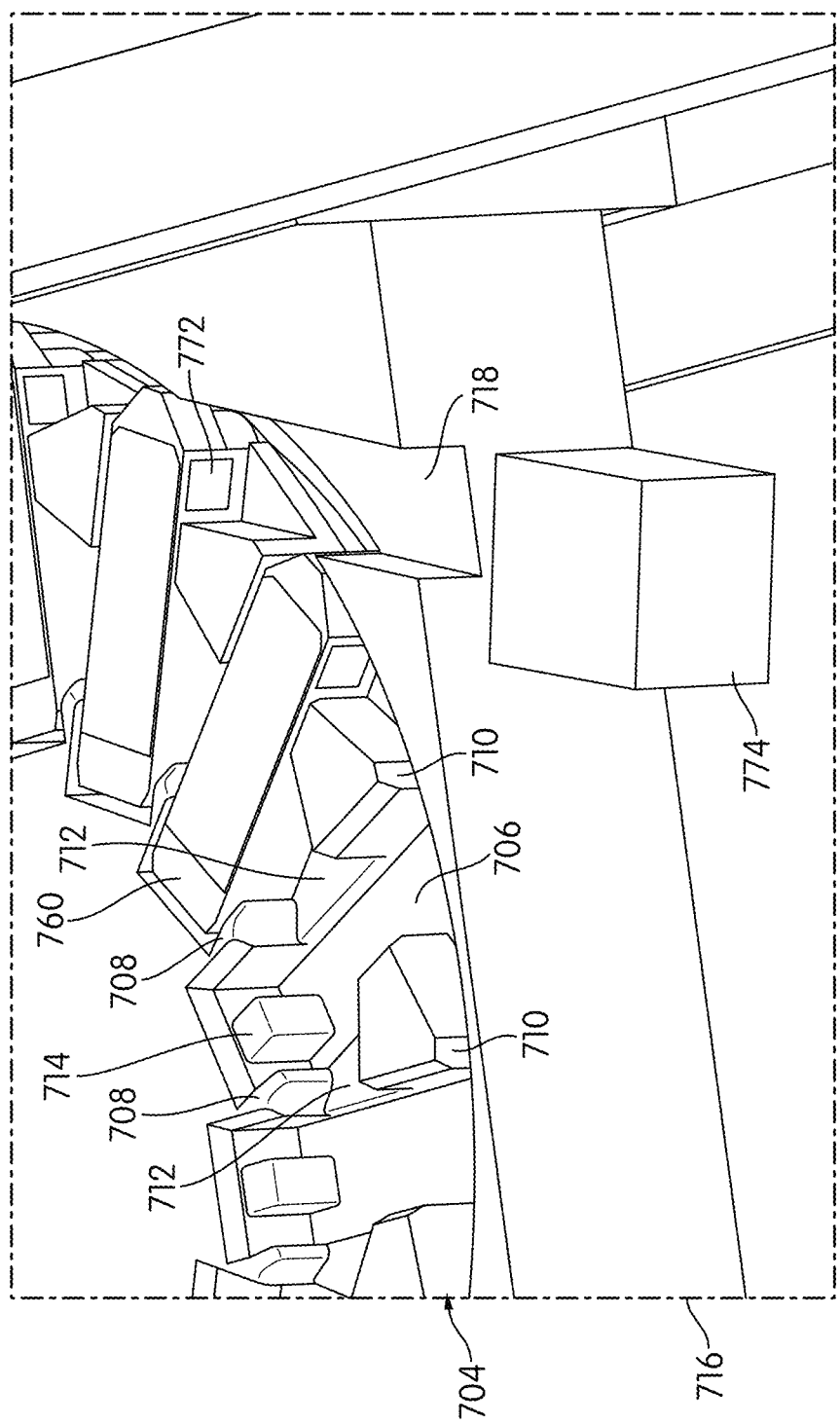
FIG. 17 is a partial, side perspective view of the card carousel drawer.

Details of a reagent card changer 700 are shown in FIGS. 15-17. The purpose of the reagent card changer 700 is to provide fully independent reagent card loading and test execution whereby an operator may place reagent cards in a card input device and/or remove reagent cards from the card input device while previously loaded reagent cards are stored within a storage chamber, which may be temperature controlled, and are available for access by the instrument independently of the status of the card input device. The reagent card changer is configured to move cards between the card input device and the storage chamber, As shown in FIGS. 15-17, in one exemplary embodiment, the card input device comprises a card carousel drawer 702 which may be pulled open from the processing extension module 400 and which contains a rotatable card carousel 704. The card carousel 704 includes a number of card stations 706, each of which is adapted to receive and carry a reagent card 760 and which are defined by radially inner dividers 708 and radially outer dividers 710. As can be seen in FIGS. 15-17, the card stations 706 of the card carousel 704 are arranged about the outer perimeter of the card carousel 704, but the elongated card stations 706, and reagent cards 760 carried thereby, are not oriented in a radial direction with respect to the center of the carousel 704. Each card station 706 is oriented at an angle (e.g. 5-) 20° with respect to a true radial orientation. This configuration of reagent cards optimizes the placement of reagent cards 760 on the carousel 704, thereby enabling the carousel 704 to carry the maximum number of reagent cards 760 and providing access of identifiable indicia present on each reagent card 760 to the barcode reader 774.

A gap 712 between each inner divider 708—outer divider 710 pair enables an operator to insert his or her fingers into the gap 712 to thereby grasp the sides of the reagent card 760 for placing the card into the card station 706 or for removing the card 760 from the card station 706. Each card station 706 of the card carousel 704 also includes an alignment block 714 at a radially inner end of the card station 706. The alignment block 714 disposed within the rear recess 770 of the reagent card 760 helps to maintain the proper alignment and position of the reagent card 760 within the card station 706.

The card carousel drawer 702 includes a carousel frame 716, preferably disposed on a track that enables the frame 716 to be slid into or out of the module 400 as a drawer. The frame 716 includes a drawer front 720. The card carousel 704 is rotatably disposed within the frame 716, which may include a circular recess 722 shaped so as to conform to the carousel 704.

Carousel 704 is motorized to effect powered rotation of the carousel. In one exemplary embodiment, the card carousel drawer 702 may include a motor (not shown) that is coupled, for example by a belt and pulley arrangement (not shown), to the carousel 704 to effect powered rotation of the carousel 704. The motor may be mounted to the carousel frame 716 and move in and out with the carousel drawer 702, connected to the module 400 by a flex cable. Carousel drawer 704 may include one or more position sensors for detecting when the carrousel is in an open or closed position and communicating a corresponding signal to the system controller. Such sensor(s) may include optical sensors, proximity sensors, magnetic sensors, capacitive sensors, etc.

The card carousel drawer 702 may also include a software-controlled lock.

The card carousel drawer 702 preferably also includes one or more sensors for tracking the positions of the card station 706. For example, the card carousel 704 may include a home flag, such as a tab and an optical sensor that detects the position of the tab at a specified rotational position of the carousel 704. Other types of sensors may be used for indicating a home position, including proximity sensors, magnetic sensors, capacitive sensors, etc. Furthermore, the motor driving the carousel 704 may be a stepper motor including a rotary encoder for generating signals corresponding to a rotational position of the carousel 704.

The processing extension module 400 may include a machine card reader configured to read a machine code provided on each reagent card 760 providing information regarding the reagent card, such as the identity of the assay reagents carried within the card, manufacturer, lot number, expiration date, etc. The machine code may also include a unique identifier specifically identifying that particular reagent card 760. The machine code reader apparatus may comprise a barcode reader 774 configured to read a barcode label 772 disposed on the reagent card 760. Barcode label 772 may be a two dimensional or one dimensional barcode. A scanning slot 718 formed in the carousel frame 716 provides an opening through which the barcode reader 774 may read a label 772 on the reagent card 760. Similarly, the orientation of the reagent card 760 carried in the card station 706 of the card carrousel 704, may be set at an angle with respect to a true radial orientation, and the shape of the outer dividers 710, being generally trapezoidal in shape, creates a clearance opening through which the barcode reader 774 can read the barcode label 772 disposed on the reagent card 760. Together with the rotary encoder, the barcode reader 772 provides an indication where each reagent card 760 is positioned within each card station 706 of the card carousel 704. Although a barcode scanner is exemplified, the use of other technologies such as RFID and QR codes are contemplated.

Each card station 706 may include a station empty barcode disposed on a side of each outer divider 710 that will be read by the barcode reader 774 if a reagent card 760 is not positioned within the card station 706.

Figure 18:
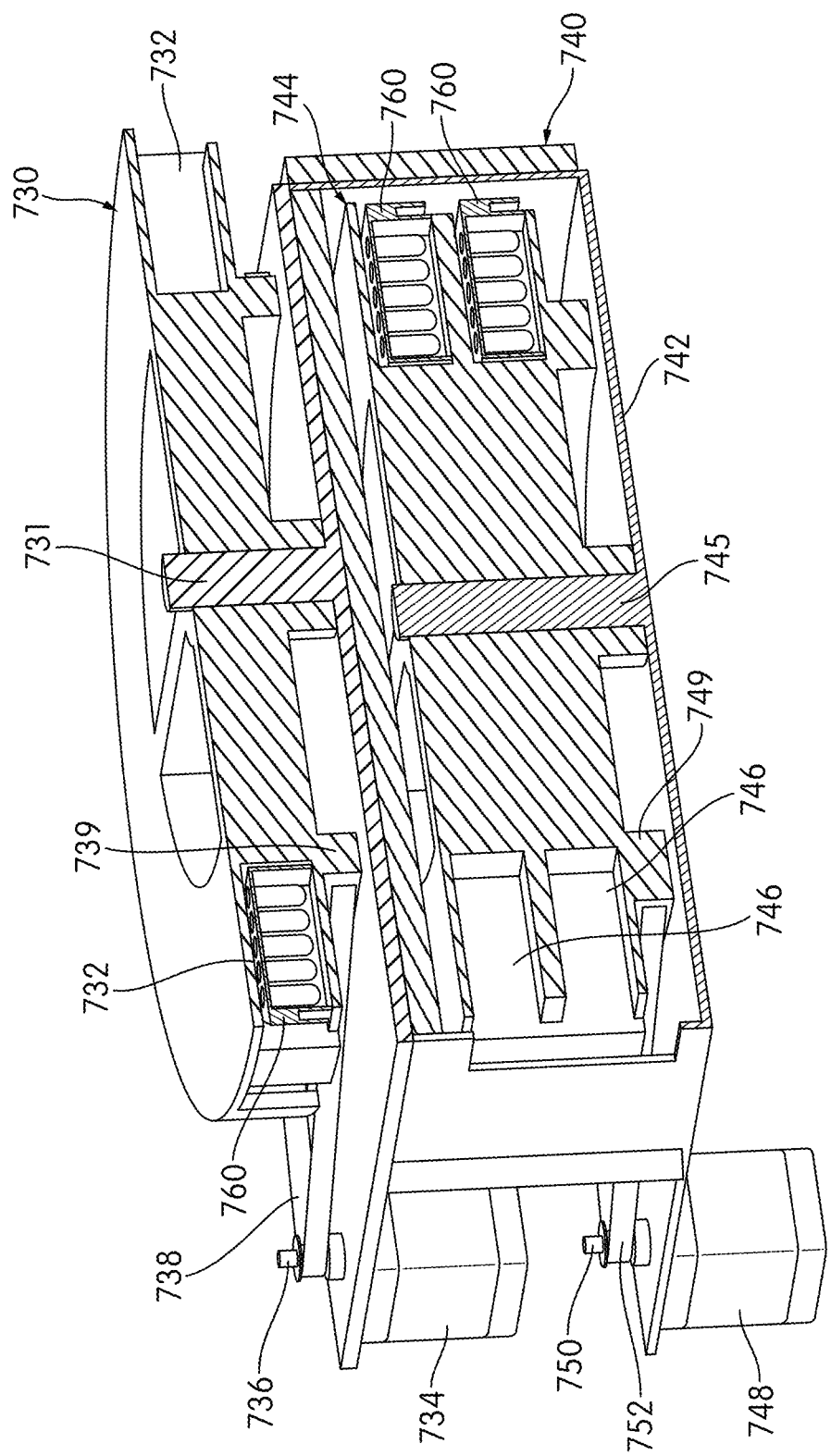
FIG. 18 is a cross-sectional, rear perspective view of an alternative embodiment of a reagent card changer and a reagent card storage chamber.

In another exemplary embodiment, the card input device comprises an alternative card carousel 730 shown in FIG. 18. Carousel 730 is not carried on drawer configured to be pulled out of the module 400, but instead, includes radially oriented card stations 732 arranged about the perimeter of the carousel 730 and is accessible through a slot in front of the processing extension module 400 which may be covered by a door that is openable by the operator. Powered rotation of the card carousel 730 may be provided by a carousel drive system that may include a motor 734 having an output drive wheel 736 that is coupled to a drive pulley 739 of the carousel 730 by means of a drive belt 738. Motor 734 may comprise a stepper motor having a rotary encoder, and a home flag may be provided on the carousel 730 to detect and monitor the rotational position of the carousel 730 and thus each card station 732.

FIG. 18 also shows an exemplary embodiment of a reagent card storage chamber represented by reference number 740. The storage chamber 740 is disposed beneath the card carousel 730. In the embodiments described above, the card carousel drawer 702 would be disposed within the module 400 above the storage chamber 740 and would be movable with respect thereto.

Storage chamber 740 includes a housing 742 that defines a temperature controlled chamber therein. The desired storage temperature may be as low as 4° C., but could be any temperature at or below ambient temperature, e.g., 15° C. In certain embodiments it is preferable that the module control the humidity level of the air circulating within the temperature controlled chamber. As part of this process, the module is optionally equipped to collect condensed water, and route it outside the cooled storage area for disposal.

Housing 742 may be insulated and may be cooled by peltier devices that can be mounted directly onto the housing 742 or by peltier devices coupled to a heat exchanger that cools a fluid, such as water or a refrigerant, which is circulated around the housing 742. In one embodiment the storage chamber 740 is cooled by two separate peltier devices mounted directly onto the housing 742, each at different temperatures or temperature ranges. In this embodiment the first peltier device is held at a temperature close to the freezing temperature of water. The second peltier is provided at a location within the storage chamber 740 distant or adjacent to that of the first peltier and is provided at a temperature higher than that of the first peltier, e.g., 15° C. The second peltier is in operable communication with a temperature sensor within the storage chamber 740, positioned near the top of the storage chamber 740. The second peltier would operate based on the measured temperature to maintain a predetermined temperature in the storage chamber 740. In this embodiment a fan may be provided within the storage chamber 740 to cause air circulation within the storage chamber 740 through the fan, and past the first and second peltiers. When air passes the first peltier, which is held at a very low temperature, the air will cool, thus decreasing its capacity to hold moisture which moisture will condensate on the peltier or another designated element. Therefore, this dual peltier embodiment provides both a temperature and humidity controlled environment, which is beneficial for increasing the shelf-life of lyophilized reagents which are vulnerable to rapid degradation in the presence of increased temperatures and atmospheric moisture.

Other means of cooling and/or dehumidifying the storage chamber 740 will be apparent to those of ordinary skill in the art.

The housing 742 should be provided with a liquid collection and drainage system or other means for handling condensing liquid inside the housing 742. Such a system may, for example, include piping for directing the collected condensate away from the housing 742 and to a drain or an evaporator.

A storage carousel 744 is rotatably mounted within the housing 742, for example, on shaft 745. Storage carousel 744 includes a plurality of card stations 746 disposed around the perimeter thereof and positioned on one or more levels of the carousel 744. In the illustrated embodiment, storage carousel 744 includes card stations 746 on two levels, one above the other.

Powered rotation of the storage carousel 744 within the storage chamber 742 may be effected by a carousel drive system. The carousel drive system may include a motor 748, which may be a stepper motor, having an output drive wheel 750 coupled by means of a drive belt 752 to a drive pulley 749 of the card carousel 744. Motor 748 may be located outside the housing 742—to keep heat generated by the motor 748 from heating the storage chamber 742—and the drive belt 752 may extend through an opening in the housing 742. Alternatively, a drive pulley coupled to the carousel 744 may be located outside the housing 740. The motor 748 may include a rotary encoder, and the card carousel 744 may include a home flag for monitoring the rotational position of each of the card stations 746 of the card carousel 744.

Operation of the reagent card changer 700 will now be described.

After the reagent cards 760 are placed in the card carousel 704 or card carousel 730 of the card input device, the barcode of each reagent card 760 is read by a barcode reader 774 and the identity and other information provided by the barcode is associated with a particular card station 706,732 of the carousel. Alternatively, the reagent cards may be scanned externally of the module 400, for example, by a hand operated barcode scanner, prior to the reagent card being placed into the card input device.

After reagent cards 760 have been placed into the card input device, such as carousel 704 or carousel 730, card carousel drawer 702 is shut or a door in front of the carousel access opening is closed. Next, the rotary distributor 312 removes one or more reagent cards 760 from the card carousel 704, 730 and moves the reagent card 760 into a card station 746 of the storage carousel 744 of the storage chamber 740. As shown in FIG. 16, the carousel frame 716 of the card carousel drawer 702 includes a card access slot 724 through which the rotary distributor 312 can access the manipulating hook 764 of a reagent card 760 disposed within the card station 706. To enable the rotary distributor 312 to transfer reagent card 760 between the card input carousel 704 or 730, to the one or more levels of the storage carousel 744 of the storage chamber 740, the rotary distributor 312 can be configured to provide powered and controlled vertical, i.e., z-axis, motion. It is preferable that access to the card access slot 724 by the rotary distributor 312 is controlled by a door when the input carousel 704 or 730 is temperature controlled.

Once a reagent card 760 is present in the storage chamber 740, it is available to be utilized in a PCR assay. When a sample is present requiring a particular assay, the carousel of the storage chamber 740 rotates to a position where a reagent card 760 containing the specific unit dose reagents for that particular assay is accessible by the rotary distributor 312. Generally, such assess will be through a door to maintain a tightly controlled temperature environment in the storage chamber 740. The rotary distributor 312 will access the reagent card 760 through the door and move it to a reagent card loading station 640 for reconstitution of one or more lyophilized reagents contained on the reagent card 760. When the reagent card 760 is empty, or when the reagents of one or more wells on the reagent card 760 have been reconstituted and removed, the rotary distributor 312 will again move the reagent card 760. If there are reagents remaining in the card the rotary distributor 312 will transfer the card back to the storage chamber 740. If the card contains no more reagents, or is otherwise designated as inappropriate for continued use (e.g., contaminated or expired reagents), the rotary distributor 312 will transfer the reagent card 760 to either a waste chute 426 or back to the card input carousel 704 or 730 for removal.

A further alternative for scanning each reagent card 760 is for the rotary distributor 312 to present each reagent card 760 to a barcode scanner as each reagent card is removed from the card input carousel and before placing the reagent card 762 into the storage carousel 744.

Reagent identity control is maintained after the bar code (or other machine code) is read on the reagent card 760 by monitoring the position of each card station 706, 732 of carrousel 704, 730 and each card station 746 on the storage carrousel 744 and associating the reagent card identity—from the bar code—with the card station position.

The card carousels 704, 730 rotate independently of the storage carousel 744 of the storage chamber 740 to allow an operator to load and unload reagent cards 760 from the card carousel 704, 730 while the module 400 (i.e., rotary distributor 312) independently accesses reagent cards 760 stored in the storage carousel 744 for assay processing.

The reagent card changer 700 preferably stores at least 28 to 30 or more reagent cards 760.

The process extension module 400 may further include a charged field generator to electrostatic forces to position and hold the lyophilized reagent 768 present in the reagent card 760 at the bottom of each of the mixing wells 762 of the reagent card. Though the reagent 768 may be held at the bottom of the associated mixing well 768 with a previously-imparted electrostatic force, as noted above, the inclusion of a mechanism, such as a charged field generator, to actively pull the lyophilized reagent 768 down to the bottom of the mixing well 762 at the time that the reagent is reconstituted will ensure its positioning in the correct spot in the mixing well during reconstitution. In an embodiment, the charged field generator is positioned below the reagent card loading station 702, 730. Alternatively, or in addition, a charged field generator device could be provided in the card carousel 704, 730 present in the card loading drawer and/or the storage carousel 744 present in the card storage chamber 740. In such an embodiment, the charge field generator device may be located under or operatively coupled to the card station 706, 732 or the card station 746 below the card 760, as providing a charge field generator device within the card storage chamber will have an enhanced electrostatic effect due to the lower temperature and low humidity.

Storage/Expansion Module

Details of compartment 590 for storing accessories or to accommodate possible expansion of the processing extension module, are shown in FIGS. 5, 6, 14, and 15. In one exemplary embodiment, compartment 590 can house a standard 96 well plate. The plate is located such that both pipettor arms 408, 416 can access the 96 well plate location. The expansion space has access to the front (via a drawer mechanism) so that the operator can load and unload the plate. The expansion space can also be accessed from the side of the instrument. A drive system, e.g., comprising a motor-driven belt, may be provided for translating a well plate or other container or component into or out of the processing extension module 400. Compartment 590 can be utilized as an area for collecting vial/cap assemblies that have undergone a PCR and/or melting assay to provide for the ability to perform additional assays (e.g., ELISAs) on the sample contained in the vial/cap assembly. In certain embodiments an arrangement of vial/cap assemblies in the format of a 96 well plate has advantages if further processing of the samples is desired since the 96 well plate size is compatible with a variety of known sample processing and molecular assay instruments.

Instrument Theory of Operation

The analyzer 100 is used for the sample preparation portion of the PCR assay. Specimens and TCR, which may include magnetic beads, are loaded onto the analyzer 100. Elution buffer bottles 502, 504 are loaded on the processing extension module 400 then the processing extension module 400 automatically moves these bottles into a space within the analyzer 100 that can be accessed by a reagent pipettor of the analyzer 100. Through information provided to the analyzer, e.g., by an operator via a user interface or through automated, machine-readable information, such as a bar code, provided on the specimen container, the analyzer recognizes that PCR will be initiated. To process specimens, a receptacle transport mechanism of the analyzer pulls a new MRD from an input queue and places it into a sample dispense position within the analyzer 100. TCR and specimen are transferred from a reagent container and specimen tube, respectively, to each receptacle vessel 162 the MRD 160 by a pipettor within the analyzer 100. The contents of the MRD 160 are then incubated for a prescribed period at a prescribed temperature, and then the MRD is transferred to a magnetic wash station for a magnetic wash procedure.

After the target capture process, the MRD 160 is moved by the receptacle transport apparatus to an amplification reagent dispense position within the analyzer 100. The analyzer pipettor then adds elution fluid to each receptacle vessel 162 of the MRD 160 to separate target (specimen) material from the magnetic particles, and the analyzer mixes the contents before sending the MRD 160 to the processing extension module 400. The processing extension module 400 places the MRD into one of a series of MRD parking slots. When signaled by the system controller, the processing extension module 400 moves the MRD to a magnetic elution slot to separate the eluted magnetic particles and target material, and the PCR pipettor begins the PCR process. The pipettor first dispenses oil to all processing vials queued for test. The pipettor then aspirates eluate/specimen from the MRD and then aspirates reconstitution reagent solution from a reconstitution reagent cartridge or reservoir and dispenses them to a reagent card lyophilized-reagent well. The reconstitution reagent and lyophilized reagent may be drawn into and released from the pipette tip one or more times to ensure adequate and rapid reconstitution. The lyophilized-reagent reconstitutes and the reconstituted mixture is then pipetted to the processing vial and is then capped. The reconstituted mixture, sample, and oil may be drawn into and released from the pipette tip one or more times to ensure adequate mixing. The capped vial is transferred to the centrifuge and then to thermocycler for PCR amplification and fluorometric detection.

Results may be displayed on an instrument monitor or user interface and either printed or communicated to the LIS.

In an embodiment, the analyzer 100 is configured to perform one or more isothermal processes on sample material contained within an MRD. In one embodiment, such an isothermal process may be performed on the contents of the MRD prior to sending the MRD to the processing extension module 400 to perform PCR on a portion of the MRD content material, as discussed above. Alternatively, after the MRD is processed in the processing extension module 400 and an amount of eluate/specimen is transferred from the MRD to one or more vials for performing PCR or other process(es) that the processing extension module 400 is configured to perform, the MRD may be transferred back to the analyzer 100 to perform an isothermal process on the remaining MRD contents.

Exemplary Processes

Figure 41:
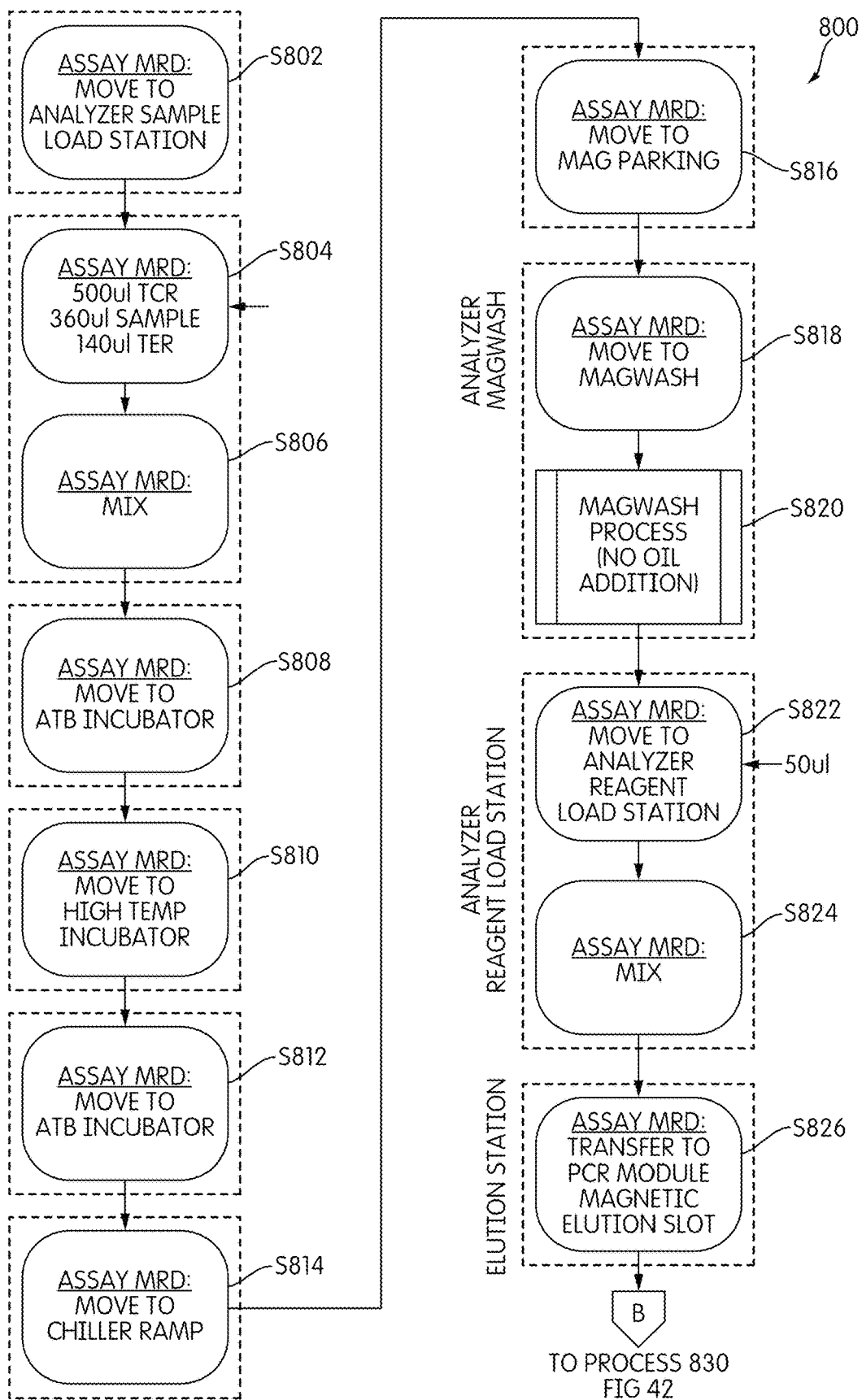
FIG. 41 is a flowchart illustrating the steps of a sample eluate preparation process.
Figure 42:
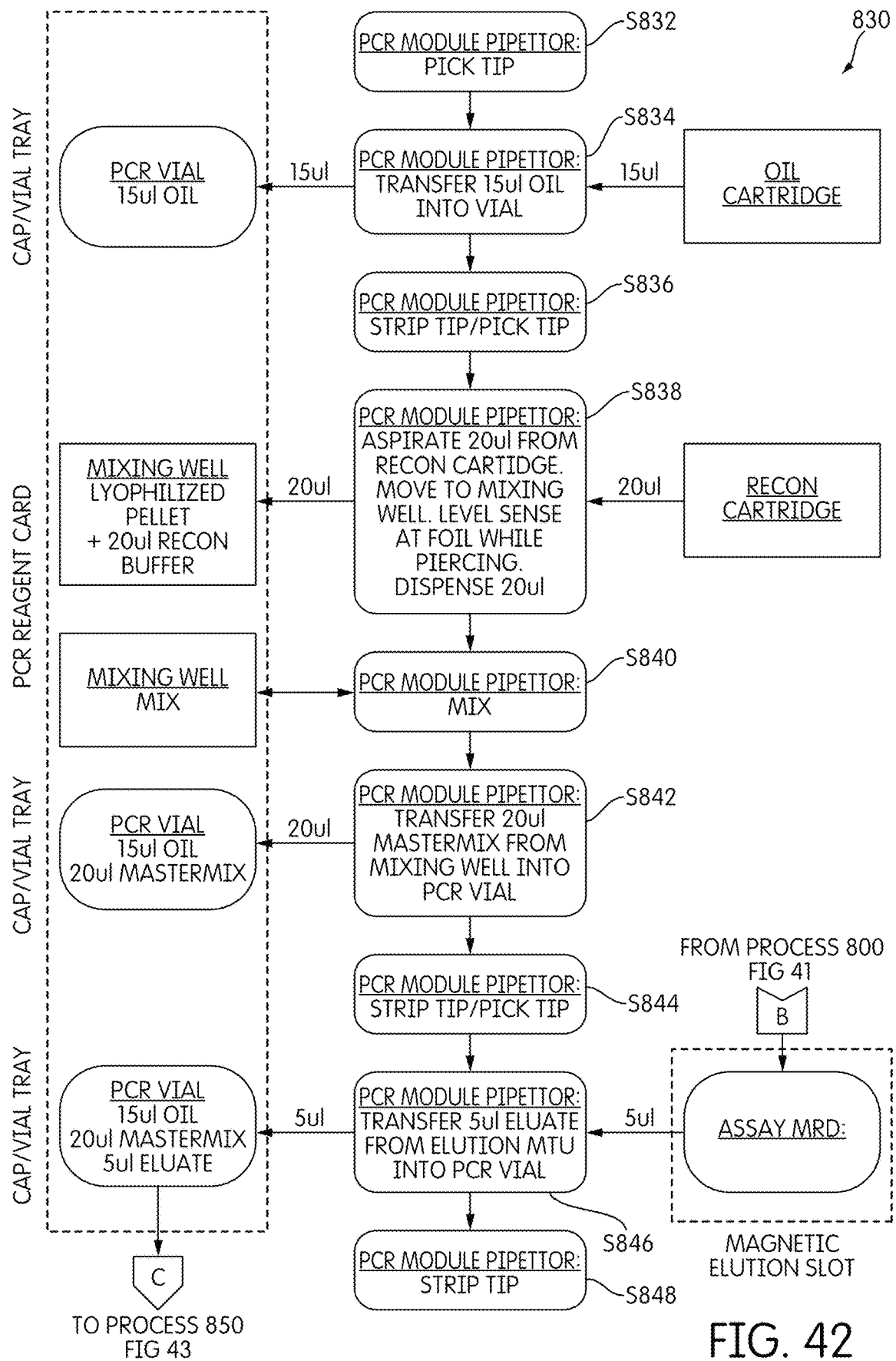
FIG. 42 is a flowchart illustrating the steps of a reaction mixture preparation process.
Figure 43:
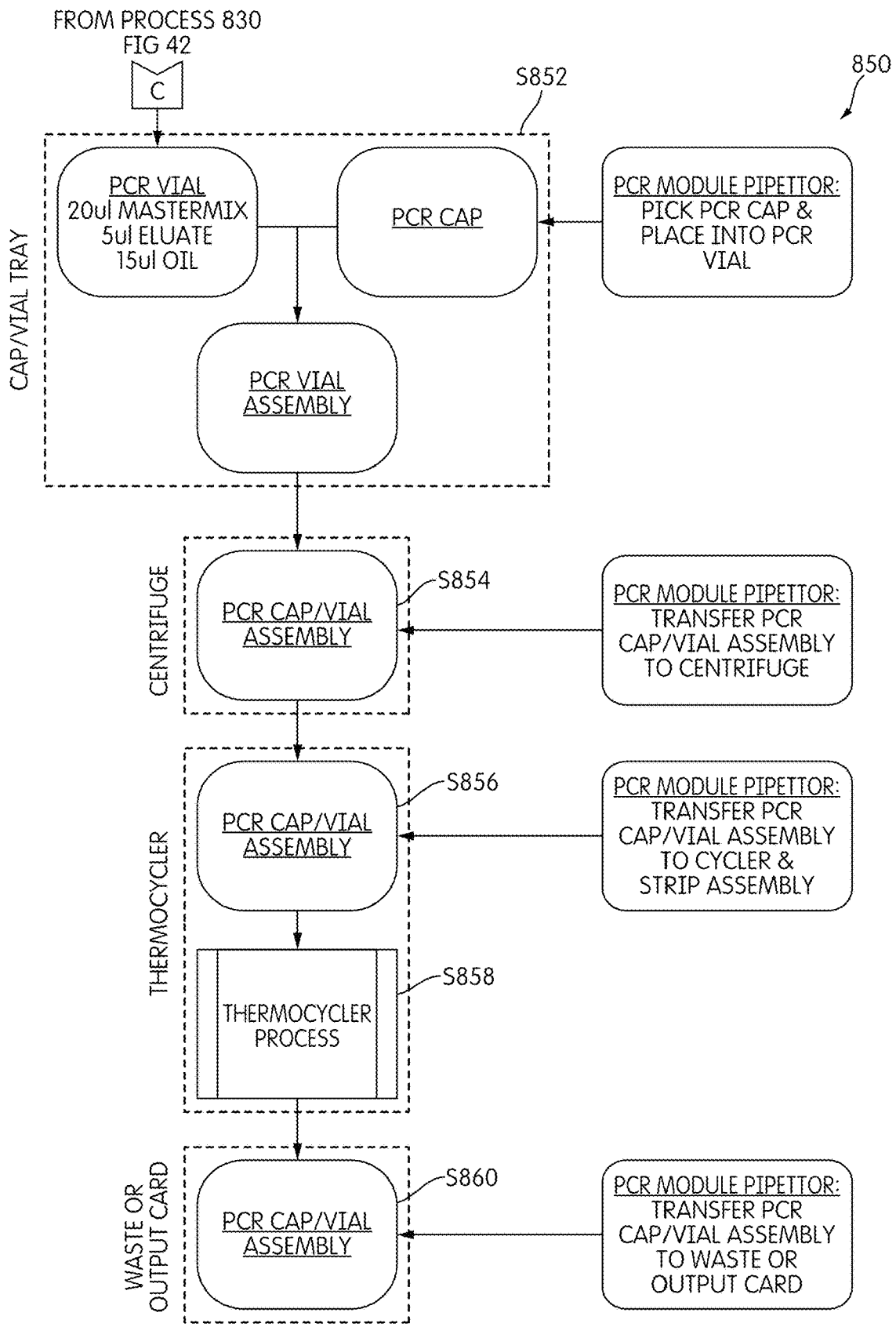
FIG. 43 is a flowchart illustrating the steps of a process for performing an automated biological process, such as a PCR reaction

Details of operation and a process embodying aspects of the present disclosure are shown in the flow charts of FIGS. 41-43. The following processes are exemplary. Other processes may be performed and/or the processes shown herein and described below may be modified, e.g., by omitting and/or reordering certain steps.

A sample eluate preparation process that can be performed using the analyzer 100 and the processing extension module 400 described above is represented by flow chart 800 in FIG. 41. In step S802 of method 800, a reaction receptacle is moved to a location at which reaction materials can be added to the receptacle. For example, the receptacle distributor 150 of the analyzer 100 moves an MRD 160 from the input module 102 to one of the load stations 104, 106 or 108.

In step S804 a fluid transfer apparatus of the analyzer 100 transfers reaction materials to the receptacle. For example, a robotic pipettor of the analyzer 100 transfers a target capture reagent ("TCR") (e.g., 500 µl), sample fluid (e.g., 360 µl), and target enhancer reagent ("TER") (e.g., 1400 into each receptacle vessel 162 of the MRD 160.

In step S806, the reaction materials added to the receptacle in step S804 are mixed. For example, the TCR, sample fluid, and TER added to the vessels 162 of MRD 160 are mixed, e.g., by oscillating the MRD 160 at a high frequency (e.g., 60 seconds at 16 Hz).

In step S808, the receptacle is moved into an environment that will promote the desired chemical and/or biological reaction. For example, the receptacle distributor 150 removes the MRD 160 from the load station 104 and transfers the MRD 160 to one of the incubators 112, 114, 116 (referred to as the AT Binding Incubator "ATB Incubator" in FIG. 41) to incubate the contents of the MRD 160 at a prescribed temperature for a prescribed period of time (e.g., 1800 seconds at 63° C.). Prior to moving the MRD 160 to an incubator, the MRD 160 may first be placed in one of the temperature ramping stations 110 (e.g., 300 seconds at 65° C.) to elevate the temperature of the MRD 160 and its contents to a temperature that is closer to that of the incubator into which the MRD 160 will be transferred so as to minimize temperature fluctuations within the incubator.

The desired chemical and/or biological reaction may require two or more incubations at different temperatures. Thus, in accordance with one implementation of the disclosure, in step S810, the receptacle distributor 150 removes the MRD 160 from one of the incubators and transfers the MRD 160 to another incubator (referred to as the "High Temp Incubator" in FIG. 41) that is at a different (e.g., higher or lower) temperature than the first incubator to continue to incubate the contents of the MRD 160 at a prescribed temperature for a prescribed period of time (e.g., 600 seconds at 43.7° C.).

In step S812, the receptacle distributor 150 removes the MRD from the second temperature incubator and returns the MRD 160 to another incubator at a different temperature, which may be the same incubator (e.g., the "ATB Incubator") the MRD was placed into in step S808.

At the conclusion of the incubation step(s), it may be desirable to cool the temperature of the contents of the receptacle, for example to terminate any reaction occurring within the receptacle. Thus, in one example, in step S814, the receptacle distributor 150 may remove the MRD 160 from the incubator and transfer the MRD 160 to a chiller module 122 (referred to as a "Chiller Ramp" in FIG. 41), maintained at a predetermined temperature.

Next, assuming the reaction performed within the receptacle includes the hybridization of a target capture probe comprising magnetic particles to an analyte of interest (e.g., a target nucleic acid), a magnetic separation procedure is performed on the contents of the receptacle. Thus, in step S816, the receptacle distributor 150 removes the MRD 160 from a chiller module 122 after a predetermined period of time (e.g., 830 seconds), and transfers the MRD 160 to a magnetic parking station comprising magnets for attracting magnetic particles within each receptacle vessel 162 to the walls of the receptacles 162 to pull the particles out of suspension. In step S818, after a prescribed period of time within the magnetic parking station (e.g., 300 second), the receptacle distributor 150 removes the MRD 160 from the magnetic parking station and transfers the MRD 160 to a magnetic separation wash station 118 or 120. In step S820, a magnetic wash procedure is performed on the contents of the MRD 160 placed into the magnetic wash station. One exemplary embodiment of the magnetic separation procedure involves a number magnetic dwells during which the contents of the receptacle are exposed to a magnetic force for a predetermined period of time, and after each magnetic dwell, while the contents are still exposed to the magnetic force, the fluid contents are aspirated from the receptacle, leaving the magnetic particles behind in the receptacle. In one exemplary embodiment, three magnetic dwells of 120 seconds each are performed. At the conclusion of each magnetic dwell, the magnetic force is removed from the contents of the receptacle. After each magnetic dwell, except the last magnetic dwell, an amount of wash fluid (e.g., 1000 µl of wash buffer) is added to the receptacle to re-suspend the magnetic particles prior to beginning the next magnetic dwell.

After the magnetic wash process is complete (e.g., after the last magnetic dwell followed by an aspiration of the non-magnetic fluid contents of the receptacle), in step S822, the receptacle distributor 150 retrieves the MRD 160 from the magnetic separation wash station 118 or 120 and moves the MRD 160 to one of the load stations 104, 106 or 108. In the load station, an amount of elution buffer (e.g., 50-110 µl) is transferred, e.g., by a fluid transfer apparatus such as a robotic pipettor, from one of the elution bottles 502, 504 transferred into the analyzer 100 by the reagent bottle transport 550 of the reagent bottle drawer 500 of the processing extension module 400.

In some embodiments, it may be desirable to heat or incubate the contents of the MRD 160 to improve the efficiency of the nucleic acid elution.

In step S824, following the addition of the elution buffer, the contents of the MRD 160 are mixed by agitating the MRD 160.

In step S826, the MRD 160 is transferred from the analyzer 100 to a magnetic elution slot 620 the processing extension module 400. First, the receptacle distributor 150 of the analyzer 100 retrieves the MRD 160 from the load station 104, 106 or 108 and transfers the MRD 160 to an end of the transport track assembly 154 closest to the processing extension module 400. The distribution head 152 of the receptacle distributor 150 places the MRD into the receptacle handoff module 602 of the processing extension module 400. The receptacle handoff module 602 then rotates the MRD 160 and presents it to the rotary distributor 312. The rotary distributor 312 extends its hook 318 and engages the manipulation structure 166 of the MRD 160 by rotating a few degrees to place the hook 318 into the manipulation structure 166 and then withdraws the hook 318 to pull the MRD 160 into the distributor head 314 of the rotary distributor 312. The rotary distributor 312 then rotates to align the MRD 160 carried therein with one of the magnetic elution slots 620 of the TCR module 400 (or optionally MRD storage 608). The rotary distributor 312 then extends its hook 318 to push the MRD 160 into the magnetic elution slot 620 and rotates a few degrees to remove the hook 318 from the manipulation structure 166.

The process next proceeds to process 830 shown in FIG. 42.

Referring to FIG. 42, a reaction mixture preparation process is represented by flow chart 830. One or more of the steps of process 830 may proceed in parallel with one or more of the steps of process 800 shown in FIG. 41.

At step S832 the fluid transfer pipettor 410 of the processing extension module 400 picks up a disposable tip 584 from a disposable tip tray 582 carried in one of the tip drawers 580.

In step S834, the fluid transfer pipettor 410 transfers an amount of oil (e.g., 15 µl) from an oil bottle carried in the reagent bottle drawer 500 to one or more processing vials 464 held in the vial/cap trays 460 of the processing vial/cap drawer 440.

In step S836, the fluid transfer pipettor 410 moves to a trash chute 426 to strip the disposal pipettor tip 584 therefrom and discard the tip into the trash chute 426. Fluid transfer pipettor 410 then returns to the disposable tip tray 582 and picks up another disposable pipettor tip 584.

In step S838, fluid transfer pipettor 410 transfers an amount of reconstitution reagent (e.g., 20 µl) from a reconstitution reagent bottle held in the reagent bottle drawer 500 to a mixing well 762 of a PCR reagent card 760 that was previously transferred by the rotary distributor 312 from the storage chamber 742 to a reagent card loading station 640. In one embodiment, before the reconstitution reagent is dispensed into the mixing well 762, the pipettor 410 performs a level sense at the foil 766 prior to piercing the foil 766 with the pipette tip 584. The level-sense performed on the foil of the card to "calibrate" the height of the card relative to the pipettor. It is important that the pipettor tip go to the bottom of the mixing well accurately for reagent aspiration.

In step S840, the fluid within the mixing well 762 is mixed to dissolve the lyophilized reagent 768. In one example, the fluid transfer pipettor 410 mixes the fluid within the mixing well 762 by alternately aspirating the fluid into the pipettor tip 584 and dispensing the fluid back in the well 762 one or more times to dissolve the lyophilized reagent 768.

In step S842, the fluid transfer pipettor 410 transfers an amount, (e.g., 20 μl) of the reconstituted reagent from the mixing well 762 of the PCR reagent card 760 (referred to as "Mastermix" in FIG. 42), into a vial 464.

In step S844, the fluid transfer pipettor 410 moves to the trash chute 426 and strips the pipettor tip 584 into the trash chute. The fluid transfer pipettor 410 then moves to the disposable tip tray 582 and picks up a new disposable pipette tip 584.

Block "B" in FIG. 42 represents the integration of process 800 shown in FIG. 41 with process 830 shown in FIG. 42. An MRD 160 containing a sample mixture (which, in this exemplary embodiment, was purified in a magnetic separation procedure) and an elution buffer is held in a magnetic elution slot 620, having been placed there in step S826 of process 800. In one embodiment, the MRD 160 is held in the magnetic elution slot 620 for dwell period of at least 120 seconds.

In step S846 of process 830, the fluid transfer pipettor 410 transfers an amount of eluate (e.g., 5 μl) from the MRD 160 held in the elution slot 620 to the processing vial 464 to which oil and reagent were added in steps S834 and S842, respectively.

In step S848, the fluid transfer pipettor 410 moves back to the trash chute 426 and strips the disposal pipettor tip 584 into the trash chute.

The process now proceeds to process 850 shown in FIG. 43.

Referring to FIG. 43, a process for performing an automated biological process, such as a PCR reaction, is represented by flow chart 850. Block "C" in FIG. 43 represents the integration of process 830 shown in FIG. 43 with process 850 shown in FIG. 43.

In step S852, the fluid transfer pipettor 410 picks up a processing vial cap 476 from the cap well 440 of the cap/vial tray 460 by inserting the pipettor probe 422 (without a disposable pipette tip thereon) into the cap 476 (see e.g., 4002, 26). The fluid transfer pipettor 410 then picks up the cap 476, which is held onto the pipettor probe 422 by friction, and inserts the cap 476 into the processing vial 464 held in the processing vial well 474 until the cap 476 locks with the vial 464 to form a cap/vial assembly (see e.g., FIG. 25).

In step S854, the fluid transfer pipettor 410 transfers the cap/vial assembly held to the pipettor probe 422 by friction to the centrifuge 588, where a stripping apparatus removes the cap/vial assembly from the pipettor probe 422 to deposit the cap/vial assembly into the centrifuge 588.

In Step 856, following a specified period of time in the centrifuge, the vial transfer pipettor 418 inserts its pipettor probe 422 into the cap 476 of the cap/vial assembly held in the centrifuge 588 and removes the cap/vial assembly from the centrifuge 588 and transfers the cap/vial assembly to an incubator module, such as the thermocycler 432. A stripping apparatus removes the cap/vial assembly from the pipettor probe 422 of the vial transfer pipettor 418.

In step S858, an incubation process is performed. The incubation process may include PCR thermocycling comprising multiple cycles of temperatures varying between 95° C. for denaturation, 55° C. for annealing, and 72° C. for synthesis. During the thermocycler process an emission signal from the contents of the processing vial may be monitored. For example, fluorescence monitoring at one or more colored wavelengths during each PCR cycle may be measured using a signal detecting apparatus, such as a fluorometer, operatively integrated with the thermocycler 432. Periodic fluorescence intensity measurements at each wavelength may be made at regular intervals to generating fluorescence time series data for later processing and analysis.

In step S860, following the PCR process of step S858, the vial transfer pipettor 418 retrieves the cap/vial assembly from the thermocycler 432 and transfers the cap/vial assembly to a trash chute 424 where the cap/vial assembly is stripped from the pipettor probe 422 into the trash chute 424, or the cap/vial assembly is transported to an output card in the storage/expansion module.

Hardware and Software

Aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to a user for providing information to the user, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the disclosures requires features or combinations of features other than those expressly recited in the claims. Accordingly, the present disclosure is deemed to include all modifications and variations encompassed within the spirit and scope of the following appended claims.

What is claimed is:

1. An automated fluid handling system comprising:
a container drawer configured to move between an open position and a closed position, the container drawer comprising a removable container carriage configured to support at least one first container; and
a container transport configured to move the container carriage between (a) a first carriage position on the container drawer when the container drawer is at the closed position to (b) a second carriage position within the system, wherein the container transport comprises a movable sled having a carriage hook configured to engage the container carriage, the movable sled and carriage hook being configured to pull the container carriage laterally relative to a longitudinal dimension of the drawer off the container drawer and onto the container transport, wherein at the second carriage position, the container carriage is separated from the container drawer, and the at least one first container supported by the container carriage is accessible to a first robotic pipettor of the system, and wherein the container drawer further comprises a lock having (a) a first lock configuration preventing relative movement between the container carriage and the container drawer and (b) a second lock configuration allowing relative movement between the container carriage and the container drawer, wherein the lock is configured to be set at the second lock configuration when the container drawer is at the closed position.

2. The system of claim 1, wherein the lock comprises:
a locking leg configured to extend into a lock recess formed in a bottom of the container carriage at the first lock configuration and configured to be withdrawn from the lock recess at the second lock configuration; and
a trigger leg configured to operatively engage a lock trigger at the closed position of the container drawer, thereby moving the locking leg from the first lock configuration to the second lock configuration.

3. The system of claim 1, wherein the container transport further comprises a motor and a belt coupling the sled to the motor.

4. The system of claim 3, wherein the motor comprises a rotary encoder for monitoring and controlling the position of the motor.

5. The system of claim 1, wherein the container transport comprises at least one sensor configured to detect a position of the sled.

6. The system of claim 1, wherein the container transport translates the container carriage between the first carriage position and the second carriage position.

7. The system of claim 1, wherein the container drawer further comprises a tray configured to support at least one second container, the container carriage being disposed at an end of the tray, and the tray and the container carriage being movable together as the container drawer moves from the open position to the closed position.

8. The system of claim 7, wherein the at least one second container is accessible to a second robotic pipettor, distinct from the first robotic pipettor.

9. The system of claim 7, wherein the at least one first container comprises a container containing an elution buffer.

10. The system of claim 9, wherein the at least one second container comprises a container containing an oil or a reconstitution buffer.

11. The system of claim 9, wherein the container carriage is configured to support two first containers, each containing the elution buffer.

12. A fluid handling method for the fluid handling system of claim 1, comprising:
(a) moving the container drawer from the open position to the closed position, the removable container carriage supporting at least one first container;
(b) using the movable sled to laterally pull the container carriage from the first carriage position on the container drawer to the second carriage position within the system; and
(c) using a first robotic pipettor to remove a fluid from the at least one first container supported by the container carriage at the second carriage position.

13. The fluid handling method of claim 12, further comprising:
after step (c), using the automated container transport to move the container carriage from the second carriage position to the first carriage position on the container drawer.

14. The fluid handling method of claim 12, further comprising using a second robotic pipettor separate from the first robotic pipettor to remove a second fluid from at least one second container supported by the container drawer at the closed position.

15. The fluid handling method of claim 14, wherein the second fluid is different than the first fluid.

16. The fluid handling method of claim 14, wherein the first fluid comprises an elution buffer, and the second fluid comprises an oil or a reconstitution buffer.

17. The fluid handling method of claim 12, wherein step (c) further comprises using the first robotic pipettor to remove the first fluid from two first containers supported by the container carriage at the second carriage position.

* * * * *